(12) United States Patent
Raymond et al.

(10) Patent No.: US 6,635,629 B2
(45) Date of Patent: Oct. 21, 2003

(54) 3-NITROGEN-6,7-DIOXYGEN STEROIDS AND USES RELATED THERETO

(75) Inventors: Jeffery R. Raymond, Vancouver (CA); Claudia E. Kasserra, North Vancouver (CA); Yaping Shen, Port Coquitlam (CA)

(73) Assignee: Inflazyme Pharmaceuticals Ltd., Richmond (CA)

( * ) Notice: Subject to any disclaimer, the term of this patent is extended or adjusted under 35 U.S.C. 154(b) by 0 days.

(21) Appl. No.: 09/845,775

(22) Filed: Apr. 30, 2001

(65) Prior Publication Data

US 2002/0072510 A1 Jun. 13, 2002

Related U.S. Application Data

(60) Provisional application No. 60/200,617, filed on Apr. 28, 2000.

(51) Int. Cl.[7] .......................... A61K 31/56; C07J 41/00; C07J 71/00
(52) U.S. Cl. .......................... 514/182; 552/521; 540/61
(58) Field of Search .................. 514/182; 552/521; 540/61

(56) References Cited

U.S. PATENT DOCUMENTS

| | | | |
|---|---|---|---|
| 5,637,691 A | 6/1997 | Frye et al. | 540/106 |
| 5,721,226 A | 2/1998 | Frye et al. | 514/169 |
| 5,733,899 A | 3/1998 | Frye et al. | 514/169 |
| 5,817,632 A | 10/1998 | Hsia | 514/21 |
| 5,847,172 A | 12/1998 | Zasloff et al. | 552/521 |
| 5,856,535 A * | 1/1999 | Zasloff et al. | 552/521 |
| 5,874,597 A | 2/1999 | Jones | 552/521 |
| 6,046,185 A | 4/2000 | Burgoyne et al. | 514/178 |
| 6,060,465 A | 5/2000 | Miljkovic et al. | 514/169 |

FOREIGN PATENT DOCUMENTS

| | | |
|---|---|---|
| WO | WO 91/10743 | 7/1991 |
| WO | WO 94/14451 | 7/1994 |
| WO | WO 94/20520 | 9/1994 |
| WO | WO 96/22791 | 8/1996 |
| WO | WO 96/36230 | 11/1996 |
| WO | WO 98/02450 | 1/1998 |
| WO | WO 98/27106 | 6/1998 |
| WO | WO 99/44616 | 9/1999 |

OTHER PUBLICATIONS

Cram and Allinger, "Mold Metabolites. VIII. Contribution to the Elucidation of the Structure of Helvolic Acid," *Journal of the American Chemical Society* 78:5275–5284, Oct. 20, 1956.

Foussard–Blanpin, "Pharmacological Study of 3α–Aminopregnane," *Ann. Pharm. FR.* 27(3):191–200, 1969. (Abstract Only, STN Accession No. 71:79454).

McGowan et al., "The Production of a Reactive Oxygen Intermediate during the Induction of Apoptosis by Cytotoxic Insult," *Experimental Cell Research* 238(1):248–256, Jan. 10, 1998.

Mendenhall et al., "Anabolic Steriod Effects on Immune Function: Differences Between Analogs," *J. Steriod Biochem. Mol. Biol* 37(1):71–76, 1990. (Abstract Only, STN Accession No. 114:17714).

Spyriounis et al., "Novel N–Substituted 3–Aminosteroids Which Exhibit Anti–Inflammatory Properties and Influence Free Radical Processes," *Eur. J. Med. Chem.* 28(6):521–525, 1993.

\* cited by examiner

*Primary Examiner*—Barbara P. Badio
(74) *Attorney, Agent, or Firm*—Seed IP Law Group PLLC

(57) ABSTRACT

A compound of the formula

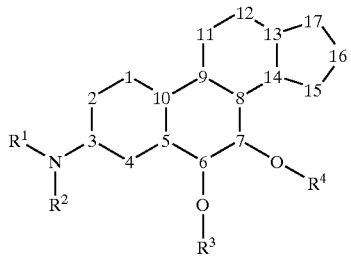

or pharmaceutically acceptable salts, solvates, and stereoisomers thereof, in isolation or in mixture, wherein the R groups are as defined by the present specification. The compounds may be formulated into pharmaceutical compositions, and used in the treatment and/or prevention of various conditions, including inflammation, asthma, an allergic disease, chronic obstructive pulmonary disease, atopic dermatitis, solid tumors, AIDS, ischemia, and cardiac arrhythmias.

31 Claims, 7 Drawing Sheets

3-NITROGEN-6,7-DIOXYGEN STEROIDS AND USES RELATED THERETO

CROSS-REFERENCE TO RELATED APPLICATION

This application claims the benefit of U.S. Provisional Patent Application No. 60/200,617 filed Apr. 28, 2000, where this provisional application is incorporated herein by reference in its entirety.

TECHNICAL FIELD

This invention is directed towards 3-nitrogen-6,7-dioxygenated steroids, compositions including these steroids, and therapeutic uses related thereto.

BACKGROUND OF THE INVENTION

The Inflammatory Response (Inflammation)

Inflammation is an essential localized host response to invading microorganisms or tissue injury which involves cells of the immune system. The classic signs of inflammation include redness (erythema), swelling (edema), pain and increased heat production (pyrema) at the site of injury. The inflammatory response allows the body to specifically recognize and eliminate an invading organism and/or repair tissue injury. Many of the acute changes at the site of inflammation are either directly or indirectly attributable to the massive influx of leukocytes (e.g., neutrophils, eosinophils, lymphocytes, monocytes) which is intrinsic to this response. Leukocytic infiltration and accumulation in tissue results in their activation and subsequent release of inflammatory mediators such as $LTB_4$, prostaglandins, TNF-$\alpha$, IL-$\beta$, IL-8, IL-5, IL-4, histamine, proteases and reactive oxygen species for example.

Normal inflammation is a highly regulated process that is tightly controlled at several levels for each of the cell types involved in the response. For example, expression of the pro-inflammatory cytokine TNF-$\alpha$ is controlled at the level of gene expression, translation, post-translational modification and release of the mature form from the cell membrane. Many of the proteins up-regulated during inflammation are controlled by the transcription factor, NF-$\kappa$B. Pro-inflammatory responses are countered in some instances by endogenous anti-inflammatory mechanisms such as generation of IL-10. A characteristic of a normal inflammatory response is that it is temporary in nature and is followed by a resolution phase which brings the state of the tissue back to its prior condition. The resolution phase is thought to involve up-regulation of anti-inflammatory mechanisms, such as IL-10, as well as down-regulation of the pro-inflammatory processes.

Inflammatory Disease

Inflammatory disease occurs when an inflammatory response is initiated that is inappropriate and/or does not resolve in the normal manner but rather persists and results in a chronic inflammatory state. Inflammatory disease may be systemic (e.g., lupus) or localized to particular tissues or organs and exerts an enormous personal and economic burden on society. Examples of some of the most common and problematic inflammatory diseases include asthma, allergy, rheumatoid arthritis, inflammatory bowel disease, psoriasis, emphysema, colitis, graft vs host disease, contact dermatitis, and ischemia-reperfusion injury. Other disease states such as immunodeficiency diseases are now known to be associated with altered regulation of the chemokine/cytokine network and their receptors, which can alter viral replication and AIDS pathogenesis.

Many of the tissue, cellular and biochemical processes which are perturbed in inflammatory disease have been elucidated and this has allowed the development of experimental models or assays to mimic the disease state. These in-vitro and in-vivo assays enable selection and screening of compounds with a high probability of therapeutic efficacy in the relevant inflammatory disease. For example, the ability of a compound to inhibit the allergen-induced accumulation of inflammatory cells such as eosinophils and lymphocytes in the lavage fluid obtained from sensitized animals is indicative of anti-asthma activity. In particular, this model system is useful in the evaluation of the effects of compounds in the treatment of the late phase response and hyper-responsiveness that is characteristic of asthma, when lung inflammation is apparent.

Asthma and Allergy

Asthma and allergy are closely related with good evidence from clinical studies demonstrating a strong correlation between the severity of asthma and the degree of atopy (allergy). Sensitization to allergens is believed to be the most important risk factor for asthma in both children and adults, with approximately 90% of asthma cases exhibiting atopy.

Allergy is characterized by an increased blood serum IgE (antibody) level. Repeated exposure to allergens, in a process called sensitization, is normally required to trigger atopy and the subsequent asthmatic or allergic response. Once B cells are exposed to allergens, they produce antibodies which bind to the surface of mast cells. The crosslinking of two antibodies by the antigen causes a series of reactions resulting in degranulation and the release of a number of mediators which modulate the inflammatory response. Mediators that are released or generated during the asthmatic and allergic response include histamine, leukotrienes, prostaglandins, cytokines and tryptase.

Asthma is characterized by hyperresponsiveness of the airways, episodic periods of bronchospasm and chronic inflammation of the lungs. Obstruction of the airways is reversible with time or in response to drug therapies. Patients exhibiting normal airflow may be hyperreactive to a variety of naturally occurring stimuli, e.g., cold air, exercise, chemicals and allergen. The most common event initiating an asthmatic response is an immediate hypersensitivity to common allergens including ragweed pollen, grass pollen, various fungi, dust mites, cockroaches and domestic animals. The symptoms of the disease include chest tightness, wheezing, shortness of breath and coughing. Asthma incidence and mortality has been increasing worldwide, doubling over the past 20 years despite modem therapies.

The responses of the airways to allergen is complex and consists of an early asthmatic response (EAR) which peaks 20–30 min after exposure to the stimuli, is characterized by bronchoconstriction and normally resolves after 1½ to 2 hours. The late asthmatic response (LAR) generally occurs 3–8 hours after initial exposure, and involves both bronchoconstriction and the development of inflammation and edema in the lung tissue. This inflammation often becomes chronic, with epithelial damage occurring and infiltration of the lungs with inflammatory cells such as eosinophils and neutrophils.

Current Treatments for Asthma

Glucocorticoids (steroids) are the most effective long-term therapy for the treatment of asthma. For example, due to the presence of airway inflammation even in mild asthma, inhaled steroids are used even in early stage drug therapy. Although steroids are effective anti-inflammatories they are not very useful for the control of acute asthma attacks.

Orally delivered steroids are associated with significant side-effects and consequently their chronic use in the control of asthma is minimal. Combination therapy is often employed for orally delivered steroids, where combination therapy may be divided into the following areas: anti-inflammatory drugs (e.g., inhaled and oral steroids), bronchodilators, (e.g., $\beta_2$-agonists, xanthines, anticholinergics), and mediator inhibitors (e.g., cromolyns and leukotriene antagonists). In general, moderate to severe asthma patients are poorly served by the present armamentarium of drugs. Drugs that are safe are only marginally effective, while effective drugs have unacceptable side effects with extensive monitoring of patients required. Products under development continue to meet challenges related to side-effects (e.g., emesis side-effects characteristic of certain phosphodiesterase 4 inhibitors) and poor pharmacokinetic and metabolism parameters. There is a significant need for therapeutic agents that achieve safe and effective treatment of inflammatory diseases such as asthma and allergy. The present invention provides these and related benefits as described herein.

SUMMARY OF THE INVENTION

In one aspect, the present invention provides compounds according to formula (1) and pharmaceutically acceptable salts, solvates, stereoisomers and prodrugs thereof, in isolation or in mixtures,

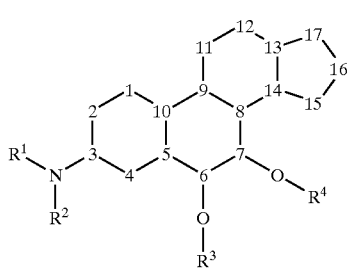

(1)

wherein, independently at each occurrence:
  $R^1$ and $R^2$ are selected from hydrogen, oxygen so as to form nitro or oxime, amino, —$SO_3$—R, and organic groups having 1–30 carbons and optionally containing 1–6 heteroatoms selected from nitrogen, oxygen, phosphorous, silicon, and sulfur, where $R^2$ may be a direct bond to numeral 3, or $R^1$ and $R^2$ may, together with the N to which they are both bonded, form a heterocyclic structure that may be part of an organic group having 1–30 carbons and optionally containing 1–6 heteroatoms selected from nitrogen, oxygen and silicon; and where $R^1$ may be a 2, or 3 atom chain to numeral 2 so that —N—$R^1$— forms part of a fused bicyclic structure to ring A;
  $R^3$ and $R^4$ are selected from direct bonds to 6 and 7 respectively so as to form carbonyl groups, hydrogen, or a protecting group such that $R^3$ and/or $R^4$ is part of hydroxyl or carbonyl protecting group;
  numerals 1 through 17 each represent a carbon, where carbons at numerals 1, 2, 4, 11, 12, 15, 16 and 17 may be independently substituted with
    (a) one of: =O, =C($R^5$)($R^5$), =C=C($R^5$)($R^5$), —C($R^5$)($R^5$)(C($R^5$)$R^5$))$_n$— and —(O(C($R^5$)($R^5$))$_n$ O)— wherein n ranges from 1 to about 6; or
    (b) two of the following, which are independently selected: —X, —N($R^1$)($R^2$), —$R^5$ and —$OR^6$;
  and where carbons at numerals 5, 8, 9, 10, 13 and 14 may be independently substituted with one of —X, —$R^5$, —N($R^1$)($R^2$) or —$OR^6$;

in addition to the —$OR^3$ and —$OR^4$ groups as shown, each of carbons 6 and 7 may be independently substituted with one of —X, —N($R^1$)($R^2$), —$R^5$ or —$OR^6$;
  each of rings A, B, C and D is independently fully saturated, partially saturated or fully unsaturated;
  $R^5$ at each occurrence is independently selected from H, X, and $C_{1-30}$ organic moiety that may optionally contain at least one heteroatom selected from the group consisting of boron, halogen, nitrogen, oxygen, silicon and sulfur; where two geminal $R^5$ groups may together form a ring with the carbon atom to which they are both bonded;
  $R^6$ is H or a protecting group such that —$OR^6$ is a protected hydroxyl group, where vicinal —$OR^6$ groups may together form a cyclic structure that protects vicinal hydroxyl groups, and where geminal —$OR^6$ groups may together form a cyclic structure that protects a carbonyl group; and
  X represents fluoride, chloride, bromide and iodide.

In another aspect, the present invention provides a pharmaceutical composition comprising a steroid compound as set forth above, and a pharmaceutically acceptable carrier, excipient or diluent.

In another aspect, the present invention provides a method of treating inflammation comprising administering to a subject in need thereof a therapeutically-effective amount of a steroid compound as set forth above.

In another aspect, the present invention provides a method of treating inflammation prophylactically comprising administering to a subject in need thereof a prophylactically-effective amount of a steroid compound as set forth above.

In another aspect, the present invention provides a method of treating asthma comprising administering to a subject in need thereof a therapeutically-effective amount of a steroid compound as set forth above.

In another aspect, the present invention provides a method of treating allergic disease including but not limited to dermal and ocular indications comprising administering to a subject in need thereof a therapeutically-effective amount of a steroid compound as set forth above.

In another aspect, the present invention provides a method of treating chronic obstructive pulmonary disease comprising administering to a subject in need thereof a therapeutically-effective amount of a steroid compound as set forth above.

In another aspect, the present invention provides a method of treating atopic dermatitis comprising administering to a subject in need thereof a therapeutically-effective amount of a steroid compound as set forth above.

In another aspect, the present invention provides a method of treating solid tumours comprising administering to a subject in need thereof a therapeutically-effective amount of a steroid compound as set forth above.

In another aspect, the present invention provides a method of treating AIDS comprising administering to a subject in need thereof a therapeutically-effective amount of a steroid compound as set forth above.

In another aspect, the present invention provides a method of treating ischemia reperfusion injury comprising administering to a subject in need thereof a therapeutically-effective amount of a steroid compound as set forth above.

In another aspect, the present invention provides a method of treating cardiac arrhythmias comprising administering to a subject in need thereof a therapeutically-effective amount of a steroid compound as set forth above.

These and related aspects of the present invention are described in more detail below.

BRIEF DESCRIPTION OF THE DRAWING

FIG. 2A shows the accumulation of eosinophils, FIG. 2B shows the accumulation of neutrophils, and FIG. 2C shows the accumulation of lymphocytes.

FIG. 3A shows the accumulation of eosinophils, FIG. 3B shows the accumulation of neutrophils, and FIG. 3C shows the accumulation of lymphocytes.

DETAILED DESCRIPTION OF THE INVENTION

Figure 1A:
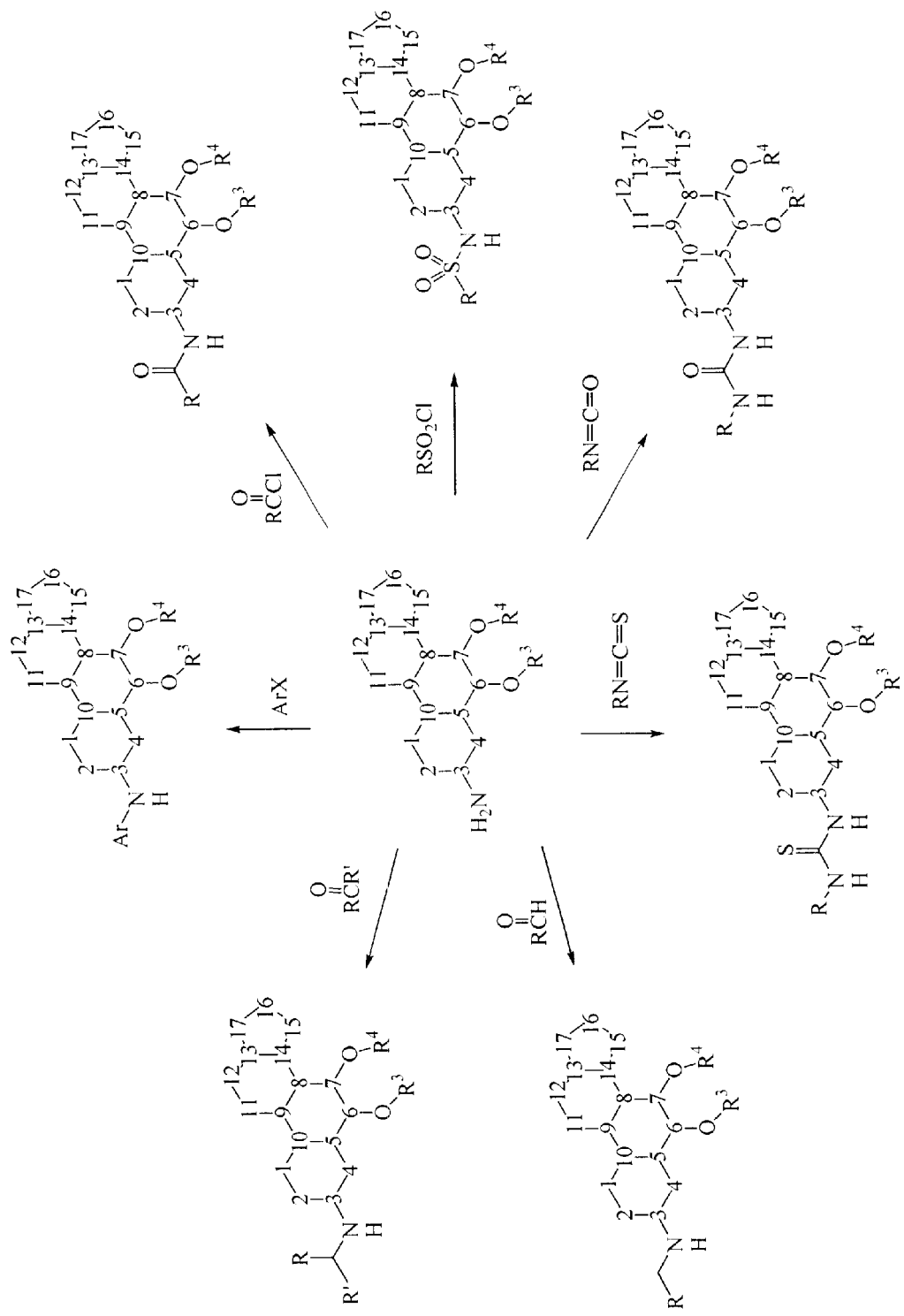
FIGS. 1A and 1B depict summaries of synthetic transformations that may be used to convert a 3-amino steroid into a 3-nitrogen steroid of the present invention.

The present invention provides compounds, compositions and methods useful in the treatment and/or prevention of various disease conditions. For example, in one aspect, the present invention provides a method of treating and/or preventing an inflammatory disease. The method includes administering to a subject in need thereof an effective amount of a compound of formula (1) or pharmaceutically acceptable salt, solvate, stereoisomer or prodrug thereof, or an effective amount of a composition containing a compound of formula (1) or pharmaceutically acceptable salt, solvate, stereoisomer or prodrug thereof.

Before describing the invention in further detail, certain definitions as used herein are provided with the following definitions, and certain conventions used herein are also set forth.

A. Definition of Terms

As used herein, the following terms have the indicated meaning, unless clearly indicated otherwise.

"Alkyl" is a monovalent, saturated or unsaturated, straight, branched or cyclic, aliphatic (i.e., not aromatic) hydrocarbon group. In various embodiments, the alkyl group has 1–20 carbon atoms, i.e., is a C1–C20 (or $C_1$–$C_{20}$) group, or is a C1–C18 group, a C1–C12 group, a C1–C6 group, or a C1–C4 group. Independently, in various embodiments, the alkyl group: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than two triple bonds); is, or includes, a cyclic structure; is acyclic. Exemplary alkyl groups include $C_1$alkyl (i.e., —CH$_3$ (methyl)), $C_2$alkyl (i.e., —CH$_2$CH$_3$ (ethyl), —CH═CH$_2$ (ethenyl) and —C≡CH (ethynyl)) and $C_3$alkyl (i.e., —CH$_2$CH$_2$CH$_3$ (n-propyl), —CH(CH$_3$)$_2$ (i-propyl), —CH═CH—CH$_3$ (1-propenyl), —C≡—C—CH$_3$ (1-propynyl), —CH$_2$—CH═CH$_2$ (2-propenyl), —CH$_2$—C≡—CH (2-propynyl), —C(CH$_3$)═CH$_2$ (1-methylethenyl), and —CH(CH$_2$)$_2$ (cyclopropyl)).

"Aryl" is a monovalent, aromatic, hydrocarbon, ring system. The ring system may be monocyclic or fused polycyclic (e.g., bicyclic, tricyclic, etc.). In various embodiments, the monocyclic aryl ring is C5–C10, or C5–C7, or C5–C6, where these carbon numbers refer to the number of carbon atoms that form the ring system. A C6 ring system, i.e., a phenyl ring, is a preferred aryl group. In various embodiments, the polycyclic ring is a bicyclic aryl group, where preferred bicyclic aryl groups are C8–C12, or C9–C10. A naphthyl ring, which has 10 carbon atoms, is a preferred polycyclic aryl group.

"Heteroalkyl" is an alkyl group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted.

"Heteroaryl" is a monovalent aromatic ring system containing carbon and at least one heteroatom in the ring. The heteroaryl group may, in various embodiments, have one heteroatom, or 1–2 heteroatoms, or 1–3 heteroatoms, or 1–4 heteroatoms in the ring. Heteroaryl rings may be monocyclic or polycyclic, where the polycyclic ring may contained fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. Exemplary heteroaryl groups include benzofuran, benzothiophene, furan, imidazole, indole, isothiazole, oxazole, piperazine, pyrazine, pyrazole, pyridazine, pyridine, pyrimidine, pyrrole, quinoline, thiazole and thiophene.

"Heteroatom" is a halogen, nitrogen, oxygen, phosphorous, silicon or sulfur atom. Groups containing more than one heteroatom may contain different heteroatoms.

"Hydrocarbons" are chemical groups formed exclusively of hydrogen and carbon; "Halocarbons" are chemical groups formed exclusively of halogen and carbon; and "Hydrohalocarbons" are chemical groups formed exclusively of hydrogen, halogen, and carbon.

"Organic groups" and "Organic moieties" are used synonymously, and refer to stable structures having the indicated number and type of atoms.

"Pharmaceutically acceptable salt" and "salts thereof" in the compounds of the present invention refers to acid addition salts and base addition salts.

Acid addition salts refer to those salts formed from compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts refer to those salts formed from compounds of the present invention and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

When any variable occurs more than one time in any constituent or in compounds of formula (1), its definition on each occurrence is independent of its definition at every other occurrence. Combinations of substituents and/or variables are permissible only if such combinations result in stable compounds. The compounds useful in the methods and compositions of the present invention, as well as the compounds of the present invention, may have asymmetric centers and occur as racemates, racemic mixtures and as individual diastereomers, or enantiomers with all isomeric forms being included in the present invention. A racemate or racemic mixture does not imply a 50:50 mixture of stereoisomers.

In another embodiment, the present invention provides pharmaceutical compositions containing a compound of formula (1) as set forth above, in combination with a pharmaceutically-acceptable carrier, diluent or excipient. These compositions may be used for the treatment of inflammation or other conditions as disclosed herein. These compositions may also be formed into a medicament, which may be used in the treatment of, for example, inflammation.

These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 100 wt % of the entire weight of the composition. Inert carriers include any material which does not degrade or otherwise covalently react with a compound of formula (1). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers.

"Pharmaceutically acceptable carriers" for therapeutic use are well known in the pharmaceutical art, and are described, for example, in *Remingtons Pharmaceutical Sciences,* Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

Steroid compounds of the invention have at least four rings, commonly designated as A, B, C and D as shown below, where ring A may be fused to an additional ring:

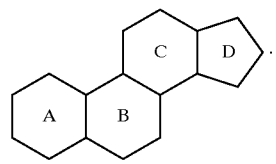

B. Compounds

The present invention provides compounds according to formula (1) and pharmaceutically acceptable salts, solvates, stereoisomers and prodrugs thereof, in isolation or in mixtures,

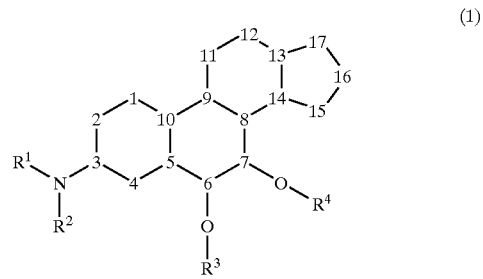

(1)

wherein, independently at each occurrence:

$R^1$ and $R^2$ are selected from hydrogen, oxygen so as to form nitro or oxime, amino, —$SO_3$—R, and organic groups having 1–30 carbons and optionally containing 1–6 heteroatoms selected from nitrogen, oxygen, phosphorous, silicon, and sulfur, where $R^2$ may be a direct bond to numeral 3, or $R^1$ and $R^2$ may, together with the N to which they are both bonded, form a heterocyclic structure that may be part of an organic group having 1–30 carbons and optionally containing 1–6 heteroatoms selected from nitrogen, oxygen and silicon, and where $R^1$ may be a 2, or 3 atom chain to numeral 2 so that —N—$R^1$— forms part of a fused bicyclic structure to ring A;

$R^3$ and $R^4$ are selected from direct bonds to 6 and 7 respectively so as to form carbonyl groups, hydrogen, or a protecting group such that $R^3$ and/or $R^4$ is part of hydroxyl or carbonyl protecting group;

numerals 1 through 17 each represent a carbon, where carbons at numerals 1, 2, 4, 11, 12, 15, 16 and 17 may be independently substituted with (a) one of: =O, =$C(R^5)(R^5)$, =C=$C(R^5)(R^5)$, —$C(R^5)(R^5)(C(R^5)(R^5))_n$— and —$(O(C(R^5)(R^5))_n$ O)— wherein n ranges from 1 to about 6; or (b) two of the following, which are independently selected: —X, —$N(R^1)(R^2)$, —$R^5$ and —$OR^6$;

and where carbons at numerals 5, 8, 9, 10, 13 and 14 may be independently substituted with one of —X, —$R^5$, —N($R^1$)($R^2$) or —O$R^6$;

in addition to the —O$R^3$ and —O$R^4$ groups as shown, each of carbons 6 and 7 may be independently substituted with one of —X, —N($R^1$)($R^2$), —$R^5$ or —O$R^6$;

each of rings A, B, C and D is independently fully saturated, partially saturated or fully unsaturated;

$R^5$ at each occurrence is independently selected from H, X, and $C_{1-30}$ organic moiety that may optionally contain at least one heteroatom selected from the group consisting of boron, halogen, nitrogen, oxygen, silicon and sulfur; where two geminal $R^5$ groups may together form a ring with the carbon atom to which they are both bonded;

$R^6$ is H or a protecting group such that —O$R^6$ is a protected hydroxyl group, where vicinal —O$R^6$ groups may together form a cyclic structure that protects vicinal hydroxyl groups, and where geminal —O$R^6$ groups may together form a cyclic structure that protects a carbonyl group; and X represents fluoride, chloride, bromide and iodide.

In one aspect of the invention, $R^1$ and $R^2$ are selected from hydrogen and organic groups having 1–30 carbons and optionally containing 1–6 heteroatoms selected from nitrogen, oxygen, phosphorous, silicon, and sulfur. Optionally, $R^2$ is a direct bond to numeral 3. In another aspect, $R^1$, $R^2$, and the N to which they are both bonded, form a heterocyclic structure that may be part of an organic group having 1–30 carbons and optionally containing 1–6 heteroatoms selected from nitrogen, oxygen and silicon. In another aspect, $R^1$ is a 2, or 3 atom chain to numeral 2 so that —N—$R^1$—forms part of a fused bicyclic structure to ring A, and the 2 or 3 atoms are selected from C, N and O, so long as a stable structure results. Optionally, in these and other aspects of the present invention, the organic group has 1–20 carbons, while in another optional embodiment the organic group has 1–10 carbons.

In a preferred aspect of the invention, each of $R^1$ and $R^2$ is hydrogen. These steroids not only have desirable biological activity, they also serve as convenient precursor compounds to preparing other steroid of the invention wherein $R^1$ and/or $R^2$ is not hydrogen.

For example, in one embodiment, the invention provides a compound of formula (1) wherein: $R^1$ and $R^2$ are hydrogen; $R^3$ and $R^4$ are selected from direct bonds to 6 and 7 respectively so as to form carbonyl groups, hydrogen, or a protecting group such that $R^3$ and/or $R^4$ is part of hydroxyl or carbonyl protecting group; and in addition to the —O$R^3$ and —O$R^4$ groups as shown, each of carbons 6 and 7 is substituted with hydrogen unless precluded because —O$R^3$ or —O$R^4$ represent a carbonyl group; carbons at numerals 1, 2, 4, 11, 12, 15 and 16 are each substituted with two hydrogens; carbons at numerals 5, 8, 9 and 14 are each substituted with one hydrogen; carbon at numeral 10 is substituted with methyl; carbon at number 13 is substituted with methyl unless it is part of an unsaturated bond; carbon at numeral 17 is substituted with (a) one of: =O, =C($R^5$)($R^5$), =C=C($R^5$)($R^5$), —C($R^5$)($R^5$)(C($R^5$)($R^5$))$_n$— and —(O(C($R^5$)($R^5$))$_n$O)— wherein n ranges from 1 to about 6; or (b) two of the following, which are independently selected: —X, —N($R^1$)($R^2$), —$R^5$ and —O$R^6$; each of rings A, B, C and D is independently fully saturated, partially saturated or fully unsaturated; $R^5$ at each occurrence is independently selected from H, X, and $C_{1-30}$ organic moiety that may optionally contain at least one heteroatom selected from the group consisting of boron, halogen, nitrogen, oxygen, silicon and sulfur; where two geminal $R^5$ groups may together form a ring with the carbon atom to which they are both bonded; $R^6$ is H or a protecting group such that —O$R^6$ is a protected hydroxyl group, where vicinal —O$R^6$ groups may together form a cyclic structure that protects vicinal hydroxyl groups, and where geminal —O$R^6$ groups may together form a cyclic structure that protects a carbonyl group; and X represents fluoride, chloride, bromide and iodide.

In another one embodiment, the invention provides a compound of formula (1) wherein: $R^1$ and $R^2$ are hydrogen; $R^3$ and $R^4$ are selected from hydrogen and protecting groups such that $R^3$ and/or $R^4$ is part of hydroxyl protecting group; carbons at numerals 1, 2, 4, 11, 12, 15 and 16 are each substituted with two hydrogens; carbons at numerals 5, 8, 9 and 14 are each substituted with one hydrogen; carbon at numeral 10 is substituted with methyl; carbon at number 13 is substituted with methyl unless it is part of an unsaturated bond; carbon at numeral 17 is substituted with (a) one of: =C($R^5$)($R^5$) and =C=C($R^5$)($R^5$); or (b) two of the following, which are independently selected: —X, —N($R^1$)($R^2$), and —$R^5$; each of rings A, B, C and D is independently fully saturated or partially saturated; $R^5$ at each occurrence is independently selected from H, X, and $C_{1-30}$ hydrocarbons, halocarbons and halohydrocarbons; and X represents fluoride, chloride, bromide and iodide.

In another one embodiment, the invention provides a compound of formula (1) wherein: $R^1$ and $R^2$ are hydrogen; $R^3$ and $R^4$ are selected from hydrogen and protecting groups such that $R^3$ and/or $R^4$ is part of hydroxyl protecting group; carbons at numerals 1, 2, 4, 11, 12, 15 and 16 are each substituted with two hydrogens; carbons at numerals 5, 8, 9 and 14 are each substituted with one hydrogen; carbon at numeral 10 is substituted with methyl; carbon at number 13 is substituted with methyl unless it is part of an unsaturated bond; carbon at numeral 17 is substituted with (a) one of: =C($R^5$)($R^5$) and =C=C($R^5$)($R^5$); or (b) two of —$R^5$; each of rings A, B, C and D is independently fully saturated or partially saturated; and $R^5$ at each occurrence is independently selected from H and $C_{1-10}$ hydrocarbons.

Specific compounds of the present invention wherein $R^1$ and $R^2$ are hydrogen include:

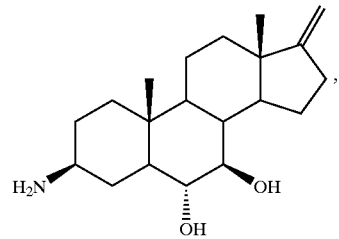

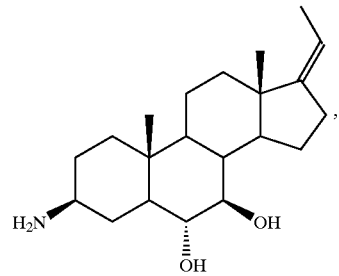

-continued

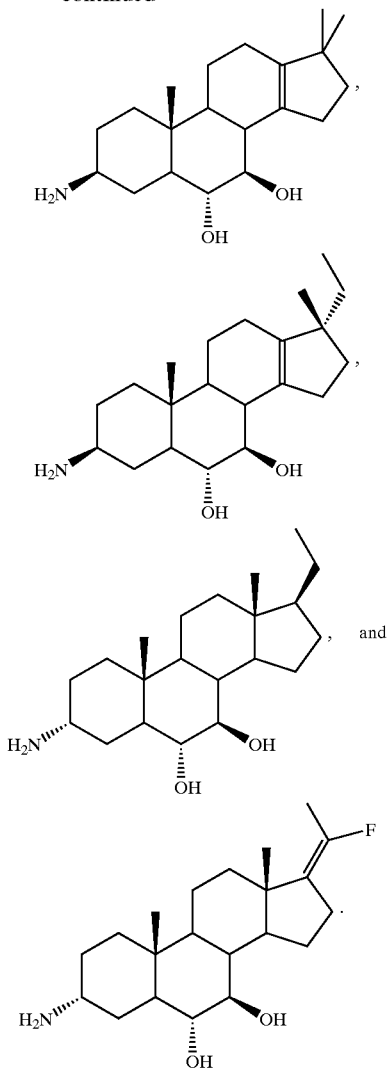

In another aspect, the invention provides steroids having 3-nitrogen substitution, where the 3-nitrogen is substituted with an organic group. For instance, the invention provides steroid compounds wherein $R^1$ is selected from —C(=O)—$R^7$, —C(=O)NH—$R^7$; and —$SO_2$—$R^7$; wherein $R^7$ is selected from alkyl, heteroalkyl, aryl and heteroaryl groups. In a related embodiment, $R^1$ is hydrogen and $R^2$ is —$CH_2$—R wherein $R^7$ is selected from alkyl, heteroalkyl, aryl and heteroaryl. In one embodiment, $R^7$ is selected from $C_{1-10}$hydrocarbyl. In another embodiment, —C(=O)—$R^7$ comprises biotin. In another embodiment, $R^7$ is selected from alkyl-substituted phenyl; halogen-substituted phenyl; alkoxy-substituted phenyl; aryloxy-substituted phenyl; and nitro-substituted phenyl.

In another aspect, $(R^1)(R^2)N$— is a heterocycle, that is, the N of $(R^1)(R^2)N$— may be part of a heterocyclic ring. Examples include:

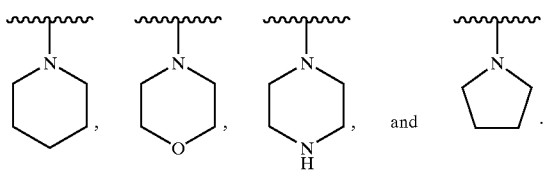

In another aspect, either or both of $R^1$ and $R^2$ comprises a heterocyclic ring or a carbocyclic ring. A preferred heterocyclic ring is

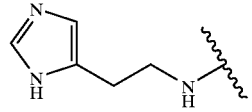

and a preferred carbocyclic ring is phenyl, which includes substituted phenyl such as 3-methylphenyl; 4-hydroxyphenyl; and 4-sulfonamidephenyl.

In another aspect, $R^1$ may be a 2, or 3 atom chain to numeral 2 so that —N—$R^1$— forms part of a fused bicyclic structure to ring A. Thus, the present invention provides compounds of the formula shown below, where Z represents 2 or 3 atoms, selected from C, N and O. The ring including Z may be saturated or unsaturated.

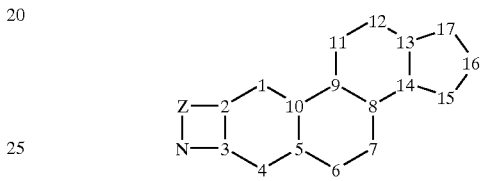

Examples of such fused ring compounds include:

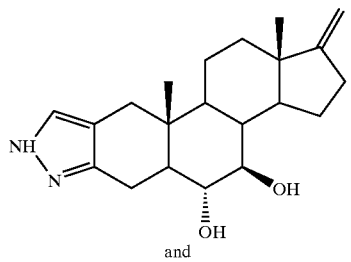

and

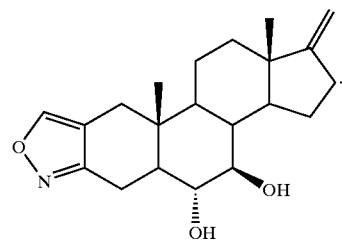

In another aspect, $R^1$ is hydrogen and $R^2$ comprises a $C_{1-10}$hydrocarbyl.

In another aspect, $R^1$ is hydrogen and $R^2$ is heteroalkyl. Suitable heteroalkyl include, without limitation, $C_{1-10}$alkyl-W—$C_{1-10}$alkylene- wherein W is selected from O and NH; HO—$C_{1-10}$alkylene-; and HO—$C_{1-10}$alkylene-W—$C_{1-10}$alkylene- where W is selected from O and NH.

In another aspect, each of $R^1$ and $R^2$ is independently selected from hydrogen and organic groups having 1–20 carbons and optionally containing 1–5 heteroatoms selected from nitrogen, oxygen, silicon, and sulfur.

In another aspect, each of $R^1$ and $R^2$ is independently selected from hydrogen, $R^8$, $R^9$, $R^{10}$, $R^{11}$ and $R^{12}$ where $R^8$ is selected from $C_{1-10}$alkyl, $C_{1-10}$heteroalkyl comprising 1, 2 or 3 heteroatoms, $C_{6-10}$aryl and $C_{3-15}$heteroaryl comprising 1, 2 or 3 heteroatoms; $R^9$ is selected from $(R^8)_r$—$C_{1-10}$alkylene, $(R^8)_r$—$C_{1-10}$heteroalkylene comprising 1, 2 or 3 heteroatoms, $(R^8)_r$—$C_{6-10}$arylene and $(R^8)_r$—$C_{3-15}$heteroarylene comprising 1, 2 or 3 heteroatoms; $R^{10}$ is selected from $(R^9)_r$—$C_{1-10}$alkylene, $(R^9)_r$—$C_{1-10}$heteroalkylene comprising 1, 2 or 3 heteroatoms, $(R^9)_r$—$C_{6-10}$arylene, and $(R^9)_r$—$C_{3-15}$heteroarylene comprising 1, 2 or 3 heteroatoms; $R^{11}$ is selected from $(R^{10})_r$—$C_{1-10}$alkylene, $(R^{10})_r$—$C_{1-10}$heteroalkylene comprising 1, 2 or 3 heteroatoms, $(R^{10})_r$—$C_{6-10}$arylene, and $(R^{10})_r$—$C_{3-15}$heteroarylene comprising 1, 2 or 3 heteroatoms, $R^{12}$ is selected from $(R^{11})_r$—$C_{1-10}$alkylene, $(R^{11})_r$—$C_{1-10}$heteroalkylene comprising 1, 2 or 3 heteroatoms, $(R^{11})_r$—$C_{6-10}$arylene, and $(R^{11})_r$—$C_{3-15}$heteroarylene comprising 1, 2 or 3 heteroatoms, and r is selected from 0, 1, 2, 3, 4 and 5, with the proviso that $R^1$ and $R^2$ may join to a common atom so as to form a ring with the common atom.

In another aspect, the present invention provides steroid compounds of the structure shown above, wherein: $R^1$ and $R^2$ are independently selected from hydrogen, $R^8$, $R^9$, $R^{10}$, $R^{11}$ and $R^{12}$ where $R^8$ is selected from alkyl, heteroalkyl, aryl and heteroaryl; $R^9$ is selected from $(R^8)_r$-alkylene, $(R^8)_r$-heteroalkylene, $(R^8)_r$-arylene and $(R^8)_r$-heteroarylene; $R^{10}$ is selected from $(R^9)_r$-alkylene, $(R^9)_r$-heteroalkylene, $(R^9)_r$-arylene, and $(R^9)_r$-heteroarylene; $R^{11}$ is selected from $(R^{10})_r$-alkylene, $(R^{10})_r$-heteroalkylene, $(R^{10})_r$-arylene, and $(R^{10})_r$-heteroarylene, $R^{12}$ is selected from $(R^{11})_r$-alkylene, $(R^{11})_r$-heteroalkylene, $(R^{11})_r$-arylene, and $(R^{11})_r$-heteroarylene, and r is selected from 0, 1, 2, 3, 4 and 5, with the proviso that $R^1$ and $R^2$ may join to a common atom so as to form a ring with the common atom; $R^3$ and $R^4$ are selected from hydrogen and protecting groups such that $R^3$ and/or $R^4$ is part of hydroxyl protecting group; carbons at numerals 1, 2, 4, 11, 12, 15 and 16 are each substituted with two hydrogens; carbons at numerals 5, 8, 9 and 14 are each substituted with one hydrogen; carbon at numeral 10 is substituted with methyl; carbon at number 13 is substituted with methyl unless it is part of an unsaturated bond; carbon at numeral 17 is substituted with (a) one of: $=C(R^5)(R^5)$ and $=C=C(R^5)(R^5)$; or (b) two of —$R^5$; each of rings A, B, C and D is independently fully saturated or partially saturated; and $R^5$ at each occurrence is independently selected from H and $C_{1-10}$ hydrocarbons.

For instance, $R^1$ and $R^2$ are selected from hydrogen, $CH_3$—, $CH_3(CH_2)_2$—, $CH_3(CH_2)_4$—, $CH_3CO$—, $C_6H_5CO$—$(CH_3)_2CHSO_2$—, $C_6H_5SO_2$—, $C_6H_5NHCO$—, $CH_3(CH_2)_2NHCO$—, $CH_3(CH_2)_2NH(CH_2)_2$—, $(CH_3)_2N(CH_2)_2$—, $HOCH_2CH_2$—, $HOCH_2(CH_2)_4$—, $HOCH_2CH_2NHCH_2CH_2$—, 3-$(CH_3)C_6H_4$—, 4-$(HO)C_6H_4$—, 4-$(H_2NSO_2)C_6H_4$—, 4-$((CH_3)_2CH)C_6H_4$—$CH_2$—, 2-$(F)C_6H_4$—$CH_2$—, 3-$(CF_3)C_6H_4$—$CH_2$—, 2-$(CH_3O)C_6H_4$—$CH_2$—, 4-$(CF_3O)C_6H_4$—$CH_2$—, 3-$(C_6H_5O)C_6H_4$—$CH_2$—, 3-$(NO_2)C_6H_4$—$CH_2$—,

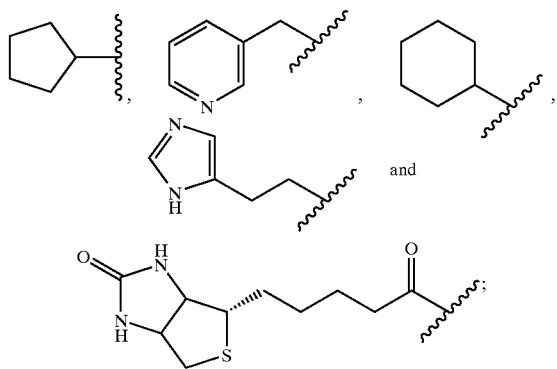

or $R^1$ and $R^2$ may join together with the nitrogen to which they are both attached and form a heterocycle selected from:

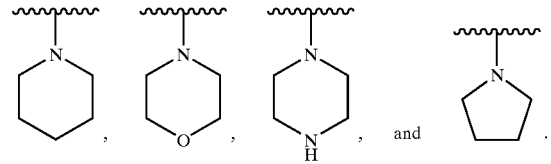

Specific compounds of the present invention wherein $R^1$ is hydrogen but $R^2$ is not hydrogen include:

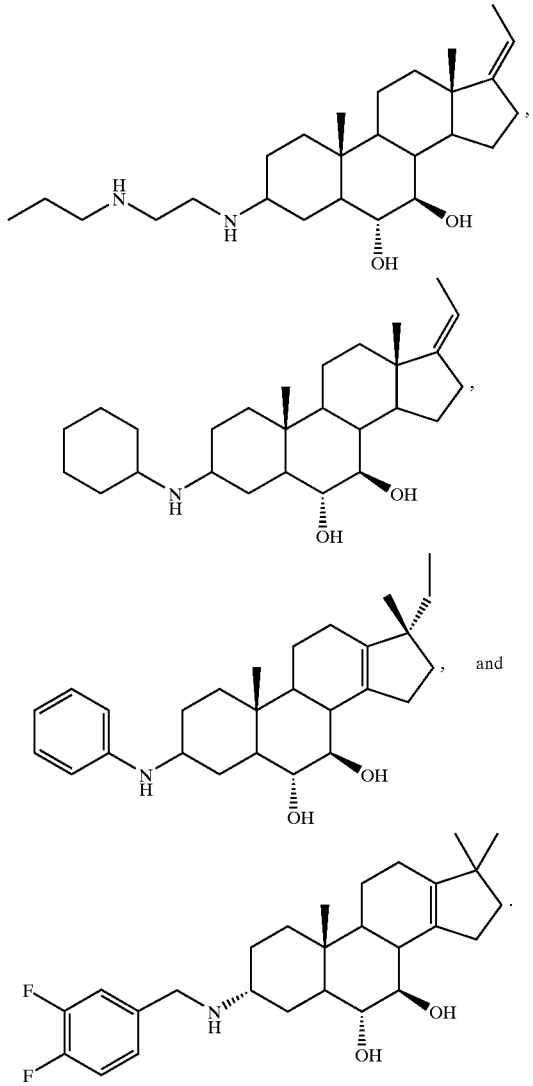

Thus, one set of preferred compounds of the invention have $R^1$ equal to hydrogen but $R^2$ is not equal to hydrogen.

In steroid compounds of the invention as disclosed above, in one aspect each of $R^3$ and $R^4$ is hydrogen, i.e., the steroid has hydroxy substitution at each of the carbons located at numerals 6 and 7. In a related aspect, one or both of the hydroxy groups at carbons 6 and 7 are in a protected form, i.e., are bonded to a hydroxy protecting group. Such protecting groups are well known in the art, and are disclosed in, e.g., Greene and Wuts, "Protective Groups in Organic Synthesis", John Wiley & Sons, New York, N.Y. (1999). A suitable protecting group is a ketal, so that the present invention provides compounds of the structure:

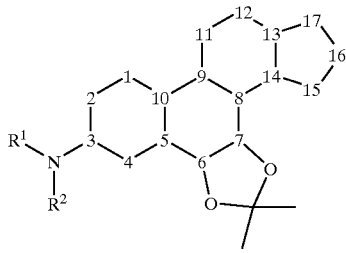

As stated above, the present invention provides steroid compounds that include compounds of defined stereochemistry. One such compound has the stereochemistry shown in the following structure for $R^3O$— and $R^4O$—:

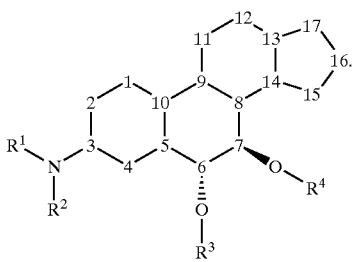

As also stated above, the present invention provides salt forms of the steroids of the present invention, preferably pharmaceutically acceptable salts. In one embodiment, $—N(R^1)(R^2)$ is in a salt form. In other words, $—N(R^1)(R^2)$ is protonated so that the N carries a positive charge. In such a case, the steroid compound of the present invention is an acid addition salt as defined herein. In a preferred aspect, the present invention provides hydrochloride salts of the steroid structures shown above. In another preferred aspect, the present invention provides acetate salts of the steroid structures shown herein.

As also stated above, the present invention provides prodrugs of the specific compounds shown by formula (1). In one aspect, the present invention is directed to a prodrug of any of the specific compounds shown by formula (1). In another aspect, the present invention excludes prodrugs of the specific compounds shown by formula (1), i.e., in one aspect the present invention is directed to compounds of formula (1) and pharmaceutically acceptable salts, solvates, stereoisomers but not prodrugs thereof, in isolation or in mixture.

In steroid compounds of the invention as set forth above, in a preferred embodiment, 17 is substituted with $=C(R^5)(R^5)$ and $R^5$ is selected from hydrogen, halogen, $C_{1-6}$alkyl, $C_{1-6}$ hydroxyalkyl, and $—CO_2—C_{1-6}$alkyl. In other preferred embodiment, 17 is substituted with $C_{1-6}$alkyl or $C_{1-6}$haloalkyl; or 17 is substituted with $—OR^6$ or $=O$, wherein $R^6$ is hydrogen.

In steroid compounds of the invention as set forth herein, in a preferred embodiment, at least one of 10 and 13 is substituted with methyl.

In steroid compounds of the invention as set forth herein, in a preferred embodiment, numerals 1 through 16 each represent a carbon, where carbons at numerals 1, 2, 4, 11, 12, 15 and 16 may be independently substituted with: (a) one of: $=O$, $=C(R^5)(R^5)$, $=C=C(R^5)(R^5)$, $—C(R^5)(R^5)(C(R^5)(R^5))_n$— and $—(O(C(R^5)(R^5))_nO)$— wherein n ranges from 1 to about 6; or (b) two of the following, which are independently selected: $—X$, $—N(R^1)(R^2)$, $—R^5$ and $—OR^6$; and numeral 17 represents a carbon substituted with: (a) one of: $=C(R^{5a})(R^{5a})$, $=C=C(R^{5a})(R^{5a})$, and $—C(R^{5a})(R^{5a})(C(R^{5a})(R^{5a}))_n$— wherein n ranges from 1 to about 6; or (b) two of the following, which are independently selected: $—X$, $—N(R^1)(R^2)$, and $—R^{5a}$; where $R^{5a}$ at each occurrence is independently selected from H, X, and $C_{1-30}$ organic moiety that may optionally contain at least one heteroatom selected from the group consisting of boron, halogen, nitrogen, silicon and sulfur; where two geminal $R^5$ groups may together form a ring with the carbon atom to which they are both bonded. Optionally, $R^{5a}$ at each occurrence is independently selected from $C_{1-30}$ hydrocarbon, $C_{1-30}$ halocarbon, $C_{1-30}$ hydrohalocarbon, H, and X. In an alternative optional embodiment, $R^{5a}$ at each occurrence is independently selected from $C_{1-10}$ hydrocarbon, $C_{1-10}$ halocarbon, $C_{1-10}$ hydrohalocarbon, H, and X. Optionally, in each of these listed embodiment, the present invention provides a further embodiment wherein $R^1$ and $R^2$ are selected from hydrogen, oxygen so as to form nitro or oxime, amino, $—SO_3—R$, and organic groups having 1–30 carbons and optionally containing 1–6 heteroatoms selected from oxygen, phosphorous, silicon, and sulfur, where $R^2$ may be a direct bond to numeral 3, or $R^1$ and $R^2$ may, together with the N to which they are both bonded, form a heterocyclic structure that may be part of an organic group having 1–30 carbons and optionally containing 1–6 heteroatoms selected from oxygen and silicon; or $R^1$ may be a 2 or 3 atom chain to numeral 2 so that $—N—R^1$— forms part of a fused bicyclic structure to ring A. Optionally, in each of these listed embodiments, the present invention provides a further embodiment wherein carbons at numerals 1, 2, 4, 11, 12, 15 and 16 are each substituted with two hydrogens unless said carbon is part of an unsaturated bond; carbons at numerals 5, 8, 9 and 14 are each substituted with one hydrogen unless said carbon is part of an unsaturated bond; carbon at numeral 10 is substituted with methyl; and carbon at number 13 is substituted with methyl unless it is part of an unsaturated bond. Optionally, in each of these listed embodiments, the present invention provides a further embodiment wherein carbons at numerals 1, 2, 4, 11, 12, 15 and 16 are each substituted with two hydrogens; carbons at numerals 5, 8, 9 and 14 are each substituted with one hydrogen; carbon at numeral 10 is substituted with methyl; and carbon at number 13 is substituted with methyl unless it is part of an unsaturated bond.

In steroid compounds of the invention as set forth herein, in a preferred embodiment, each of $R^1$ and $R^2$ is hydrogen; and/or each of $R^3$ and $R^4$ is hydrogen; and/or the carbon at numeral 17 is substituted with (a) one of the following: $C(R^{5a})(R^{5a})$, $=C=C(R^{5a})(R^{5a})$, and $—C(R^{5a})(R^{5a})(C(R^{5a})(R^{5a}))_n$— wherein n ranges from 1 to about 6; or (b) two of the following, which are independently selected: $—X$, $—N(R^1)(R^2)$, and $—R^{5a}$; where $R^{5a}$ at each occurrence is independently selected from H, X, and $C_{1-30}$ organic moiety that may optionally contain at least one heteroatom selected from the group consisting of boron, halogen, nitrogen, silicon and sulfur; where two geminal $R^5$ groups may together form a ring with the carbon atom to which they are both bonded.

In steroids of the present invention, unless otherwise indicated, each of rings A, B, C and D is independently fully saturated, partially saturated or fully unsaturated. That is, hydrogens attached to any of the carbons at positions 1–17 may be omitted so as to allow unsaturation within the A, B, C and/or D ring. For example, when carbons at numerals 5, 8, 9 and 14 are indicated as being substituted with one hydrogen, and it is also indicated that each of rings A, B, C and D is independently fully saturated, partially saturated or fully unsaturated, then any one or more of the hydrogens attached to carbons at numerals 5, 8, 9 and 14 may be omitted in order to allow unsaturation at the carbon atom.

The compounds of the present invention are intended as pharmaceutical agents. Preferably, the molecular weight of a compound of the invention is relatively small, that is, less than about 5,000 g/mol, typically less than 4,000 g/mol, more typically less than 3,000 g/mol, still more typically less than 2,000 g/mol, yet more typically less than 1,000 g/mol, where the minimum molecular weight of a compound of the invention is about 300 g/mol, and each of these typical ranges is a separate embodiment of the present invention.

The steroid compounds of the present invention include pharmaceutically acceptable salts, solvates, stereoisomers and prodrugs of the 3-nitrogen-6,7-dioxygenated steroid structures described above, in isolation or in mixtures with one another.

The steroid compounds of the invention may, and typically do, exist as solids, including crystalline solids which can be crystallized from common solvents such as ethanol, N,N-dimethyl-formamide, water, or the like. The crystallization process may, depending on the crystallization conditions, provide various polymorphic structures. Typically, a more thermodynamically stable polymorph is advantageous to the commercial scale manufacture of a steroid compound of the invention, and is a preferred form of the compound.

Often, crystallizations produce a solvate of the steroid compound having the structure shown above. As used herein, the term "solvate" refers to an aggregate that comprises one or more 3-nitrogen-6,7-dioxygenated steroid compounds of the invention, with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The steroid compounds may be true solvates, while in other cases, the steroid may merely retain adventitious water or be a mixture of water plus some adventitious solvent.

As used herein, a "pharmaceutically acceptable solvate" refers to a solvate that retains the biological effectiveness and properties of the biologically active 3-nitrogen-6,7-dioxygenated steroid compounds of the invention. Examples of pharmaceutically acceptable solvates include, but are not limited to, water, isopropanol, ethanol, methanol, DMSO, ethyl acetate, acetic acid, and ethanolamine. It should be appreciated by those skilled in the art that solvated forms are equivalent to unsolvated forms and are intended to be encompassed within the scope of the present invention. Sykes, P. A., Guidebook to Mechanism in Organic Chemistry, 6th Ed (1986, John Wiley & Sons, N.Y.) is an exemplary reference that describe solvates.

The inventive compounds may exist as single stereoisomers, racemates and/or mixtures of enantiomers and/or diastereomers. All such single stereoisomers, racemates and mixtures thereof are intended to be within the scope of the present invention. In a preferred aspect, the inventive compounds are used in optically pure form.

A "pharmaceutically acceptable prodrug" is intended to mean a compound that may be converted under physiological conditions or by solvolysis to a biologically active 3-nitrogen-6,7-dioxygenated steroid compound as described above. Thus, the term "prodrug" refers to a metabolic precursor of a steroid compound of the present invention that is pharmaceutically acceptable. A prodrug may be inactive when administered to a subject but is converted in vivo to an active 3-nitrogen-6,7-dioxygenated steroid compound of the invention. Prodrugs are typically rapidly transformed in vivo to yield the parent compound of the above formulae, for example, by hydrolysis in blood.

A discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference. A typical prodrug is a derivative of the steroid compounds of the invention which have chemically or metabolically cleavable groups and become, by solvolysis or under physiological conditions, the compounds of the invention which are pharmaceutically active in vivo. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). A preferred prodrug is a compound having substitution at the 3-nitrogen atom of the steroids of the invention, where the substitution is cleaved in vivo to provide a pharmaceutically active compound.

Steroids of the present invention having C3 nitrogen substitution and oxygen substitution at positions 6 and 7 have unexpected properties that enhance the efficacies of these compounds. For instance, the steroid of the present invention have an excellent metabolic stability in S9 fractions from human liver. For example, 100% of compounds 28, 89, 139, and 143 remains unchanged after 15 and even 30 minutes incubation with human S9 fractions. It was an unexpected finding that C3 nitrogen substitutions significantly decrease glucuronidation of the molecules in plasma. In addition, steroids of the present invention having C3 nitrogen substitutions such as compounds 28, 89 and 83 are highly soluble in aqueous solution, demonstrating a solubility of >100 mg/ml in water. Furthermore, the potency and pharmacokinetic profile of steroids of the present invention with C3 nitrogen substitutions is highly suitable for therapeutic application. Doses of <1.0 mg/kg once per day reproducibly demonstrate significant anti-inflammatory activity in in vivo inflammation models. In the rat, compounds 28 and 89 have an average half-life of 7.5 hours and an oral bioavailability of ~100%, while in the monkey, the half-life averages 15 hours and oral bioavailability is 25–30%. The maximal concentration in plasma in both species is predictable and linear.

C. Preparation of Compounds

The compounds according to the present invention can be prepared by methods employing steps known to those skilled in the art or analogous to those steps. General methods for the reactions on steroids can be found in "Steroid Reactions", C. Djerassi, Ed. Holden Day, San Francisco, Calif., 1963 and references cited therein. General synthetic methods can be found in "Comprehensive Organic Transformations", R. C. Larock, VCH Publishers, New York, N.Y., 1989 and references cited therein. Additional literature references useful for the synthesis of compounds of the invention are as follows: T. Reichstein; C. H. Meystre, *Helv. Chim. Acta,* 1932, 22, 728; H. Westmijze; H. Kleyn; P. Vermeer; L. A. van Dijck, *Tet. Lett.* 1980, 21, 2665; K. Prezewowsky; R Wiechert, U.S. Pat. No. 3,682,983; P. Kaspar; H. Witzel, *J. Steroid Biochem.* 1985, 23, 259; W. G. Dauben; T. Brookhart, *J. Am. Chem. Soc.* 1981, 103, 237; A. J. Manson et al., *J. Med. Chem.* 1963, 6, 1; R. O. Clinton et al, *J. Am. Chem. Soc.* 1961, 83, 1478; and J. A. Zderic et al. *Chem. and Ind.* 1960, 1625.

In a preferred method, C3, C6, C7 and C17 polyoxygenated steroids are used as starting materials or intermediates. Methods to introduce C6 and C7 oxygens into commercially available starting materials are described in U.S. Pat. No. 6,046,185. This U.S. Patent also discloses many ways in which substitution and preferred stereochemistry can be introduced into positions C1, C2, C4, C5, C8, C9, C10, C11, C12, C13, C14, C15, C16 and C17. In the present invention, the C6 and C7 oxygens may be present as hydroxyls or as protected hydroxyls. The 6- and 7-hydroxyls can be protected individually or they can together be part of a ring. Suitable protecting groups are listed in Greene and Wuts, "Protective Groups in Organic Synthesis", John Wiley & Sons, New York, N.Y. (1999).

Referring to Scheme A, ketones of compound 2, or compounds analogous thereto, can be alkylated with a variety of alkylating groups to give steroids of the invention having but not limited to, alkyl, cycloalkyl, aryl, and heteroaryl substitution. For example, alkylation of the 17-ketone 2, with the anion of acetylene generates the 17α-ethynyl-17β-hydroxyl intermediate 3. Reversal of the stereochemistry of the C17 substituents may be carried out by first forming the methylsulfonate followed by treatment with silver (I) nitrate in tetrahydrofuran (THF) and water. Dehydration of compound 3 using $POCl_3$ in 2,4-lutidine gives compound 4. Tetrabutylammonium fluoride in THF removes the tert-butyldimethylsilyl (TBS) protecting group from the 3-hydroxyl to give compound 5. Treatment of the 3α-hydroxyl compound 5 with $ZnN_6 \cdot 2py$, triphenylphosphine and diisopropyl azodicarboxylate (DIAD) in toluene gives the 3β-azido compound 6. The $ZnN_6 \cdot 2py$ is prepared by the reaction of $Zn(NO_3)_2$ and $NaN_3$ followed by treatment with pyridine according to the procedure of M. C. Viaud and P. Rollin in *Synthesis* 1990, 130. Lithium aluminum hydride reduction of the azide in diethyl ether ($Et_2O$) gives the amine 7. Treatment with HCl in THF and water removes the acetonide group and forms the ammonium chloride salt 8.

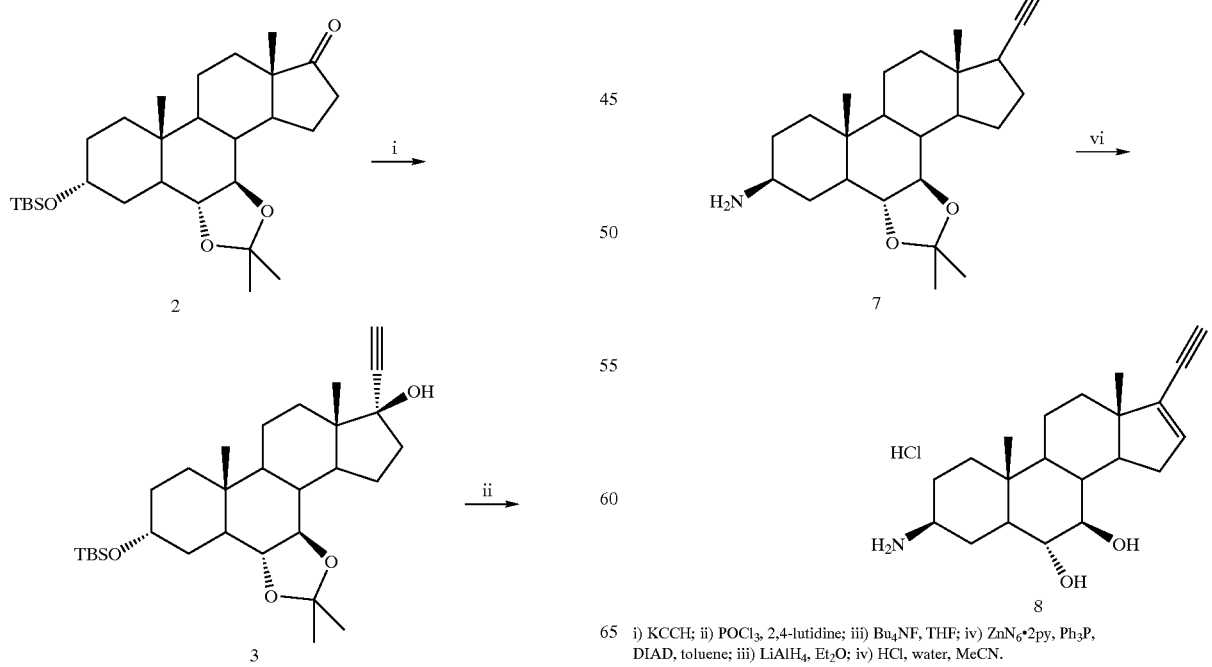

i) KCCH; ii) $POCl_3$, 2,4-lutidine; iii) $Bu_4NF$, THF; iv) $ZnN_6 \cdot 2py$, $Ph_3P$, DIAD, toluene; iii) $LiAlH_4$, $Et_2O$; iv) HCl, water, MeCN.

Referring to Scheme B, steroids of the invention having allene functionality may be prepared from intermediates analogous to compound 3. Exemplary is the reaction of compound 3 with LiAlH$_4$ and AlCl$_3$ in THF to give the allene 9. Tetrabutylammonium fluoride in THF removes the protecting group from the 3-hydroxyl to give compound 10. Treatment of the 3α-hydroxyl compound 10 with ZnN$_6$.2py, triphenylphosphine and DIAD in toluene gives the 3β-azido compound 11. Lithium aluminum hydride reduction of the azide 11 in Et$_2$O gives the amine 12. Treatment with HCl in THF and water removes the acetonide group and forms the ammonium chloride salt 13.

Scheme B

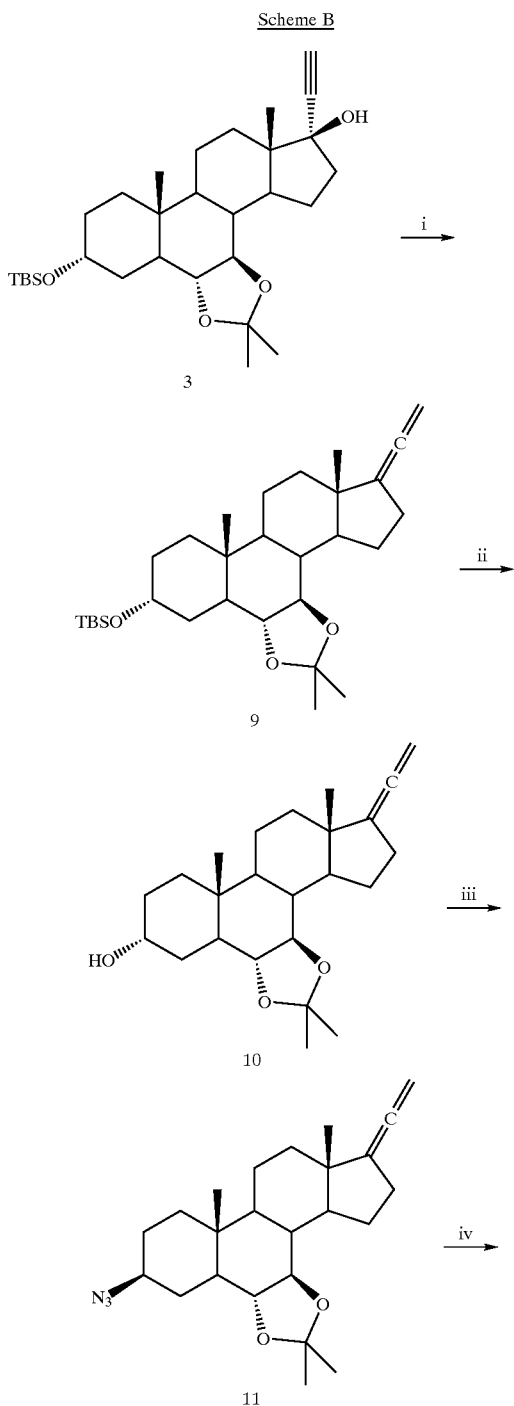

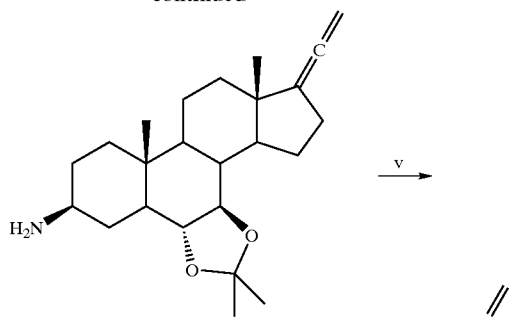

i) LiAlH$_4$, AlCl$_3$, THF; ii) Bu$_4$NF, THF; iii) ZnN$_6$•2py, Ph$_3$P, DIAD, toluene; iv) LiAlH$_4$, Et$_2$O; v) HCl, water, MeCN.

Referring to Scheme C, compounds of the invention having alkynyl functionality may be prepared from allene intermediates. Exemplary is the treatment of compound 9 with n-BuLi in THF giving the 17β-ethynyl compound 14. Tetrabutylammonium fluoride in THF removes the protecting group from the 3-hydroxyl to give compound 15. Treatment of the 3α-hydroxyl compound 15 with ZnN$_6$.2py, triphenylphosphine and DIAD in toluene gives the 3β-azido compound 16. Lithium aluminum hydride reduction of the azide 16 in Et$_2$O gives the amine 17. Treatment with HCl in THF and water removes the acetonide group and forms the ammonium chloride salt 18.

Scheme C

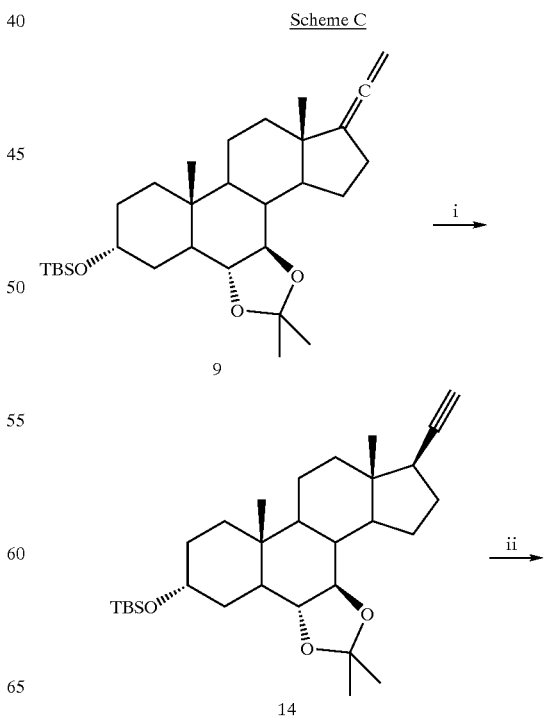

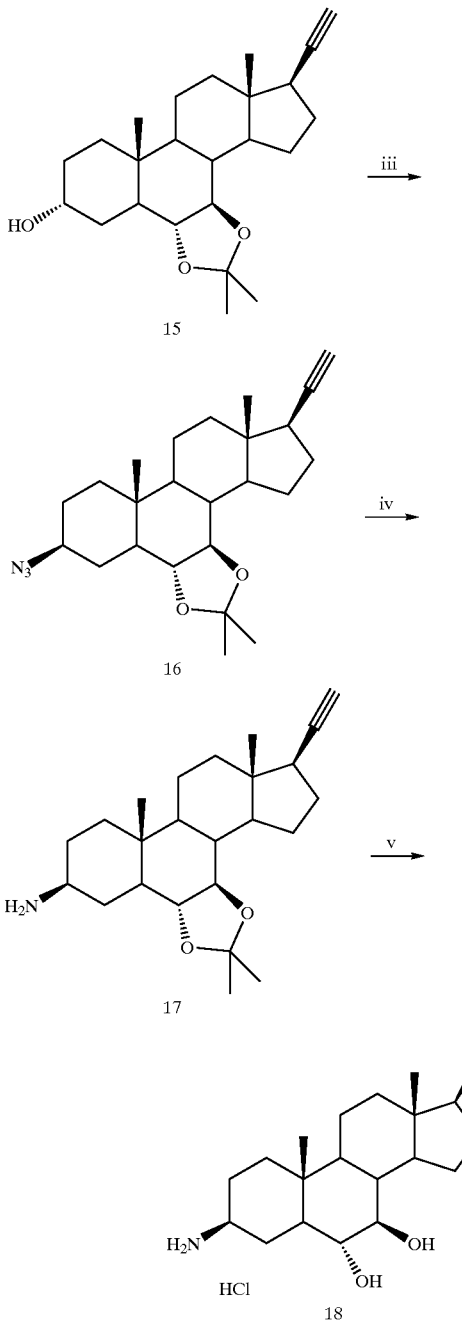

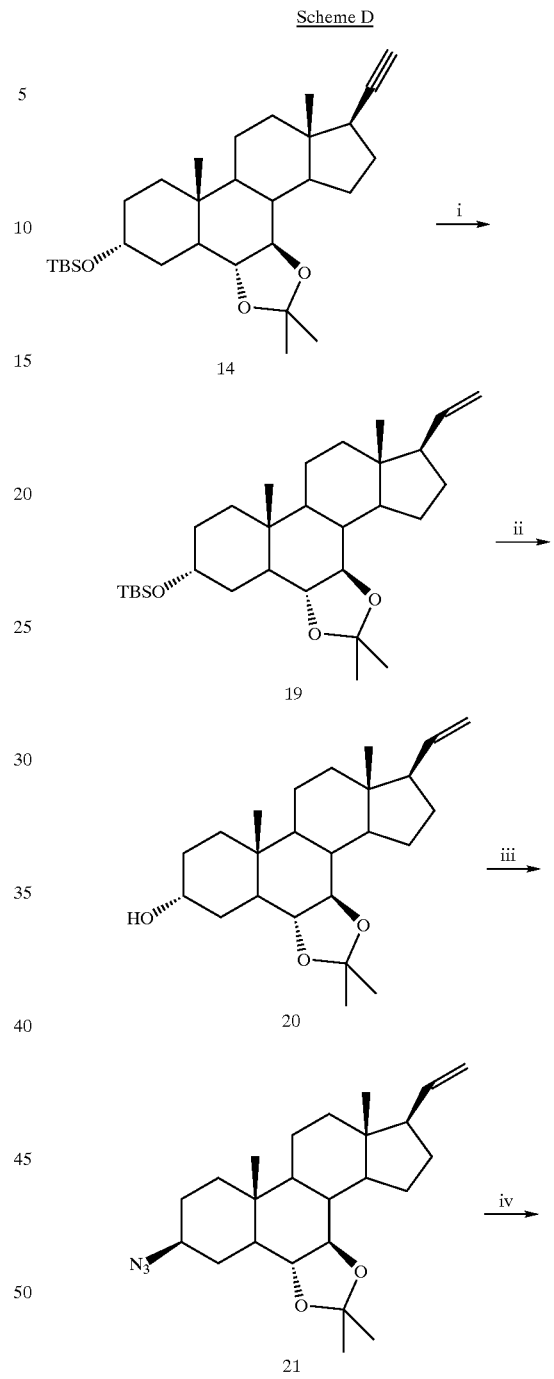

i) n-BuLi, THF; ii) Bu₄NF, THF; iii) ZnN₆·2py, Ph₃P, DIAD, toluene; iv) LiAlH₄, Et₂O; v) HCl, water, MeCN.

Referring to Scheme D, steroids of the invention having alkenyl functionality may be prepared from alkyne intermediates. Exemplary is the controlled hydrogenation of compound 14 using Pd—CaCO₃ as catalyst to give the alkene 19. Tetrabutylammonium fluoride in THF removes the protecting group from the 3-hydroxyl to give compound 20. Treatment of the 3α-hydroxyl compound 20 with ZnN₆·2py, triphenylphosphine and DIAD in toluene gives the 3β-azido compound 21. Lithium aluminum hydride reduction of the azide 21 in Et₂O gives the amine 22. Treatment with HCl in THF and water removes the acetonide group and forms the ammonium chloride salt 23.

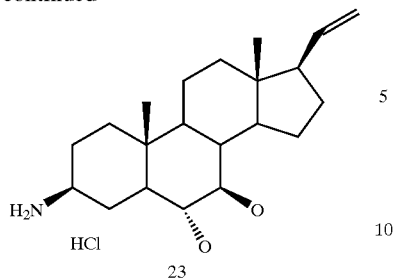

23 i) H$_2$, Pd—CaCO$_2$; ii) Bu$_4$NF, THF; iii) ZnN$_6$•2py, Ph$_3$P, DIAD, toluene; iv) LiAlH$_4$, Et$_2$O; v) HCl, water, MeCN.

Compound 2 can be used in a multitude of olefination reactions, including Wittig-type reactions to provide compounds of the invention having an exocyclic olefin at C17. For example, as illustrated in Scheme E, compound 2 may be treated with ethyltriphenylphosphonium bromide and potassium tert-butoxide (KO$^t$Bu) to provide compound 24 having R$_1$=methyl and R$_2$=hydrogen. Tetrabutylammonium fluoride in THF removes the protecting group from the 3-hydroxyl to give compound 25. Treatment of the 3α-hydroxyl compound 25 with ZnN$_6$.2py, triphenylphosphine and DIAD in toluene gives the 3β-azido compound 26. Lithium aluminum hydride reduction of the azide 26 in Et$_2$O gives the amine 27. Treatment with HCl in THF and water removes the acetonide group and forms the ammonium chloride salt 28 having R$_1$=methyl and R$_2$=hydrogen.

In analogy to the synthesis shown in Scheme E, ketones such as compound 2 may be reacted with other Wittig-type reagents such as, but not limited to, methyl-, propyl-, butyl-, pentyl-, or hexyltriphenylphosphonium bromide to give steroids of the invention analogous to compound 28 having R$_2$=hydrogen and R$_1$=hydrogen, ethyl, propyl, butyl or pentyl.

Scheme E

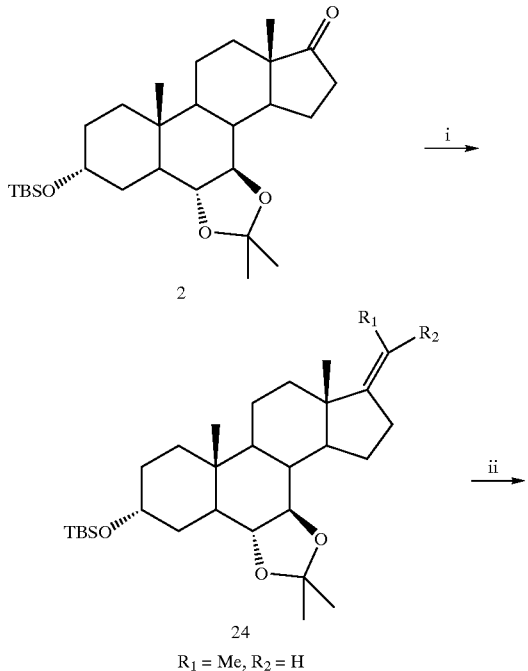

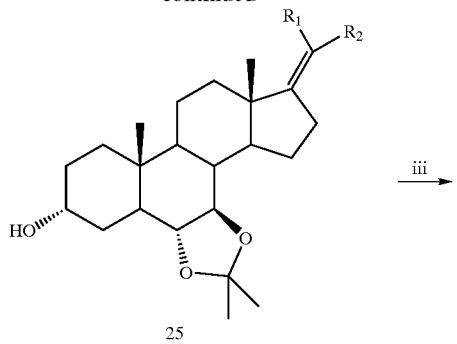

25
R$_1$ = Me, R$_2$ = H

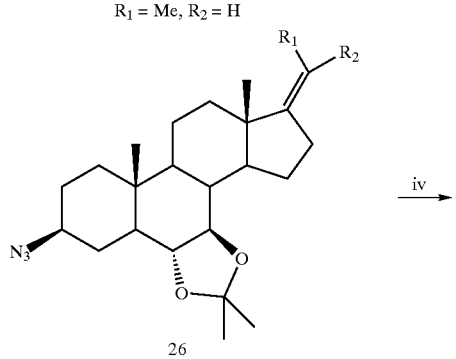

26
R$_1$ = Me, R$_2$ = H

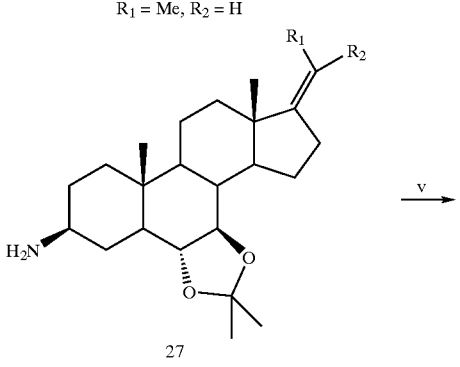

27
R$_1$ = Me, R$_2$ = H

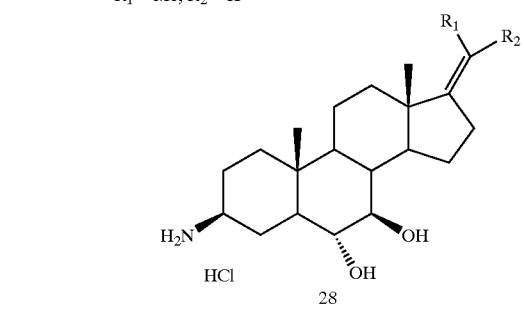

28
R$_1$ = Me, R$_2$ = H i) EtPPh$_3$Br, KO$^t$Bu, Toluene; ii) Bu$_4$NF, THF; iii) ZnN$_6$•2py, Ph$_3$P, DIAD toluene; iv) LiAlH$_4$, Et$_2$O; v) HCl, water, MeCN.

Steroids of the invention can contain exocyclic double bonds of E and/or Z geometry. For example, as illustrated in Scheme F, the Z-olefin 24 in cyclohexane may be treated with UV light in the presence of diphenyldisulfide resulting in isomerization to the E-olefin 29. Tetrabutylammonium fluoride in THF removes the protecting group from the 3-hydroxyl to give compound 30. Treatment of the 3α-hydroxyl compound 30 with ZnN$_6$.2py, triphenylphosphine and DIAD in toluene gives the 3β-azido compound 31. Lithium aluminum hydride reduction of the azide 31 in Et$_2$O gives the amine 32. Treatment with HCl in THF and water removes the acetonide group and forms the ammonium chloride salt 33.

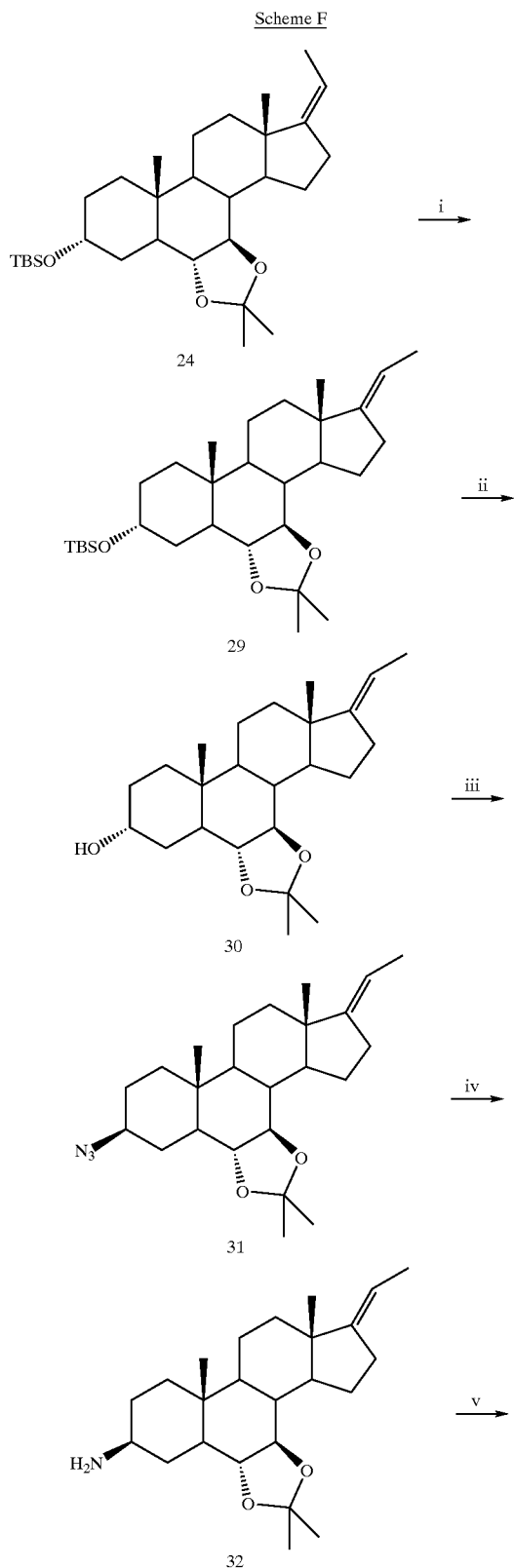

Scheme F

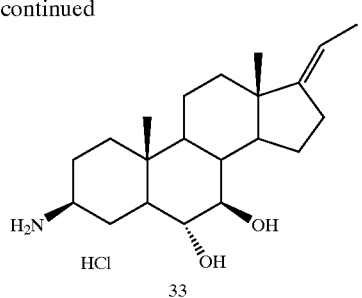

33 i) (PhS)$_2$, hv, cyclohexane; ii) Bu$_4$NF, THF; iii) ZnN$_6$·2py, Ph$_3$P, DIAD, toluene; iv) LiAlH$_4$, Et$_2$O; v) HCl, water, MeCN.

A multitude of steroids of the invention having functionalized sidechains can be prepared using methods such as Lewis acid promoted couplings to alkehydes and Michael acceptors. For example, as illustrated in Scheme G, compound 24 may be reacted with methyl propiolate in the presence of diethylaluminum chloride to give compound 34. The double bonds may be hydrogenated using a catalyst such as platinum to give compound 35. Tetrabutylammonium fluoride in THF removes the protecting group from the 3-hydroxyl to give compound 36. Treatment of the 3α-hydroxyl compound 36 with ZnN$_6$.2py, triphenylphosphine and DIAD in toluene gives the 3β-azido compound 37. Hydrogenation of the azide 37 using a palladium catalyst gives the amine 38. Treatment with HCl in THF and water removes the acetonide group and forms the ammonium chloride salt 39.

Scheme G

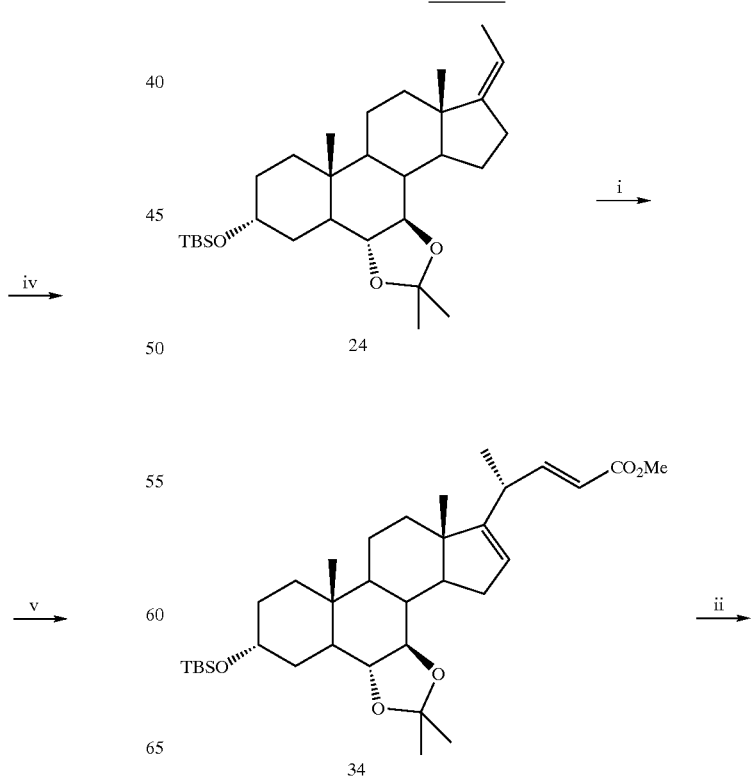

-continued

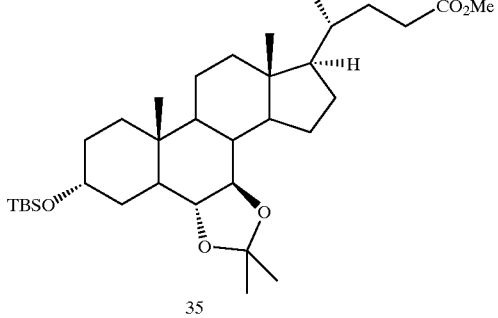

35

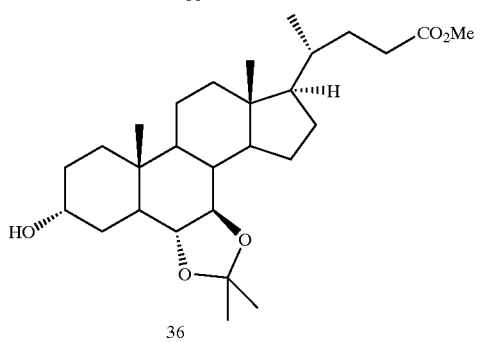

36

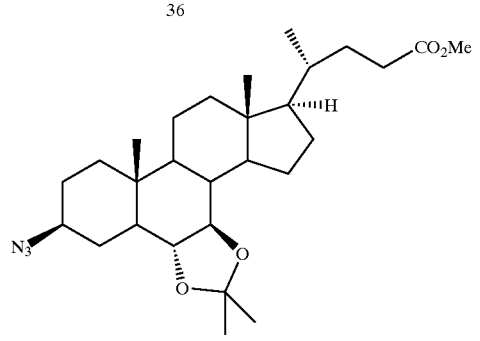

37

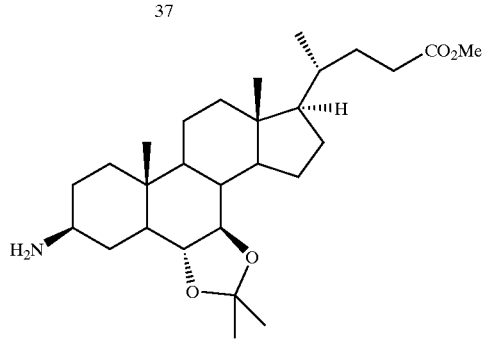

38

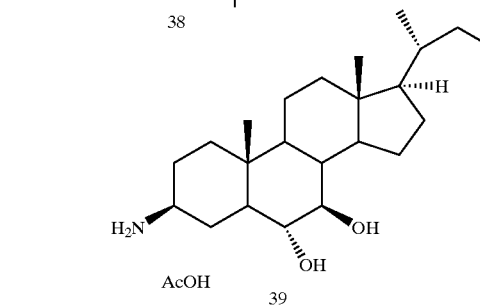

39 i) HCCCO2Me, Et2AlCl; ii) H2, Pt; iii) Bu4NF, THF; iv) ZnN6•2py, Ph3P, DIAD, toluene; v) H2, Pd, EtOAc; vi) 80% acetic acid.

Figure 1B:
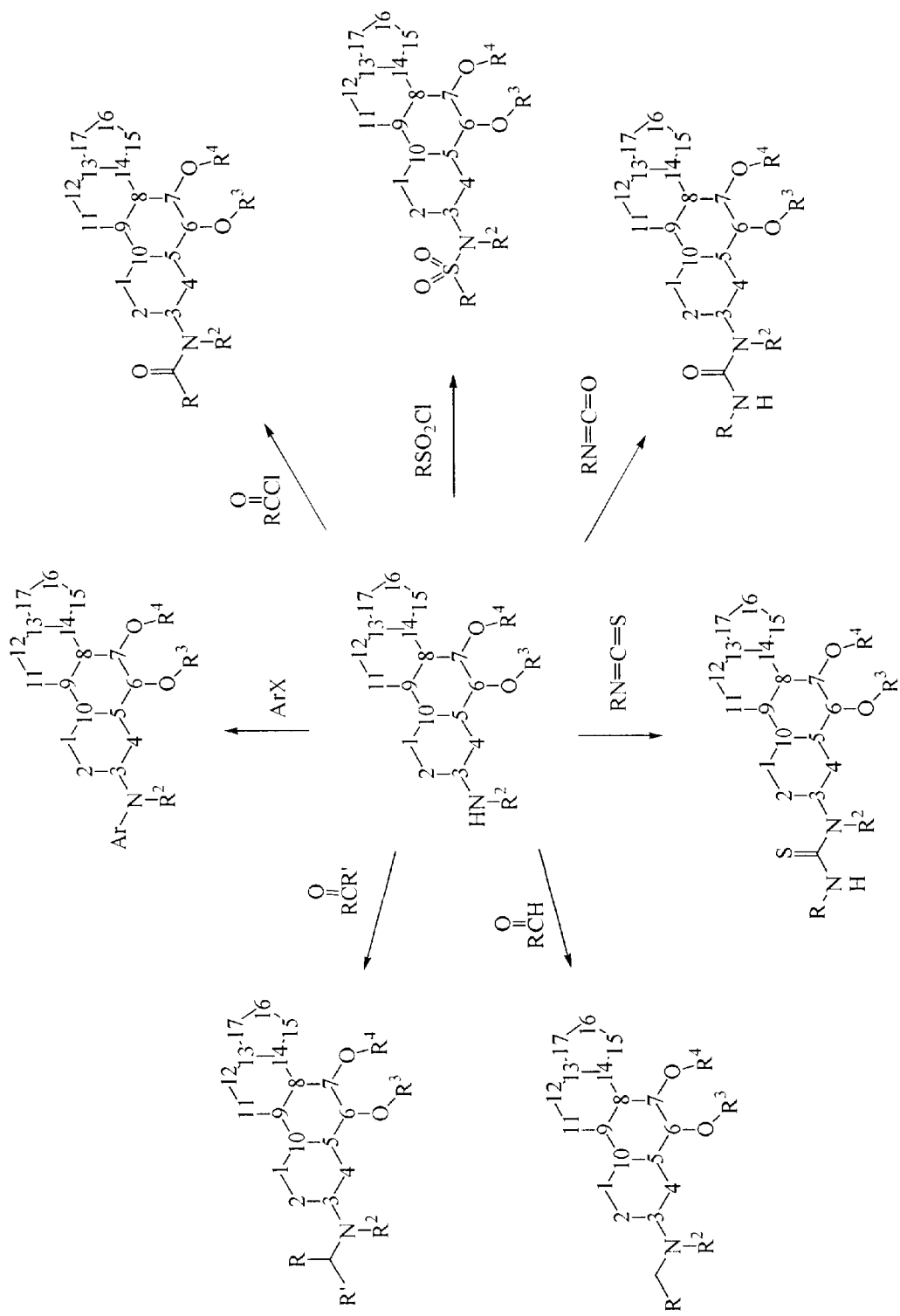
Figure 2A:
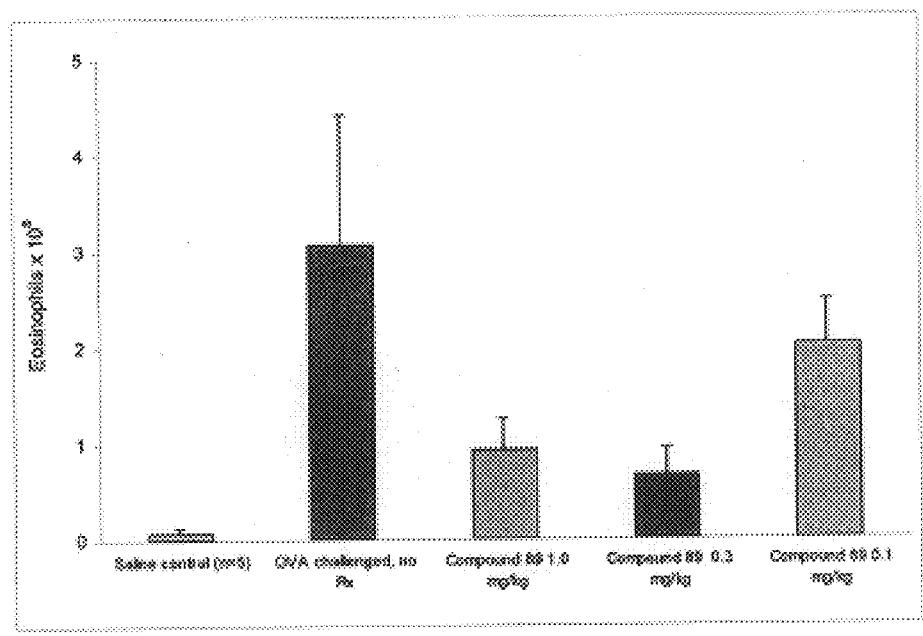
FIGS. 2A, 2B and 2C are a set of bar graphs showing the effect of compound 89 (dose response, 4 doses qd, p.o.) on ovalbumin-induced accumulation of inflammatory cells in the lung lavage fluid obtained from sensitized Brown Norway rats.
Figure 2B:
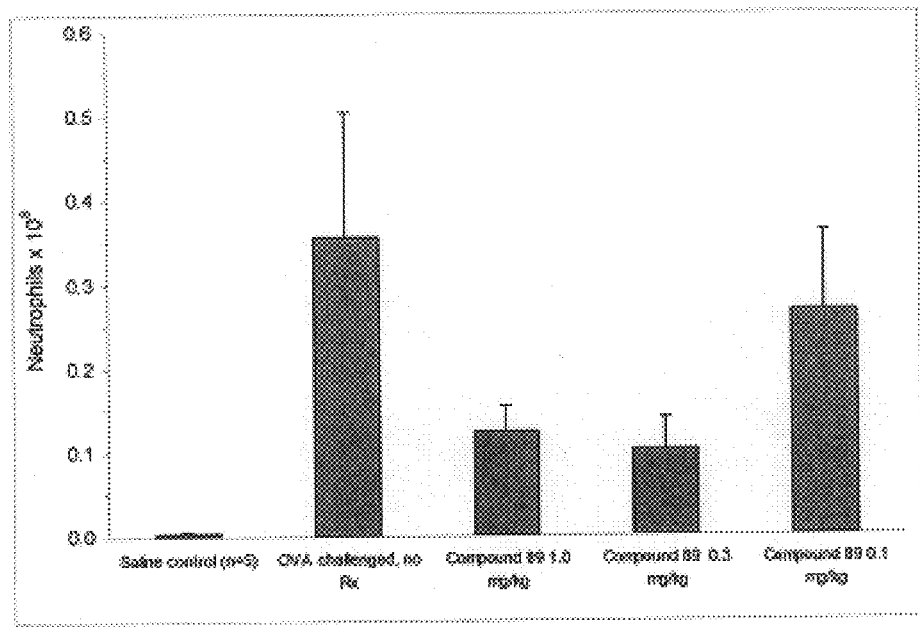
Figure 2C:
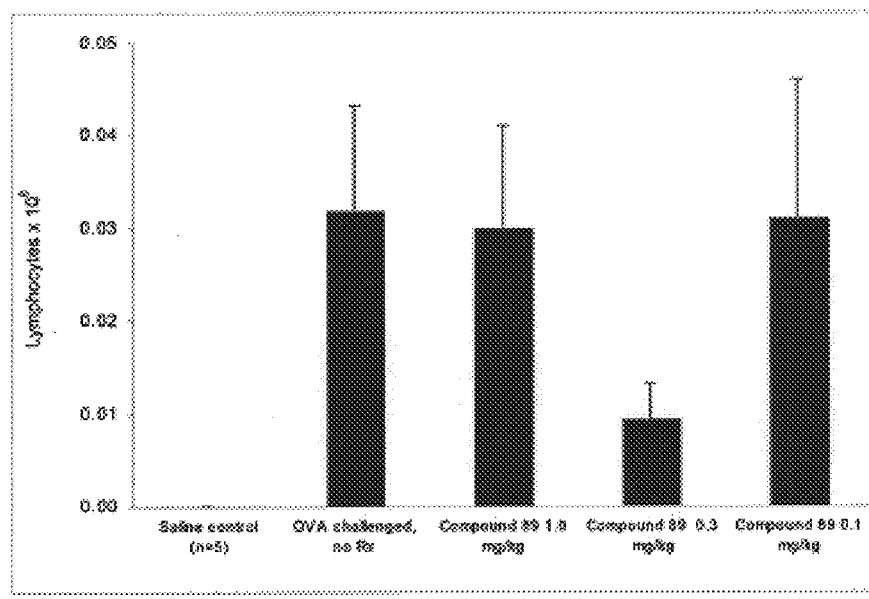
Figure 3A:
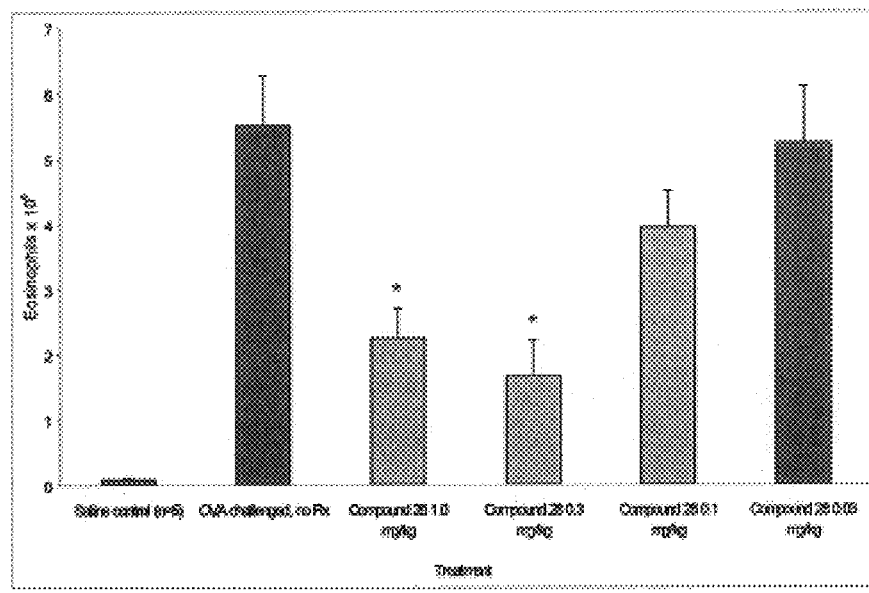
FIGS. 3A, 3B and 3C are a set of bar graphs showing the effect of compound 28 (dose response, 4 doses qd, p.o.) on ovalbumin-induced accumulation of inflammatory cells in the lung lavage fluid obtained from sensitized Brown Norway rats.
Figure 3B:
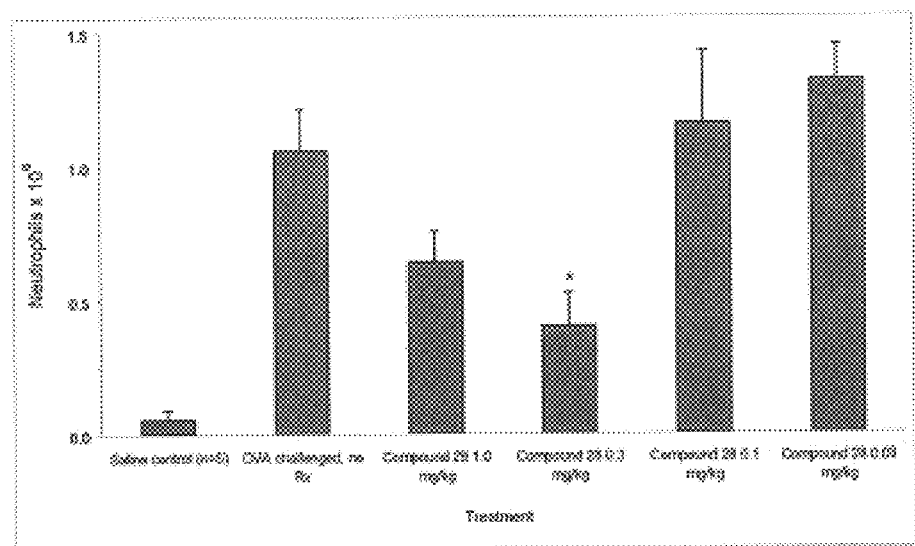
Figure 3C:
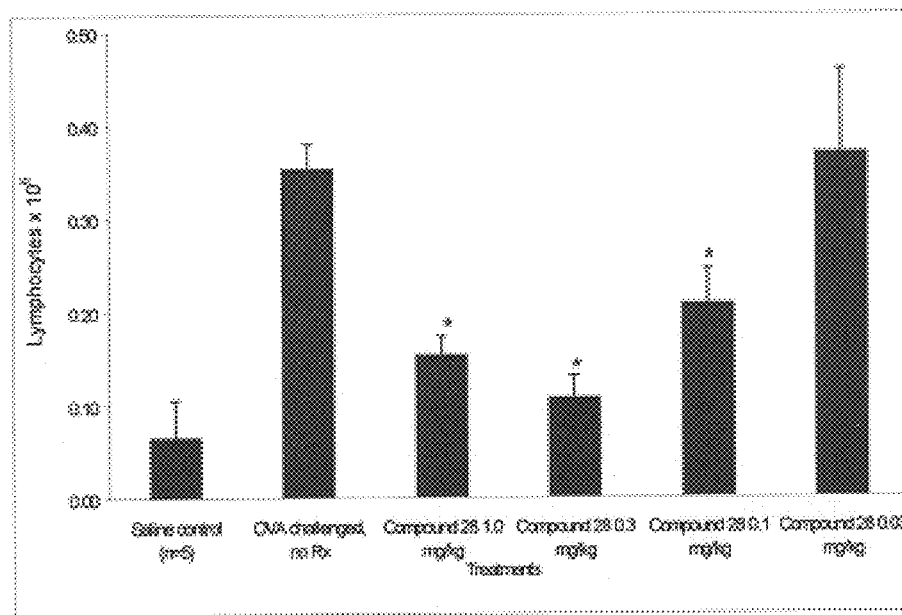

With a 3-amino steroid, such as prepared by any of the above Schemes A–G, a large variety of secondary and tertiary amine compounds of the invention can be prepared. FIGS. 1A and 1B outline several synthetic pathways that may be employed to prepare 3-amino compounds of the present invention. For instance, reductive amination methods may be used to couple primary (see FIG. 1A) and secondary (see FIG. 1B) amines with aldehydes (RC(=O)H) and ketones (RC(=O)R$^1$). Although not shown in either of FIG. 1A or 1B, compounds having two aldehyde groups, i.e., dialdehydes of the general formula HC(=O)—R—C(=O)H, may be reacted with 3-amino steroids to provide steroids having heterocyclic structures at the 3-position. In addition (or alternatively), reductive amination methods may be used to couple 3-keto steroids with heterocyclic secondary amines. By these approaches, the present invention provides compounds wherein R$^1$ and R$^2$ may, together with the N to which they are both bonded, form a heterocyclic structure that may be part of an organic group having 1–30 carbons and optionally containing 1–6 heteroatoms selected from nitrogen, oxygen and silicon. Commercial sources and reference to the chemical literature provides one of ordinary skill in the art with access to a multitude of aldehydes (including dialdehyes) and ketones that may be used to prepare steroid compounds of the present invention. Reductive amination methods are described in, for example *Synthesis* 1975, 135; *J. Am. Chem. Soc.* 1971, 93, 2897; M. Freifelder in "Catalytic Hydrogenation in Organic Synthesis" J. Wiley & Sons 1978, Ch. 10; *Russ. Chem. Rev.* 1980, 49, 14, and references cited therein. See also, *J. Chem. Soc. Perkin Trans* 1 1998, 2527; and *Synlett* 1999, 1781, as well as references cited therein.

Primary (see FIG. 1A) and secondary (see FIG. 1B) amines can be coupled to aryl compounds (ArX) to generate a variety of aryl substituted amine compounds of the invention. Commercial sources and reference to the chemical literature provides one of ordinary skill in the art with access to a multitude of aryl compounds that may be used to prepare steroid compounds of the present invention. Examples of methods for the amination of aryl compounds can be found in *J. Org. Chem.* 2000, 65, 1158 and in the review *Angew. Chem. Int. Ed.* 1998, 37, 2046 and references cited therein.

Methods to react primary (see FIG. 1A) and secondary (see FIG. 1B) amines with acyl chlorides (RC(=O)Cl) and sulfonyl chlorides (RSO$_2$Cl) to generate amide and sulfonamide compounds of the invention, respectively, are well known to those skilled in the art of organic chemistry, in the context of other amine compounds, and these same techniques may be applied to the amine compounds of the present invention. Commercial sources and reference to the chemical literature provides one of ordinary skill in the art with access to a multitude of acyl chlorides and sulfonyl chlorides that may be used to prepare steroid compounds of the present invention.

Methods to react primary (see FIG. 1A) and secondary (see FIG. 1B) amines with isocyanates (RN=C=O) and isothiocyanates (RN=C=S) to generate ureas and thioureas, respectively, are also well known to those skilled in the art of organic chemistry, in the context of other amine compounds, and these same techniques may be applied to the amine compounds of the present invention. Commercial sources and reference to the chemical literature provides one of ordinary skill in the art with access to a multitude of isocyanates and isothiocyanates that may be used to prepare steroid compounds of the present invention. The review article *Russ. Chem. Rev.* 1985, 54, 249 and references cited therein describes examples of the variety of substituted ureas and thioureas that can be encompassed by the invention.

Thus, by using appropriately selected aldehydes, ketones, aryl compounds, acyl chlorides, sulfonyl chlorides, isocyanates and/or isothiocyanates, one of ordinary skill in the art may prepare steroid compounds wherein $R^1$ and $R^2$ are selected from hydrogen and organic groups having 1–30 carbons and optionally containing 1–6 heteroatoms selected from nitrogen, oxygen, phosphorous, silicon, and sulfur.

Steroids of the invention may have fused heterocycles such as, but not limited to, pyrazole, isoxazole and pyrimidine. As illustrated in Scheme H, compound 43 is an example of a fused pyrazole of the invention, for which the synthesis of the starting material compound 40 is described in U.S. Pat. No. 6,046,185. Treatment of compound 40 with ethyl formate in pyridine in the presence of NaOMe gives the hydroxymethylene intermediate 41. Reaction of compound 41 with hydrazine hydrate in EtOH forms the pyrazole compound 42, which upon treatment with tetrabutylammonium fluoride in THF gives the compound 43.

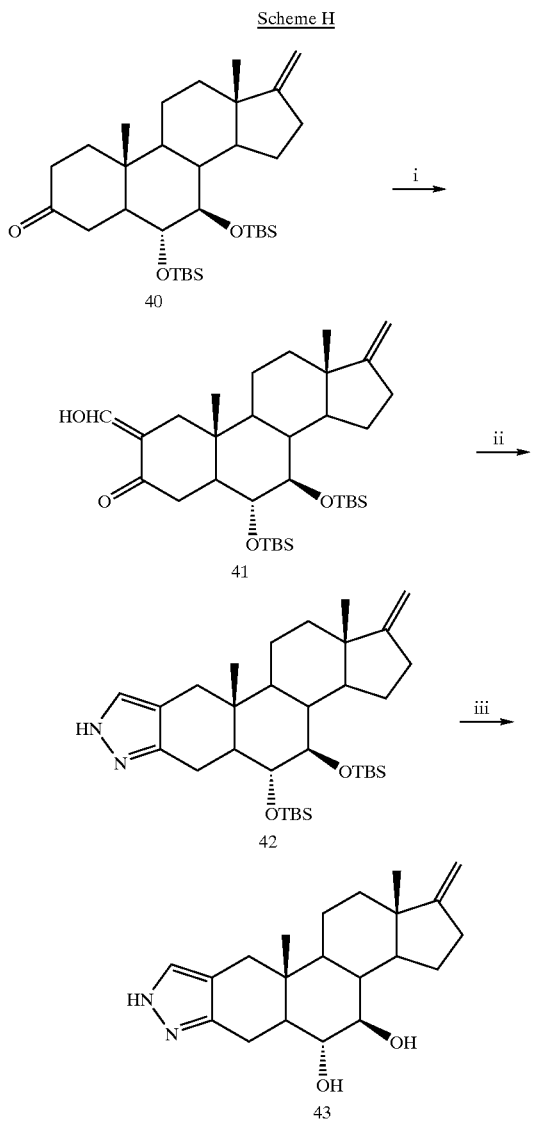

i) EtO$_2$CH, NaOMe, pyridine; ii) N$_2$H$_4$, EtOH; iii) Bu$_4$NF, THF.

As illustrated in Scheme I, intermediates such as compound 41 may be converted into isoxazoles of which compound 44 is exemplary. Treatment of the hydroxymethylene intermediate 41 with ammonium hydroxide in pyridine followed by deprotection of the 6- and 7-hydroxyls using tetrabutylammonium fluoride in THF gives the isoxazole 44.

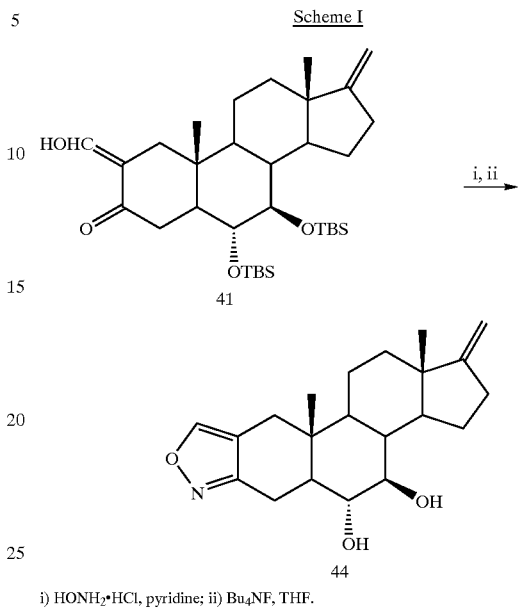

i) HONH$_2$·HCl, pyridine; ii) Bu$_4$NF, THF.

As illustrated in Scheme J, intermediates such as compound 41 may be converted into pyrimidines of which compound 44a is exemplary. Treatment of the hydroxymethylene intermediate 41 with benzamidine hydrochloride and potassium hydroxide in ethanol followed by deprotection of the 6- and 7-hydroxyls using tetrabutylammonium fluoride in THF gives the pyrimidine 44a.

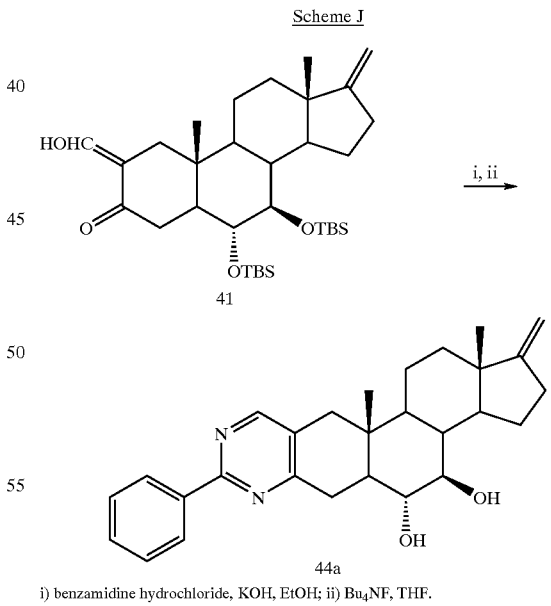

i) benzamidine hydrochloride, KOH, EtOH; ii) Bu$_4$NF, THF.

Thus, by proceeding through compounds having keto substitution as carbon 3 and =CHOH substitution at carbon 2, the present invention provides access to a multitude of compounds wherein $R^1$ may be a 2 or 3 atom chain to numeral 2 so that —N—$R^1$— forms part of a fused bicyclic structure to ring A.

Reaction of 3-keto steroids with hydroxylamine and pyridine may be employed to produce steroid oximes of the invention. A steroid oxime has $R^2$ as a direct bond to numeral 3, thus providing a double bond between the carbon at numeral 3 and the N, and $R^1$ is OH. Primary amines may be oxidized to nitro compounds by, for instance, dimethyldioxirane. Thus, $R^1$ and $R^2$ may be oxygen. Methods to generate the nitro functionality are described in *J. Org. Chem.* 1989, 54, 5783. Reaction of 3-ketones with dimethylhydrazine gives N,N-dimethylhydrazone steroids of the invention in which $R^2$ is a direct bond to numeral 3 and $R^1$ is $NMe_2$. Treatment of dimethylhydrazone steroids with hydrazine generates hydrazone steroids of the invention. Description of the methods to generate N,N-dimethylhydrazones and hydrazones can be found in *J. Org. Chem.* 1966, 31, 677. Primary amines may also be reacted by methodology known in the art with sulfonic/sulfuric acids and esters to provide sulfamate compounds, i.e., steroids wherein numeral 3 is bonded to —N—$SO_3$—R and R is H or an organic group having 1–30 carbons and optionally containing 1–6 heteroatoms selected from nigrogen, oxygen, phosphorous, silicon, and sulfur.

D. Pharmaceutical Compositions

The present invention provides a pharmaceutical or veterinary composition (hereinafter, simply referred to as a pharmaceutical composition) containing a compound of formula (1) as described above, in admixture with a pharmaceutically acceptable carrier. The invention further provides a composition, preferably a pharmaceutical composition, containing an effective amount of a compound as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, ocular, and intranasal. The term parenteral as used herein includes subcutaneous injections, intravenous, intramuscular, intrastemal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of a compound of formula (1) in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes an (where "a" and "an" refers here, and throughout this specification, as one or more) active compound of formula (1) as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol, cyclodextrin or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound of formula (1) such that a suitable dosage will be obtained. Typically, this amount is at least 0.01% of a compound of the invention in the composition. When intended for oral administration, this amount may be varied to be between 0.1% and about 80% of the weight of the composition. Preferred oral compositions contain between about 4% and about 50% of the active compound of formula (1). Preferred compositions and preparations according to the present invention are prepared so that a parenteral dosage unit contains between 0.01% to 2% by weight of active compound.

The pharmaceutical composition may be intended for topical administration, in which case the carrier may suitably comprise a solution, emulsion, ointment or gel base.

The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of formula (1) of from about 0.1% to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the active component(s) and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of inflammation (including asthma, allergy, rheumatoid arthritis, multiple sclerosis, etc.), proliferative disorders (cancers), diseases treatable through the regulation of calcium (including hypertension, cardiac arrhythmias, etc.), and Acquired Immune Deficiency Syndrome (AIDS).

The pharmaceutical compositions may be prepared by methodology well known in the pharmaceutical art.

A composition intended to be administered by injection can be prepared by combining the compound of formula (1) with water so as to form a solution. A surfactant may be added to facilitate the formation of a homogeneous solution or suspension. Surfactants are compounds that non-covalently interact with the compound of formula (1) so as to facilitate dissolution or homogeneous suspension of the active compound in the aqueous delivery system.

E. Biological Activity

The compounds disclosed herein of formula 1, or compositions comprising one of more of these compounds and a pharmaceutically acceptable carrier, diluent or excipient, may be used in a method for treating or preventing an inflammatory condition or disease in a patient, where the method comprises administering to the patient in need thereof an amount of a compound or composition according to the present invention, where the amount is effective to treat or prevent the inflammatory condition or disease of the patient.

The inflammatory condition or disease may involve respiratory inflammation (e.g., wherein the respiratory disease is asthma, or wherein the respiratory disease is chronic obstructive pulmonary disease; or wherein the respiratory disease is emphysema); the inflammatory condition may be an autoimmune condition or disease; the inflammatory condition or disease may be lupus erythematosus disease; the inflammatory condition or disease may involve acute or chronic inflammation of bone and/or cartilage compartments of joints; the inflammatory condition or disease may be an arthritis selected from rheumatoid arthritis, gouty arthritis or juvenile rheumatoid arthritis; the inflammatory condition or disease may be a central nervous system disease; the condition or disease may be associated with leukocyte infiltration; the condition or disease may be associated with edema; the condition or disease may be associated with ischemia reperfusion injury; the condition or disease may be associated with elevated levels of inflammatory cytokines (e.g., wherein the inflammatory cytokine is interleukin (IL)-4, or wherein the inflammatory cytokine is IL-5, or wherein the inflammatory cytokine is IL-10, or wherein the inflammatory cytokine is IL-13, or wherein the inflammatory cytokine is IL-9, or wherein the inflammatory cytokine is IL-1, or wherein the inflammatory cytokine is IL-2, or wherein the inflammatory cytokine is IL-6, or wherein the inflammatory cytokine is IL-18, or wherein the inflammatory cytokine is IL-3, or wherein the inflammatory cytokine is IL-8, or wherein the inflammatory cytokine is IL-12, or wherein the inflammatory cytokine is TNF-$\alpha$, or wherein the inflammatory cytokine is TGF-$\beta$, or wherein the inflammatory cytokine is GM-CSF, or wherein the inflammatory cytokine is IFN-$\gamma$, or wherein the inflammatory cytokine is LTB4, or wherein the inflammatory cytokine is a member of the cysteinyl leukotriene family, or wherein the inflammatory cytokine is regulated on activation normal T cell expressed and secreted (RANTES), or wherein the inflammatory cytokine is eotaxin-1, 2, or 3, or wherein the inflammatory cytokine is macrophage inflammatory protein (MIP)-1$\alpha$, or wherein the inflammatory cytokine is monocyte chemoattractant protein-1, 2, 3, or 4,); the condition or disease may be associated with altered levels of inflammatory adhesion molecules (e.g., wherein the adhesion molecule is vascular cell adhesion molecule (VCAM-1 or 2), wherein the adhesion molecule is intercellular adhesion molecule (ICAM-1 or 2), wherein the adhesion molecule is very late antigen-4 (VLA-4), wherein the adhesion molecule is leukocyte function associated antigen-1 (LFA-1); wherein the adhesion molecule is a selectin); the inflammatory condition or disease may be multiple sclerosis; the inflammatory condition or disease may be pulmonary sarcadosis; the inflammatory condition or disease may be ocular inflammation or allergy; the inflammatory condition or disease may be allergic rhinitis; the inflammatory condition or disease may be an inflammatory bowel disease (e.g., Crohn's disease or ulcerative colitis); the inflammatory condition or disease may be an inflammatory cutaneous disease (e.g., psoriasis or dermatitis); the inflammatory condition or disease may be graft vs host disease; the inflammatory condition or disease may be vascular (e.g., vasculitis); the inflammatory condition or disease may be an atherosclerotic disease.

Furthermore, the present invention provides a method for treating or preventing a disease or condition in a patient, where the disease or condition is associated with pathological conditions that involve leukocyte infiltration, the method comprising administering to a patient in need thereof an amount of a compound or a composition of the present invention, wherein the amount is effective to treat or prevent a disease or condition associated with pathological conditions that involve leukocyte infiltration.

Furthermore, the present invention provides a method of treating or preventing asthma in a patient, comprising administering to a patient in need thereof an amount of a compound or composition of the present invention, where the amount is effective to treat or prevent asthma in the patient.

Furthermore, the present invention provides a method of treating or preventing allergy in a patient, comprising administering to a patient in need thereof an amount of a compound or composition of the present invention, where the amount is effective to treat or prevent allergy in the patient.

In a method of the present invention, a compound of formula (1), or a composition comprising one or more compounds of formula (1) and a pharmaceutically acceptable carrier, diluent or excipient, may, although need not, achieve one or more of the following desired results in the subject to whom has been administered a compound of formula (1) as defined above, or a composition containing one of these compounds and a pharmaceutically acceptable carrier, diluent or excipient:

1. Inhibition of leukocyte infiltration (e.g., neutrophils, eosinophils, etc.)
2. Inhibition of leukocyte activation
3. Alteration of lymphocyte ratio (e.g., TH1 vs TH2 cells)
4. Inhibition of leukocyte chemotaxis;
5. Inhibition of TNF-α production and/or release;
6. Inhibition of chemokine production and/or release (e.g., eotaxin, etc.);
7. Inhibition of adhesion molecule production, release and/or function (e.g. VCAM, VLA-4, etc.);
8. Inhibition of edema;
9. Inhibition of interleukin cytokine production and/or release (e.g. IL-1, IL-2, IL-3, IL-4, IL-5, IL6, IL-8, IL-9, IL10, IL-12, IL-13, IL-18,);
10. Inhibition of inflammatory mediator release (e.g. leukotrienes, tryptase, adenosine etc.);
11. Inhibition of histamine release;
12. Inhibition of parameters of asthma; and
13. Inhibition of parameters of allergy.

The compounds disclosed herein of formula 1 (i.e., compounds of formulae (1), or compounds of the present invention), or compositions comprising one of more of these compounds and a pharmaceutically acceptable carrier, diluent or excipient, may be used in a method for treating or preventing a proliferative disorder in a patient, where the method comprises administering to the patient in need thereof an amount of a compound or composition according to the present invention, where the amount is effective to treat or prevent the proliferative disorder of the patient. As used herein, proliferative disorders includes, without limitation, all leukemias and solid tumors that are susceptible to undergoing differentiation or apoptosis upon interruption of their cell cycle.

The compounds disclosed herein of formula 1 (i.e., compounds of formulae (1), or compounds of the present invention), or compositions comprising one or more of these compounds and a pharmaceutically acceptable carrier, diluent or excipient, may be used in a method for treating or preventing diseases treatable through regulation of calcium in a patient, where the method comprises administering to the patient in need thereof an amount of a compound or composition according to the present invention, where the amount is effective to treat or prevent the disease of the patient. As used herein, diseases treatable through regulation of calcium includes, without limitation, cardiac arrhythmia, atrial fibrillation, acute coronary syndromes, hypertension, ischemia reperfusion injury, stroke, epilepsy, demyelinating diseases such as multiple sclerosis, pain, status epilepticus, artherosclerosis, and diabetes.

The compounds disclosed herein of formula 1 (i.e., compounds of formulae (1), or compounds of the present invention), or compositions comprising one or more of these compounds and a pharmaceutically acceptable carrier, diluent or excipient, may be used in a method for treating or preventing Acquired Immunodeficiency Syndromes (AIDS) in a patient, where the method comprises administering to the patient in need thereof an amount of a compound or composition according to the present invention, where the amount is effective to treat or prevent the Acquired Immunodeficiency Syndromes of the patient. As used herein, Acquired Immunodeficiency Syndromes through infection with human immunodeficiency virus type 1 includes, without limitation, associated complications such as Acquired Immunodeficiency Syndrome Dementia Complex, and neuro-Acquired Immunodeficiency Syndromes.

Thus, the inventive method may be used to treat inflammation, including both acute and chronic inflammation, as well as certain proliferative disorders (cancers), diseases treatable through regulation of calcium, and AIDS. As used herein, inflammation includes, without limitation, ankylosing spondylitis, arthritis (where this term encompasses over 100 kinds of rheumatic diseases), asthma, chronic obstructive pulmonary disease, allergy, allergic rhinitis, Crohn's disease, fibromyalgia syndrome, gout, inflammations of the brain (including multiple sclerosis, AIDS dementia, Lyme encephalopathy, herpes encephalitis, Creutzfeld-Jakob disease, and cerebral toxoplasmosis), emphysema, inflammatory bowel disease, irritable bowel syndrome, ischemia-reperfusion injury, atopic dermatitis, juvenile erythematosus pulmonary sarcoidosis, Kawasaki disease, osteoarthritis, pelvic inflammatory disease, psoriatic arthritis (psoriasis), rheumatoid arthritis, psoriasis, tissue/organ transplant, graft vs host disease; scleroderma, spondyloarthropathies, systemic lupus erythematosus, pulmonary sarcoidosis, vasculitis, artherosclerosis, cardiomyopathy, autoimmune myocarditis, and ulcerative colitis.

The inventive method provides for administering a therapeutically effective amount of a compound of formula (1), including salts, compositions etc. thereof. As used herein, the actual amount encompassed by the term "therapeutically effective amount" will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors that those skilled in the medical arts will recognize.

An effective amount of a compound or composition of the present invention will be sufficient to treat inflammation, proliferative diseases, diseases treatable by regulation of calcium, or AIDS, in a warm-blooded animal, such as a human. Methods of administering effective amounts of anti-inflammatory agents are well known in the art and include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multi-dose inhalation devices.

The dosage amount and frequency are selected to create an effective level of the agent without harmful effects. It will generally range from a dosage of about 0.001 to 100 mg/Kg/day, and typically from about 0.01 to 10 mg/Kg/day where administered orally or intravenously. Also, the dosage range will be typically from about 0.0001 to 10 mg/Kg/day where administered intranasally or by inhalation.

The compounds of formula (1) including the compounds used in the methods and compositions set forth above, may be prepared according to the Schemes set forth in the following examples. The following examples are offered by way of illustration and not by way of limitation.

Unless otherwise stated, flash chromatography and column chromatography may be accomplished using Merck silica gel 60 (230–400 mesh). Flash chromatography may be carried out according to the procedure set forth in: "Purification of Laboratory Chemicals", 3rd. edition, Butterworth-Heinemann Ltd., Oxford (1988), Eds. D. D. Perrin and W. L. F. Armarego, page 23. Column chromatography refers to the process whereby the flow rate of eluent through a packing material is determined by gravity. In all cases flash chromatography and radial chromatography may be used interchangeably. Radial chromatography is performed using silica gel on a Chromatotron Model # 7924T (Harrison Research, Palo Alto, Calif.). Unless otherwise stated, quoted $R_f$ values are obtained by thin layer chromatography using Silica Gel 60 $F_{254}$ (Merck KGaA, 64271, Darmstadt, Germany). Brine refers to a saturated solution of sodium chloride.

Also, unless otherwise stated, chemical reactants and reagents were obtained from standard chemical supply houses, such as Aldrich (Milwaukee, Wis.; www.aldrich.sial.com); EM Industries, Inc. (Hawthorne, N.Y.; www.emscience.com); Fisher Scientific Co. (Hampton, N.H.; www.fischer1.com); and Lancaster Synthesis, Inc. (Windham, N.H.; www.lancaster.co.uk). Sulfo-NHS-biotin was obtained from Pierce (Rockford, Ill., www.piercenet.com). MP-TsOH resin, PS-DIEA resin, PS-Trisamine resin and PS-Benzaldehyde resin were obtained from Argonaut Technologies (San Carlos, Calif., www.argotech.com). Gases were obtained from Praxair (Vancouver, B.C.). Cell lines, unless otherwise stated, where obtained from public or commercial sources, e.g., American Tissue Culture Collection (ATCC, Rockville, Md.).

SYNTHESIS EXAMPLES

Example 1

3-Amino-6,7-dihydroxy-17-ethylidene Steroid

Compound 49, a representative compound of the invention, is prepared according to Scheme 1. Any number of compounds related to compound 49 could be produced using similar methodology. The starting material compound 45 can be prepared according to the methodology described in U.S. Pat. No. 6,046,185. Olefination of the ketone 45 is accomplished using ethyltriphenylphosphonium bromide and KO$^t$Bu in toluene. Treatment of the 3β-hydroxyl compound 46 with ZnN$_6$.2py, triphenylphosphine and DIAD in toluene produced the 3α-azido compound 47. Lithium aluminum hydride reduction of the azide in Et$_2$O provided the amine 48. Treatment with HCl in THF and water removes the acetonide group and forms the ammonium chloride salt 49.

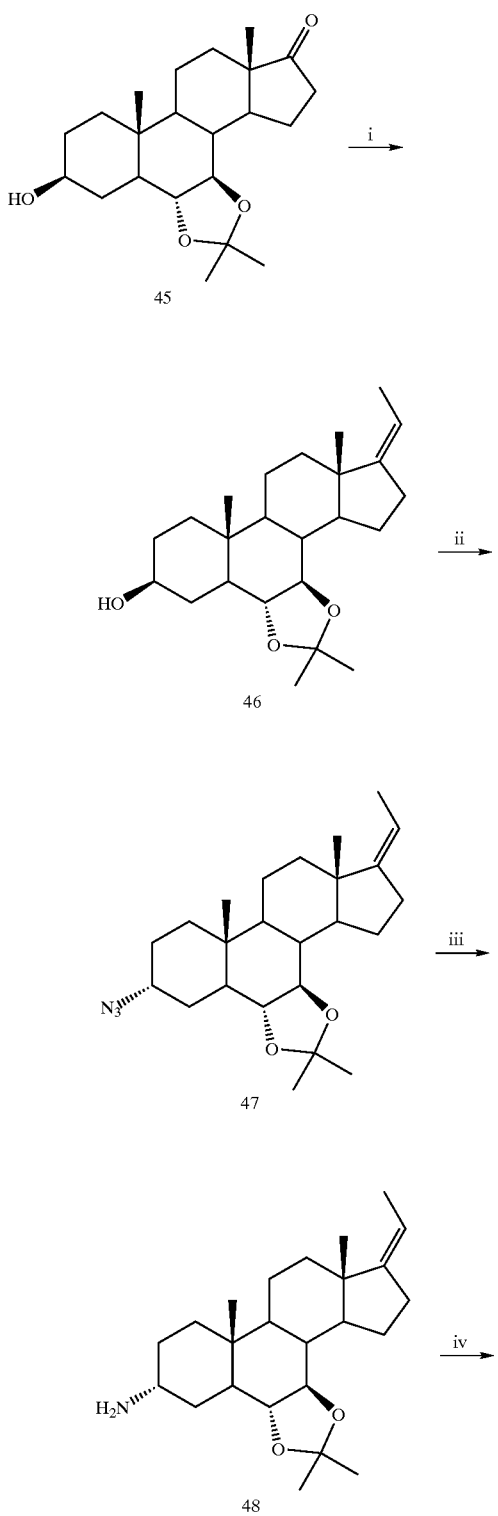

Scheme 1

-continued

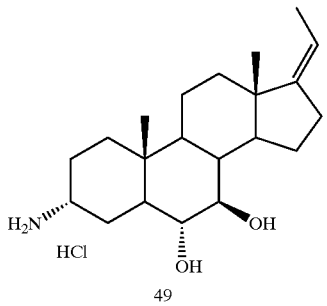

49 i) CH₃CH₂PPh₃Br, KO'Bu, Toluene; ii) ZnN₆·2py, Ph₃P, DIAD, toluene; iii) LiAlH₄, Et₂O; iv) HCl, THF, water.

Synthesis of Compound 46

A solution of KO$^t$Bu (0.24 g, 2.0 mmol), EtPPh₃Br (0.75 g, 2.0 mmol) and toluene (2.5 ml) was stirred at room temperature under argon. After 1 hour the deep red solution was cooled in ice and the ketone 45 (184 mg, 0.508 mmol) was added and the resulting solution was allowed to warm to room temperature. After stirring overnight the reaction was quenched with 10 ml of water, diluted with 60 ml of ethyl acetate (EtOAc), separated and washed with 2×10 ml of brine, dried over MgSO₄, filtered and concentrated. Purification by column chromatography eluting with 1:1 EtOAc/hexanes afforded 171 mg (90%) of compound 46 as a colorless film.

Synthesis of Compound 47

DIAD (0.44 ml, 2.14 mmol) was added dropwise over 10 minutes to a room temperature solution of the 3β-hydroxy compound 46 (400 mg, 1.07 mmol), ZnN₆·2py (246 mg, 0.80 mmol), Ph₃P (560 mg, 2.14 mmol) and toluene (10.7 ml) under argon. After 4 hours the reaction mixture was loaded onto a column of silica gel packed in 10% ethyl acetate/hexanes and eluted with 20% ethyl acetate/hexanes to afford 422 mg (99%) of compound 47 as a white solid.

Synthesis of Compound 48

Lithium aluminum hydride (42 mg, 1.04 mmol) was added to an ice cooled solution of the azide 47 (415 mg, 1.04 mmol) in 5.2 ml of Et₂O under argon. The reaction was allowed to warm to room temperature. After 2 hours the solution was cooled in ice, diluted with 25 ml of diethyl ether and slowly quenched with 2 ml of saturated Na₂SO₄ solution. After 10 minutes a white precipitate had formed and the solution was diluted with 50 ml of ethyl acetate, washed with 3×10 ml of brine, dried over MgSO₄, filtered and concentrated. The crude material was purified using a column of silica gel prepared by packing in 1% Et₃N/CH₂Cl₂ and washing with 5% MeOH/CH₂Cl₂. The crude material was loaded in CH₂Cl₂, eluted with 5% MeOH/CH₂Cl₂ and then 95:5:2 CH₂Cl₂:MeOH:Et₃N to give a white foam which was shown by ¹H nmr to contain a trace of Et₃N. The material was taken up in 50 ml of hexanes, washed with 2×20 ml of brine, dried over MgSO₄, filtered and concentrated to give 322 mg (83%) of compound 48 as a white foam.

Synthesis of Compound 49

A solution of the 3α-amino compound 48 (317 mg, 0.850 mmol), 4 M HCl in dioxane (255 μl, 1.02 mmol), THF (13.6 ml) and water (3.4 ml) was stirred at room temperature overnight. The solution was concentrated to dryness, triturated with 3×10 ml portions of acetone, evaporating off the acetone after each trituration. Concentration gave 301 mg (96%) of compound 49 as a white solid. LC/MS (direct infusion, electrospray +ve, 10 mM NH₄OAc in 4:1 water and MeCN) 334.16; C₂₁H₃₆NO₂.

Example 2

3-Amino-6,7-dihydroxy-17-methylidene Steroid

A further example of alkenes related to compound 49 is shown in Scheme 2. Olefination of the ketone 45 using methyltriphenylphosphonium bromide and KO$^t$Bu in THF gave the 17-methylidene compound 50. Azidation using ZnN₆·2py, PPh₃ and DIAD in toluene gave the 3α-azido compound 51. Lithium aluminum hydride reduction in THF gave the 3α-amino compound 52. Treatment with 80% acetic acid removed the acetonide protecting group and formed the ammonium acetate salt 53. Alternatively compound 52 was treated with hydrochloric acid in acetonitrile and water to give the hydrochloride salt 54.

Scheme 2

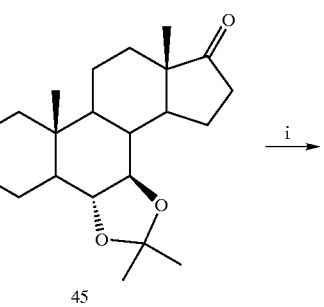

45

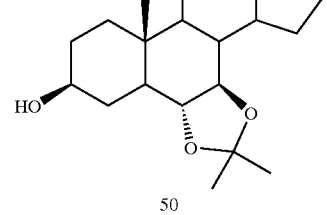

50

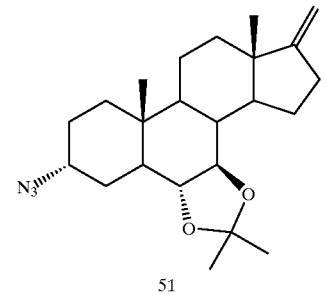

51

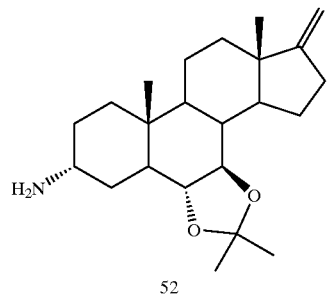

52

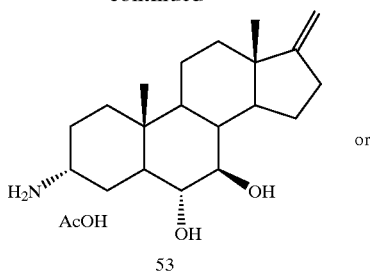

53 or

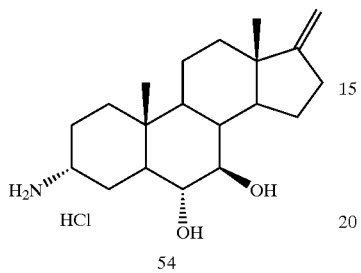

54 i) CH₃PPh₃Br, KOᵗBu, THF; ii) ZnN₆·2py, Ph₃P, DIAD, toluene; iii) LiAlH₄, Et₂O; iv) 80% acetic acid or HCl, water, MeCN.

Synthesis of Compound 50

A solution of KOᵗBu (2.0 g, 16.9 mmol), MePPh₃Br (6.0 g, 16.8 mmol) and 27 ml of THF was stirred at room temperature under argon. After 1 hour the ketone 45 (2.00 g, 5.52 mmol) was added to the yellow solution and the resulting solution was heated at reflux for 1 hour. The reaction was quenched with 50 ml of brine, diluted with 100 ml of EtOAc, separated and washed with 25 ml of brine, dried over MgSO₄, filtered and concentrated. Purification by column chromatography eluting with 1:1 EtOAc/hexanes afforded 1.90 g (95%) of compound 50 as a white solid.

Synthesis of Compound 51

DIAD (0.85 ml, 4.10 mmol) was added dropwise over 15 minutes to a room temperature solution of the 3β-hydroxyl compound 50 (739 mg, 2.05 mmol), ZnN₆·2py (473 mg, 1.54 mmol), Ph₃P (1.075 g, 4.10 mmol) and toluene (20 ml) under argon. After 4 hours the reaction mixture was loaded onto a column of silica gel packed in 10% ethyl acetate/hexanes and eluted with 20% ethyl acetate/hexanes to afford 743 mg (94%) of compound 51 as a white foam.

Synthesis of Compound 52

Lithium aluminum hydride (77 mg, 1.93 mmol) was added to an ice cooled solution of the 3α-azide 51 in 5 ml of THF and 5 ml of diethyl ether under argon. The reaction was allowed to warm to room temperature. After 4 hours the solution was cooled in ice, diluted with 25 ml of diethyl ether and slowly quenched with 5 ml of saturated Na₂SO₄ solution. After 10 minutes a white precipitate had formed and the solution was diluted with 50 ml of ethyl acetate, washed with 3×10 ml of brine, dried over MgSO₄, filtered and concentrated. The crude material was purified using a column of silica gel prepared by packing in 1% Et₃N/CH₂Cl₂ and washing with 5% MeOH/CH₂Cl₂. The crude material was loaded in CH₂Cl₂, eluted with 5% MeOH/CH₂Cl₂ and then 95:5:2 CH₂Cl₂:MeOH:Et₃N to give 636 mg (92%) of compound 52 as a white solid.

Synthesis of Compound 53

A solution of the 3α-amine 52 (287 mg, 0.799 mmol) and 10 ml of 80% acetic acid was heated at 40° C. for 1 hour. The reaction mixture was concentrated to give a white foam. Acetone (10 ml) was added and the solution was sonicated to dissolve the material and then evaporated. Another 10 ml portion of acetone was added, sonicated and evaporated to give 301 mg (99%) of compound 53 as a white solid. LC/MS (direct infusion, electrospray +ve, 10 mM NH₄OAc in 4:1 water and MeCN) 320.19; $C_{20}H_{34}NO_2$.

Synthesis of Compound 54

A solution of 4 M HCl in dioxane was added to a solution of the amine 52 in 1 ml of acetonitrile and 50 µl of water. The resulting gummy solid was diluted with 2 ml of acetonitrile and stirred vigorously until a solid formed. The solid was filtered and dried to give 50 mg (63%) of compound 54. LC/MS (direct infusion, electrospray +ve, 10 mM NH₄OAc in 4:1 water and MeCN) 320.19; $C_{20}H_{34}NO_2$.

Example 3

3-Amino-6,7-dihydroxy-17-methylidene Steroid

Alternative Synthesis

Intermediate 52 was also synthesized by the alternate route shown in Scheme 3. Azidation of the alcohol 45 using ZnN₆·2py, PPh₃ and DIAD in toluene gave the 3α-azido compound 55. Hydrogenation of the azide, using Pd on carbon as catalyst gave the amine 56. Olefination of compound 56 using methyltriphenylphosphonium bromide and KOᵗBu in THF gave the 17-methylidene compound 52.

Scheme 3

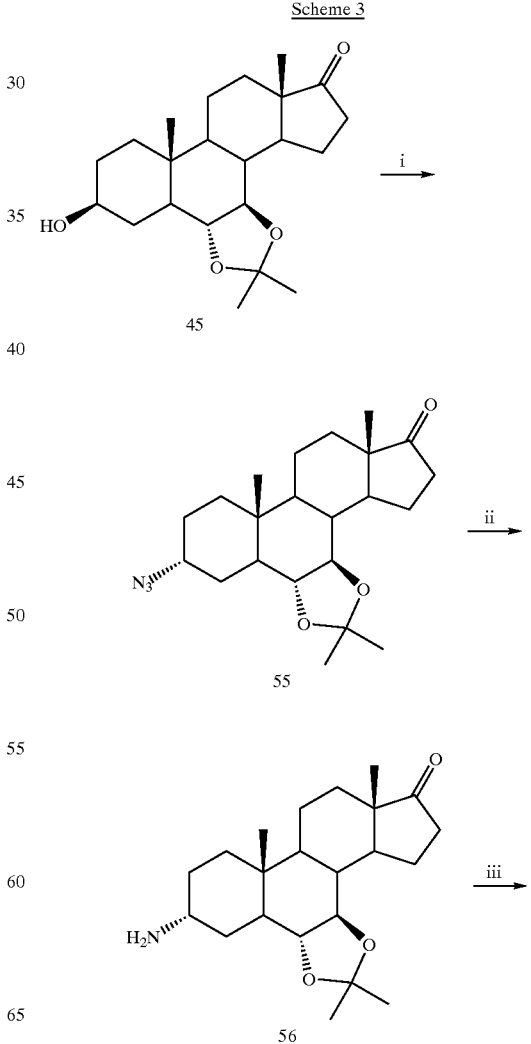

-continued

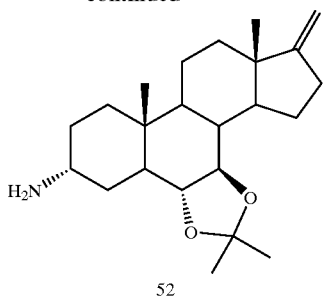

52 i) ZnN$_6$·2py, Ph$_3$P, DIAD, toluene; ii) H$_2$, Pd, EtOAc; iii) CH$_3$PPh$_3$Br, KO$^t$Bu, THF.

Synthesis of Compound 55

DIAD (2.4 ml, 11.6 mmol) was added dropwise over 20 minutes to a room temperature solution of the 3β-hydroxyl compound 45 (2.108 g, 5.81 mmol), ZnN$_6$.2py (1.34 g, 4.36 mmol), Ph$_3$P (3.05 g, 11.6 mmol) and toluene (58 ml) under argon. After being allowed to react overnight, the reaction mixture was loaded onto a column of silica gel and eluted with 20% ethyl acetate/hexanes to afford 1.14 g (50%) of compound 55 as a white foam.

Synthesis of Compound 56

A solution of the azide 55 (1.10 g, 2.84 mmol), 10% Pd on carbon (60 mg, 0.057 mmol) and 28 ml of ethyl acetate was stirred at room temperature overnight under hydrogen. The solution was filtered through celite eluting with ethyl acetate. Purification by radial chromatography eluting with 95:5:2 CH$_2$Cl$_2$:MeOH:Et$_3$N gave 892 mg (81%) of compound 56 as a white solid.

Synthesis of Compound 52

A solution of KO$^t$BU (175 mg, 1.48 mmol), MePPh$_3$Br (528 mg, 1.48 mmol) and 3 ml of THF was stirred at room temperature under argon. After 1 hour the ketone 56 (100 mg, 0.277 mmol) was added to the yellow solution and the resulting solution was allowed to stir at room temperature overnight. The reaction was quenched with 5 ml of water, diluted with 50 ml of EtOAc, separated and washed with 10 ml of brine, dried over MgSO$_4$, filtered and concentrated. Purification by radial chromatography eluting with 95:5:2 CH$_2$Cl$_2$:MeOH:Et$_3$N afforded 96 mg (97%) of compound 52 as a white solid.

Example 4

3-Amino-6,7-dihydroxy-17-fluoroethylidene Steroid

Halogenated analogues related to compound 49 can be prepared using halogenated olefination reagents. Scheme 4 outlines the synthesis of the 20-fluoro analogue 64. The hydroxyl in compound 45 was protected by treatment with tert-butyldimethylsilyl chloride and imidazole in dimethylformamide (DMF). Olefination of the ketone 57 using the anion of triethyl 2-fluoro-2-phosphonoacetate gives a mixture of compound 58 and its geometric isomer. The compounds are separable using silica gel chromatography. Lithium aluminum hydride reduction of the ester in Et$_2$O gave the allylic alcohol 59. Treatment with sulfur trioxide pyridine complex in THF followed by addition of lithium aluminum hydride affords the dehydroxylated compound 60. Tetrabutylammonium fluoride in THF removes the protecting group from the 3-hydroxyl to give compound 61. Azidation using ZnN$_6$.2py, PPh$_3$ and DIAD in toluene gave the 3α-azido compound 62. Lithium aluminum hydride reduction in THF gave the 3α-amine 63. Treatment with HCl in THF and water deprotected the 6- and 7-hydroxyls and formed the ammonium chloride salt 64.

Scheme 4

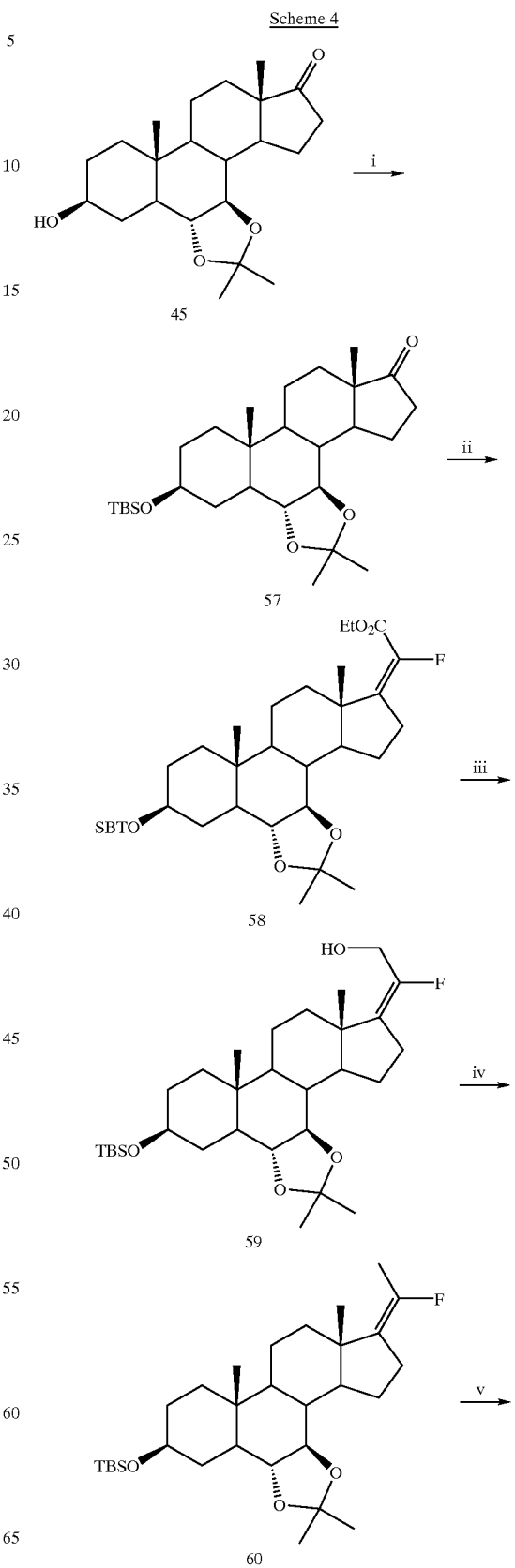

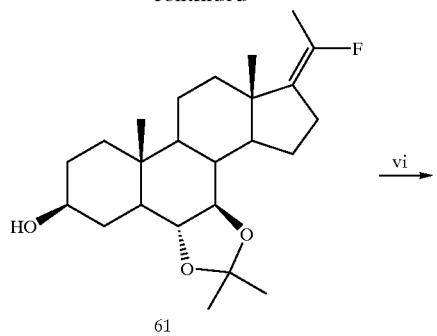

61

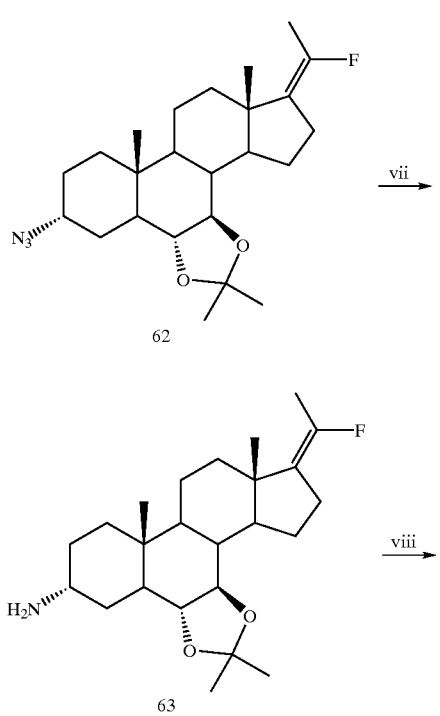

62

63

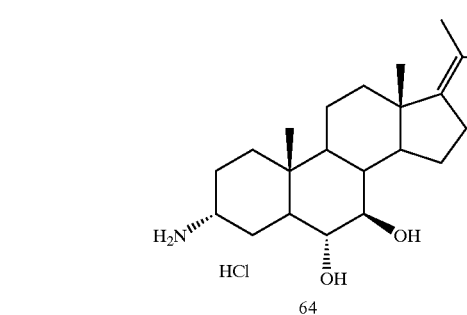

64 i) TBSCl, imidazole, DMF; ii) (EtO)$_2$P(O)CHFCO$_2$Et, LiN(TMS)$_2$, THF; iii) LiAlH$_4$, Et$_2$O; iv) SO$_3$·Py, THF; LiAlH$_4$; v) Bu$_4$NF, THF; vi) ZnN$_6$·2Py, Ph$_3$P, DIAD, toluene; vii) LiAlH$_4$, Et$_2$O; viii) HCl, THF, water.

Synthesis of Compound 57

A solution of the ketone 45 (4.73 g, 13.1 mmol), TBSCl (3.01 g, 19.6 mmol), imidazole (2.67 g, 39.2 mmol) and DMF (52 ml) was stirred at room temperature overnight. The white slurry was diluted with 250 ml of EtOAc, washed with 2×50 ml of water and 50 ml of brine, dried over MgSO$_4$, filtered and concentrated to give 5.97 g (96%) of compound 57 as white solid.

Synthesis of Compound 58

Lithium bis(trimethylsilyl)amide (10.0 ml of a 1.0 M solution in THF, 10.0 mmol) was added to a room temperature solution of (EtO)$_2$P(O)CHFCO$_2$Et (2.65 g, 10.5 mmol) in THF (22 ml) under argon. After 1 hour a solution of the ketone 57 (2.50 g, 5.25 mmol) in THF (20 ml) was added and the resulting solution was heated at reflux for 4.5 hours and then stirred at room temperature overnight. The reaction was quenched with 1.5 ml of saturated NaHCO$_3$ solution and then partially concentrated to remove most of the THF. The residue was diluted with 200 ml of EtOAc, washed with 3×20 ml of brine, dried over MgSO$_4$, filtered and concentrated. The crude material was purified by column chromatography, eluting with 2.5% then 5% EtOAc/hexanes to give 1.50 g (50%) of compound 58 as a white solid.

Synthesis of Compound 59

Lithium aluminum hydride (106 mg, 2.66 mmol) was added to an ice cooled solution of the ester 58 (1.50 g, 2.66 mmol) in Et$_2$O (13 ml) under argon. The solution was allowed to warm to room temperature. After 3 hours the solution was cooled in ice and 20 ml of saturated Na$_2$SO$_4$ solution was slowly added. After 10 minutes the solution was diluted with 150 ml of EtOAc, washed with water and brine, dried over MgSO$_4$, filtered and concentrated to give 1.44 g (quantitative) of compound 59 as a white foam.

Synthesis of Compound 60

Sulfur trioxide pyridine complex (69.5 mg, 0.428 mmol) was added to an ice cooled solution of the allylic alcohol 59 (149 mg, 0.285 mmol) in THF (2.8 ml) under argon. After 6 hours lithium aluminum hydride (68 mg, 1.71 mmol) was added and the solution was allowed to warm to room temperature overnight. The solution was cooled in ice and 5 ml of saturated Na$_2$SO$_4$ solution was slowly added. After 10 minutes the solution was diluted with 75 ml of EtOAc, washed with water and brine, dried over MgSO$_4$, filtered and concentrated to give 109 mg (76%) of compound 60 as a white solid.

Synthesis of Compound 61

A solution of compound 60 (410 mg, 0.810 mmol), Bu$_4$NF (0.89 ml of a 1.0 M solution in THF, 0.89 mmol) and THF (5 ml) was heated at reflux under argon. After 1.5 hours the solution was cooled to room temperature, diluted with 75 ml of EtOAc, washed with 20 ml of water and 2×20 ml of brine, dried over MgSO$_4$, filtered and concentrated. The residue was filtered through silica gel eluting with EtOAc and concentrated to give 318 mg (100%) of compound 61 as a white solid.

Synthesis of Compound 62

DIAD (0.33 ml, 1.59 mmol) was added dropwise over 10 minutes to a room temperature solution of the 3β-alcohol 61 (312 mg, 0.796 mmol), ZnN$_6$.2py (183 mg, 0.597 mmol), Ph$_3$P (417 mg, 1.59 mmol) and toluene (8.0 ml) under argon. After 3 hours the reaction mixture was loaded onto a column of silica gel packed in 10% EtOAc/hexanes and eluted with 20% EtOAc/hexanes to afford 322 mg (97%) of compound 62 as a crystalline solid.

Synthesis of Compound 63

Lithium aluminum hydride (29 mg, 0.75 mmol) was added to an ice cooled solution of the azide 62 (314 mg, 0.753 mmol) in 7.5 ml of Et$_2$O under argon. The reaction was allowed to warm to room temperature while stirring overnight. The solution was cooled in ice and slowly quenched with 10 ml of saturated Na$_2$SO$_4$ solution. After 10 minutes a white precipitate had formed and the solution was diluted with 75 ml of EtOAc, washed with 20 ml of water and 2×20 ml of brine, dried over MgSO$_4$, filtered and concentrated. The crude material was purified using a column of silica gel prepared by packing in 1% Et$_3$N/CH$_2$Cl$_2$ and washing with 5% MeOH/CH$_2$Cl$_2$. The crude material was loaded in CH$_2$Cl$_2$, eluted with 5% MeOH/CH$_2$Cl$_2$ and then 95:5:2 CH$_2$Cl$_2$:MeOH:Et$_3$N to give a white solid. $^1$H NMR analysis indicated the material contained a trace of Et$_3$N therefore the material was taken up in 75 ml of CH$_2$Cl$_2$ and washed with 2×25 ml of water, dried over MgSO$_4$, filtered and concentrated to give 137 mg (47%) of compound 63 as a colorless film.

Synthesis of Compound 64

A solution of the 3α-amino compound 63 (137 mg, 0.35 mmol), 4 M HCl in dioxane (105 μl, 0.42 mmol), THF (5.6 ml) and water (1.4 ml) was stirred at room temperature overnight. The solution was concentrated, the residue was twice taken up in 3 ml of methanol and concentrated to give 130 mg (96%) of compound 64 as an off-white solid. LC/MS (direct infusion, electrospray +ve, 10 mM NH$_4$OAc in 4:1 water and MeCN) 352.14; C$_{21}$H$_{35}$FNO$_2$.

Example 5

3-Amino-6,7-dihydroxy-17-carbomethoxyethylidene Steroid

Olefination of compounds related to compound 57 can also be carried out to generate 21-carboalkoxy substituted analogues. Scheme 5 shows the synthesis of the 21-carbomethoxy substituted example compound 69. Olefination of the ketone 57 using the anion of trimethyl 2-phosphonoacetate gives a mixture of compound 65 and its geometric isomer. The compounds are separable using silica gel chromatography. Tetrabutylammonium fluoride in THF removes the protecting group from the 3-hydroxyl to give compound 66. Azidation using ZnN$_6$.2py, PPh$_3$ and DIAD in toluene gave the 3α-azido compound 67. Hydrogenation of the azide, using Pd on carbon as catalyst gave the 3α-amine 68. Treatment with 80% acetic acid deprotected the 6- and 7-hydroxyls and formed the ammonium acetate salt 69.

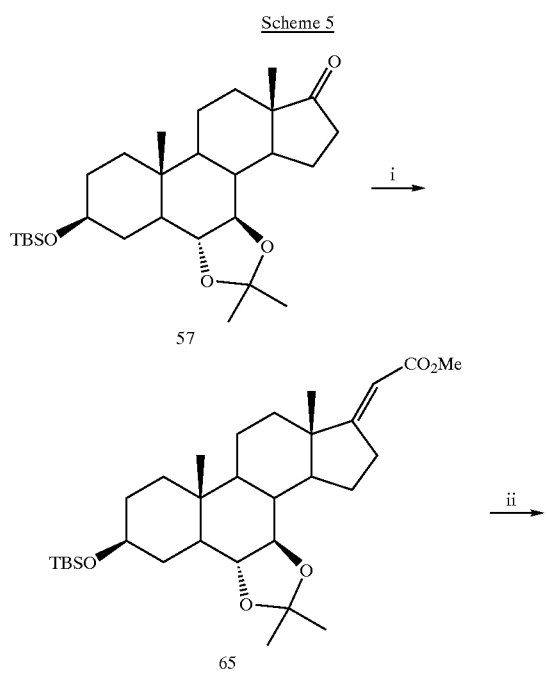

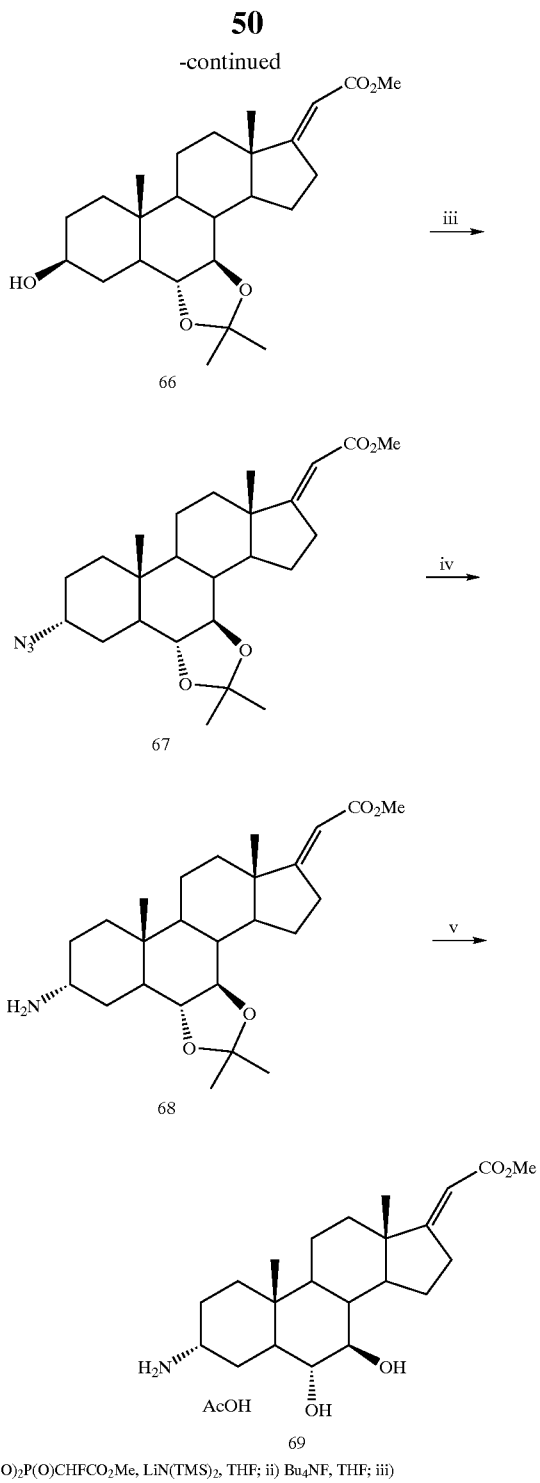

i) (MeO)$_2$P(O)CHFCO$_2$Me, LiN(TMS)$_2$, THF; ii) Bu$_4$NF, THF; iii) ZnN$_6$•2Py, Ph$_3$P, DIAD, toluene; iv) H$_2$, Pd, EtOAc; v) 80% acetic acid.

Synthesis of Compound 65

Lithium bis(trimethylsilyl)amide (2.00 ml of a 1.0 M solution in THF, 2.00 mmol) was added to a room temperature solution of (MeO)$_2$P(O)CH$_2$CO$_2$Me (390 mg, 2.10 mmol) in THF (22 ml) under argon. After 3 hours a solution of the ketone 57 (509 mg, 1.07 mmol) in THF (2 ml) was added and the resulting solution was heated at reflux for 3 days. The reaction was quenched with 5 ml of water, diluted with 75 ml of EtOAc, washed with 2×15 ml of brine, dried over MgSO$_4$, filtered and concentrated. The crude material was purified by column chromatography, eluting with 5%

EtOAc/hexanes to give 307 mg (54%) of compound 65 as a colorless film. Also isolated was 119 mg (21%) of the Z-isomer.

Synthesis of Compound 66

A solution of 65 (296 mg, 0.550 mmol), Bu$_4$NF (0.61 ml of a 1.0 M solution in THF, 0.61 mmol) and THF (3 ml) was heated at reflux under argon. After 1 hour the solution was cooled to room temperature, diluted with 20 ml of EtOAc, washed with 10 ml of water and 2×10 ml of brine, dried over MgSO$_4$, filtered and concentrated to give 230 mg (100%) of compound 66 as a white solid.

Synthesis of Compound 67

DIAD (252 μl, 1.28 mmol) was added dropwise to a room temperature solution of the 3β-alcohol 66 (230 mg, 0.55 mmol), ZnN$_6$.2py (147 mg, 0.48 mmol), Ph$_3$P (335 mg, 1.28 mmol) and toluene (6.4 ml) under argon. After 2 hours the reaction mixture was purified by radial chromatography, eluting with 15% EtOAc/hexanes to afford 203 mg (84%) of compound 67.

Synthesis of Compound 68

A solution of the azide 67 (203 mg, 0.45 mmol), 10% Pd on carbon (48 mg, 0.045 mmol) and 4.5 ml of EtOAc was stirred at room temperature under hydrogen for 3 days. The solution was filtered through celite eluting with EtOAc and MeOH to give 165 mg (88%) of compound 68.

Synthesis of Compound 69

A solution of the amine 68 (165 mg, 0.40 mmol) and 2 ml of 80% acetic acid was heated at 40° C. for 1 hour. The reaction mixture was diluted with 10 ml of toluene then concentrated to remove residual acetic acid. Trituration of the residue in 10 ml of cyclohexane, followed by filtration and drying gave 117 mg (67%) of compound 69 as a white solid. LC/MS (direct infusion, electrospray +ve, 10 mM NH$_4$OAc in 4:1 water and MeCN) 378.17; C$_{22}$H$_{36}$NO$_4$.

Example 6

3α-Amino-6α,7β-dihydroxyandrostan-17-one Acetic Acid Salt

Analogous methodology can be used to obtain compounds with different functionalities at C17. For example a 17-ketone substituted compound is obtained by treatment of compound 56 with 80% acetic acid to give 3α-amino-6α,7β-dihydroxyandrostan-17-one acetic acid salt (70) (see Table 2).

Synthesis of Compound 70

A solution of the ketone 56 (67 mg, 0.16 mmol) and 1 ml of 80% acetic acid was heated at 40° C. for 1 hour. The reaction mixture was diluted with 10 ml of toluene then concentrated to give 63 mg (100%) of compound 70. LC/MS (direct infusion, electrospray +ve, 10 mM NH$_4$OAc in 4:1 water and MeCN) 322.18; C$_{19}$H$_{32}$NO$_3$.

Example 7

3-Amino-6,7-dihydroxy-17-hydroxy Steroid

17-Hydroxyl substituted analogues can be prepared from ketones related to compound 56 as shown in Scheme 6. The carbonyl in compound 56 was reduced with NaBH$_4$ in methanol to give exclusively the 17β-hydroxyl isomer 71. Treatment with 80% acetic acid removed the acetonide protecting group and formed the ammonium acetate salt 72.

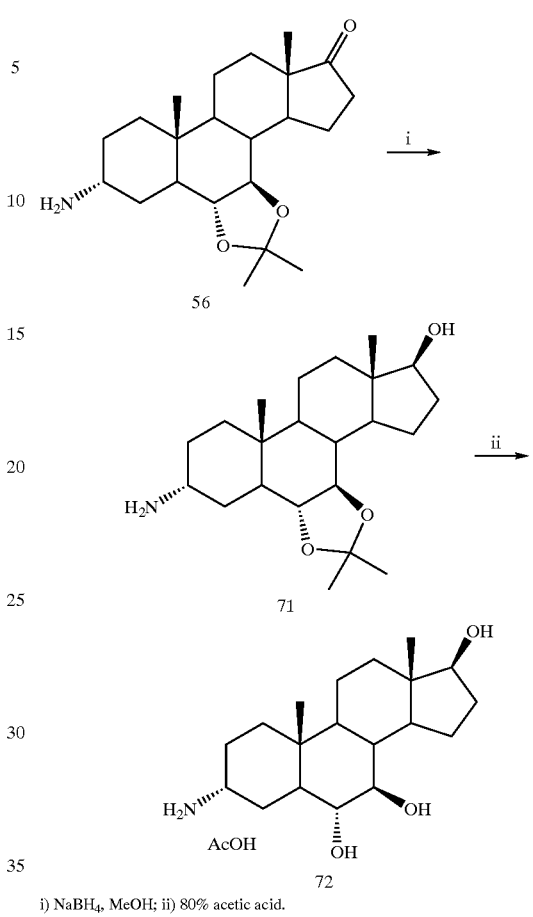

Scheme 6 i) NaBH$_4$, MeOH; ii) 80% acetic acid.

Synthesis of Compound 71

An ice cooled solution of the ketone 56 (100 mg, 0.28 mmol), NaBH$_4$ (16 mg, 0.41 mmol) and 1.4 ml of MeOH was allowed to react for 2.5 hours. The reaction was quenched by the addition of 1 ml of water and concentrated to remove most of the MeOH. The residue was diluted with 40 ml of CH$_2$Cl$_2$ and washed with 2×10 ml of brine, dried over MgSO$_4$, filtered and concentrated to give 90 mg (90%) of compound 71.

Synthesis of Compound 72

A solution of the amine 71 (90 mg, 0.25 mmol) and 2 ml of 80% acetic acid was heated at 40° C. for 2 hours. The reaction mixture was twice diluted with 10 ml of toluene and concentrated to remove residual acetic acid. The residue was dissolved in 1 ml of MeOH and 5 ml of hexanes, concentrated and dried to give 86 mg (90%) of compound 72 as a white solid. LC/MS (direct infusion, electrospray +ve, 10 mM NH$_4$OAc in 4:1 water and MeCN) 324.19; C$_{19}$H$_{34}$NO$_3$.

Example 8

Salts of 3α-Amino-6,7-dihydroxy-17-methylidene Steroid

The 6- and 7-hydroxyls can be protected using a variety of protecting groups. Suitable protecting groups are listed in Greene and Wuts, "Protective Groups in Organic Synthesis", John Wiley & Sons, New York, N.Y. (1999). Scheme 7 shows examples of analogues that have been synthesized with the 6- and 7-hydroxyls protected as methyl ethers. The starting material compound 73 for the synthesis is described in U.S. Pat. No. 6,046,185. Generation of the dianion of compound 73 using NaH in dimethylformamide followed by alkylation with methyl iodide gave compound 74. Treatment with 80% acetic acid removed both the cyclic ketal and tert-butyldimethylsilyl ether protecting groups. Olefination of compound 75 using methyltriphenylphosphonium bromide and KO$^t$Bu in THF gave the 17-methylidene compound 76. Azidation using ZnN$_6$.2py, PPh$_3$ and DIAD in toluene gave the 3α-azido compound 77. Lithium aluminum hydride reduction in THF gave the 3α-amine 78. Treatment with HCl in Et$_2$O and MeOH formed the ammonium chloride salt 79. Treatment of compound 78 with acetic acid formed the ammonium acetate salt 80.

Scheme 7

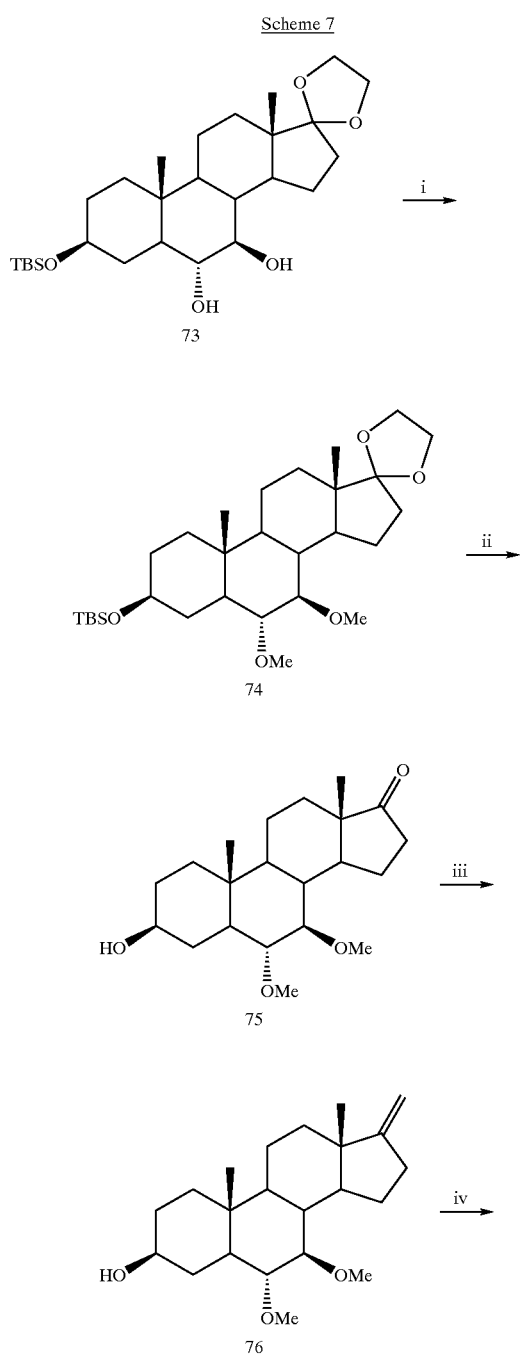

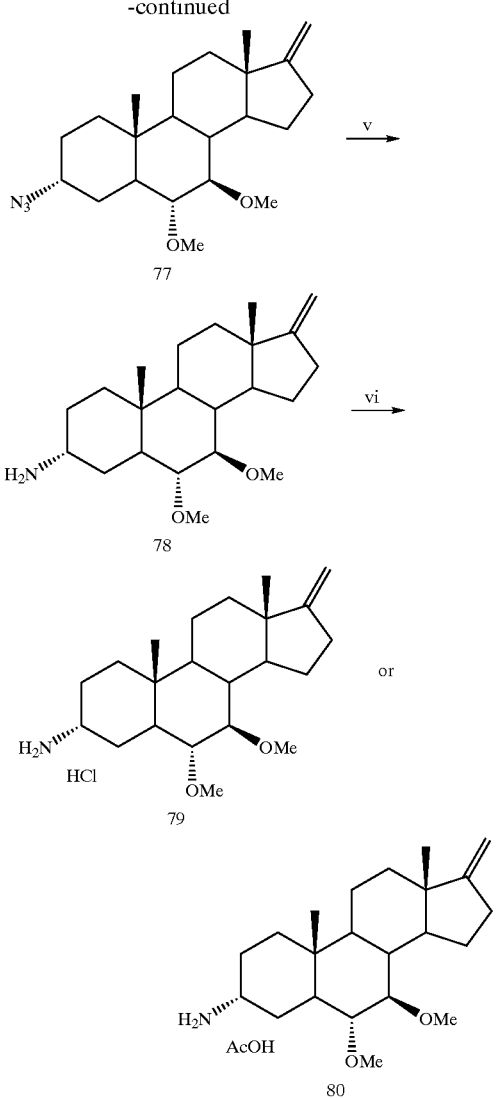

i) NaH, MeI, DMF; ii) 80% acetic acid; iii) CH$_3$PPh$_3$Br, KO$^t$Bu, THF; iv) ZnN$_6$•2Py, Ph$_3$P, DIAD, toluene; v) LiAlH$_4$, Et$_2$O; vi) HCl, Et$_2$O, MeOH; or acetic acid.

Synthesis of Compound 74

Sodium hydride (0.50 g, 12.4 mmol) was added to a room temperature solution of the diol 73 (1.49 g, 3.10 mmol) in 15 ml of DMF under nitrogen. After 2 hours the solution was cooled in ice and MeI (1.93 ml, 30.9 mmol) was added dropwise over 30 seconds. The reaction was allowed to warm to room temperature while stirring overnight. The reaction mixture was diluted with 100 ml of Et$_2$O, washed with 10 ml of water and 2×10 ml of brine, dried over MgSO$_4$, filtered and concentrated to give 1.73 g of crude compound 74 as a pale yellow oil.

Synthesis of Compound 75

A solution of crude compound 74 (1.73 g, 3.10 mmol) and 15 ml of 80% acetic acid was stirred at room temperature for 4 hours. The solution was concentrated, the residue taken up in 50 ml of EtOAc, washed with 2×20 ml of saturated NaHCO$_3$ solution and 2×10 ml of brine, dried over MgSO$_4$, filtered and concentrated to give 1.18 g of crude compound 75 as a white foam.

Synthesis of Compound 76

A solution of KO$^t$Bu (1.09 g, 9.20 mmol), MePPh$_3$Br (3.30 g, 9.20 mmol) and 15 ml of THF was stirred at room temperature under nitrogen. After 2 hours crude ketone 75 (1.17, mg, 3.08 mmol) was added to the yellow solution and the resulting solution was allowed to stir at room temperature overnight. The reaction was quenched with 2 ml of water, diluted with 100 ml of EtOAc, washed with 3×10 ml of brine, dried over $MgSO_4$, filtered and concentrated. Column chromatography eluting with 80% EtOAc/hexanes afforded 890 mg of impure compound 76 as a white solid.
Synthesis of Compound 77
DIAD (1.05 ml, 5.08 mmol) was added dropwise over 10 minutes to a room temperature solution of the 3β-alcohol 76 (885 mg, 2.54 mmol), $ZnN_6 \cdot 2py$ (585 mg, 1.90 mmol), $Ph_3P$ (1.33 g, 5.08 mmol) and toluene (25 ml) under argon. After 11 hours the reaction mixture was purified by column chromatography eluting with 15% EtOAc/hexanes to afford 594 mg (63%) of compound 77 as a crystalline solid.
Synthesis of Compound 78
Lithium aluminum hydride (0.79 ml of a 1 M solution in $Et_2O$, 0.79 mmol) was added to an ice cooled solution the azide 77 (588 mg, 1.57 mmol) in 15.7 ml of $Et_2O$ under argon. After 10 minutes the reaction was allowed to warm to room temperature while stirring overnight. After 1 hour the reaction mixture was cooled in ice and slowly quenched with 10 ml of saturated $Na_2SO_4$ solution. After 10 minutes a white precipitate had formed and the liquid was decanted off. The residue was washed with 2×25 ml of EtOAc and the washings were combined with the previously decanted ether solution. The solution was washed with 3×10 ml of brine, dried over $MgSO_4$, filtered and concentrated. Purification by column chromatography eluting with 95:5:2 $CH_2Cl_2$:MeOH:$Et_3N$ gave 434 mg (79%) of compound 78 as a white solid. LC/MS (direct infusion, electrospray +ve, 10 mM $NH_4OAc$ in 4:1 water and MeCN) 348.20; $C_{22}H_{38}NO_2$.
Synthesis of Compound 79
Hydrogen chloride (0.26 ml of a 1.0 M solution in $Et_2O$, 0.26 mmol) was added to a solution of the amine 78 (60 mg, 0.17 mmol) in 2 ml of $Et_2O$. The resulting gel-like material was dissolved in 5 ml of methanol and concentrated. The residue was dissolved in 1 ml of methanol, diluted with 5 ml of cyclohexane and concentrated to give 66 mg (100%) of compound 79 as a white solid. LC/MS (direct infusion, electrospray +ve, 10 mM $NH_4OAc$ in 4:1 water and MeCN) 348.20; $C_{22}H_{38}NO_2$.
Synthesis of Compound 80
A solution of the amine 78 (61 mg, 0.17 mmol) and 1 ml of acetic acid was allowed to stand at room temperature for 30 minutes. The solution was diluted with 5 ml of toluene and concentrated. The residue was taken up in 5 ml of hexanes, concentrated and the residue was dried for 2 hours using an Abderhalden drying apparatus with refluxing acetone to give 71 mg (100%) of compound 80 as a white solid. LC/MS (direct infusion, electrospray +ve, 10 mM $NH_4OAc$ in 4:1 water and MeCN) 348.20; $C_{22}H_{38}NO_2$.

Example 9

Salts of 3β-Amino-6,7-dihydroxy-17-methylidene Steroid

The stereochemistry at C3 can be inverted to give 3β-ammonium salt derivatives of any number of compounds related to compound 49. The stereochemistry at C3 can be inverted in 3 synthetic steps as shown in Scheme 8 for the synthesis of compounds 28 and 83. The 3β-hydroxyl compound 46 is converted to the 3β-mesylate 81 using methanesulfonyl chloride and pyridine. Heating compound 81 and cesium acetate in 100° C. DMF gives the 3α-acetate compound 82. The inversion sequence is completed by methanolysis of the acetate in compound 82 using sodium methoxide to give the 3α-hydroxyl compound 25. Treatment of compound 25 with $ZnN_6 \cdot 2py$, triphenylphosphine and DIAD in toluene produced the 3β-azido compound 26. Lithium aluminum hydride reduction of the azide in $Et_2O$ provided the 3β-amino compound 27. Treatment with HCl in THF and water removes the acetonide group and forms the ammonium chloride salt 28. Similarly, treatment of compound 27 with 80% acetic acid removes the acetonide group and forms the ammonium acetate salt 83. Using the methods outlined in Scheme 8, compound 50 is converted into compound 89 and compound 61 is converted into compound 95 (see Table 1). Compounds 26, 27, 87, 88, 89, 93, 94 and 95 are examples of compounds of the invention having 3β stereochemistry.

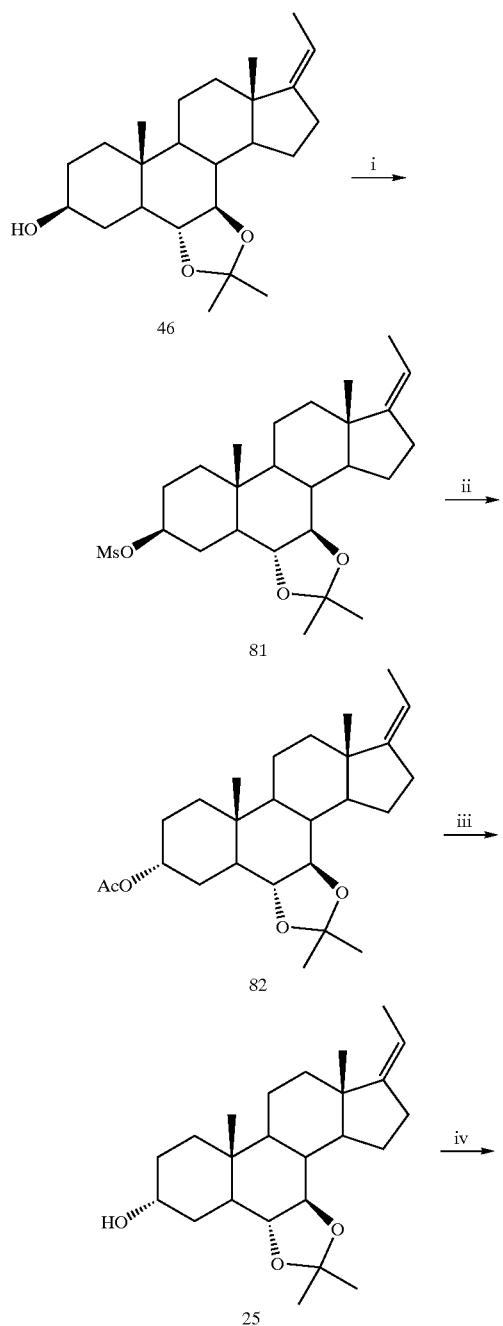

Scheme 8

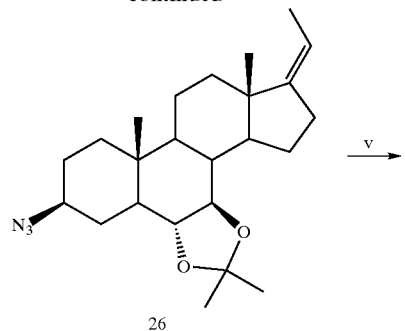

26

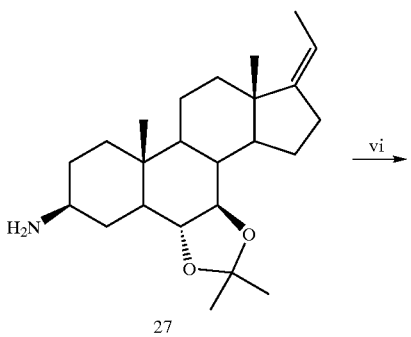

27

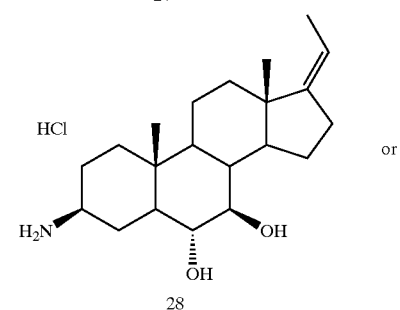

28

83 i) MsCl, pyridine; ii) CsOAc, DMF, 100° C.; iii) NaOMe, MeOH;
iv) ZnN$_6$•2py, Ph$_3$P, DIAD, toluene; v) LiAlH$_4$, Et$_2$O; vi) 4 M HCl in dioxane, THF, water or 80% acetic acid.

Synthesis of Compound 81

Methanesulfonyl chloride (1.2 ml, 16 mmol) was added to an ice cooled solution of the 3β-hydroxyl compound 46 (3.0 g, 8.0 mmol) in pyridine (20 ml) under argon. After 4 hours the solution was cooled in ice and 20 ml of saturated NaHCO$_3$ solution was added. After 15 minutes the solution was diluted with 150 ml of EtOAc and washed with 3×25 ml of brine, dried over MgSO$_4$, filtered and concentrated to give 3.6 g (100%) of compound 81 as an off-white foam.

Synthesis of Compound 82

A solution of the mesylate 81 (3.6 g, 8.0 mmol), cesium acetate (4.6 g, 24 mmol) and 40 ml of DMF was heated at 100° C. for 24 hours. The solution was diluted with 100 ml of water, extracted with 2×100 ml of Et$_2$O, washed with 2×50 ml of brine, dried over MgSO$_4$, filtered and concentrated to give approximately 3 g of crude compound 82.

Synthesis of Compound 25

A solution of Na (398 mg, 17.3 mmol) in MeOH (21.5 ml) was added to the 3α-acetate 82 (1.8 g, 4.3 mmol) in THF (10 ml). After 2 hours, 20 ml of water was added and the resulting solution was diluted with 100 ml of EtOAc, washed consecutively with saturated NaHCO$_3$ solution, water and brine, dried over MgSO$_4$, filtered and concentrated to give 1.58 g (98%) of crude compound 25 as a yellow foam.

Synthesis of Compound 26

DIAD (1.70 ml, 8.24 mmol) was added dropwise over 10 minutes to a room temperature solution of the 3α-alcohol 25 (1.54 g, 4.12 mmol), ZnN$_6$.2py (0.94 g, 3.09 mmol), Ph$_3$P (2.16 g, 8.24 mmol) and toluene (44 ml) under argon. After stirring overnight, the reaction mixture was loaded onto a column of silica gel packed in 10% EtOAc/hexanes and eluted with 10% EtOAc/hexanes to afford 0.89 g (61%) of compound 26 as a white solid.

Synthesis of Compound 27

Lithium aluminum hydride (146 mg, 3.66 mmol) was added to an ice cooled solution the azide 26 (1.46 g, 3.66 mmol) in 18.3 ml of Et$_2$O under argon. The reaction was allowed to warm to room temperature. After 1.5 hours the solution was cooled in ice, diluted with 25 ml of Et$_2$O and slowly quenched with 20 ml of saturated Na$_2$SO$_4$ solution. After 10 minutes a white precipitate had formed and the solution was diluted with 50 ml of EtOAc, washed with 3×10 ml of brine, dried over MgSO$_4$, filtered and concentrated to give 1.31 g (96%) of compound 27 as a white foam.

Synthesis of Compound 28

A solution of the 3β-amino compound 27 (227 mg, 0.609 mmol), 4 M HCl in dioxane (183 µl, 0.73 mmol), THF (9.7 ml) and water (2.4 ml) was stirred at room temperature overnight. Evaporated the THF and water, took up the residue in 5 ml of methanol and concentrated, triturated with 5 ml of acetone, concentrated to give 224 mg (100%) of compound 28 as a white solid. LC/MS (direct infusion, electrospray +ve, 10 mM NH$_4$OAc in 4:1 water and MeCN) 334.10; C$_{21}$H$_{36}$NO$_2$.

Synthesis of Compound 83

A solution of the amine 27 (412 mg, 1.10 mmol) and 5 ml of 80% acetic acid was stirred at room temperature for 4 hours. The reaction mixture was diluted with 5 ml of toluene then concentrated. The residue was twice more taken up in 5 ml portions of toluene and concentrated to remove residual acetic acid. The residue was twice triturated in 10 ml of CH$_2$Cl$_2$ and concentrated to give 430 mg (99%) of compound 83 as a white solid. LC/MS (direct infusion, electrospray +ve, 10 mM NH$_4$OAc in 4:1 water and MeCN) 334.19; C$_{21}$H$_{36}$NO$_2$.

Synthesis of Compound 84

Methanesulfonyl chloride (0.33 ml, 4.2 mmol) was added to an ice cooled solution of the 3β-hydroxyl compound 50 (754 mg, 2.09 mmol) in pyridine (5.3 ml) under argon. After 4 hours the solution was cooled in ice and 5 ml of saturated NaHCO$_3$ solution was added. After 15 minutes the solution was diluted with 60 ml of ethyl acetate and washed with 3 times with brine, dried over MgSO$_4$, filtered and concentrated to give 860 mg (94%) of compound 84 as an off-white solid.

Synthesis of Compound 85

A solution of the mesylate 84 (860 mg, 1.96 mmol), cesium acetate (1.13 g, 5.88 mmol) and 10 ml of DMF was heated at 95° C. for 32 hours. The solution was diluted with 50 ml of water, extracted with 2×100 ml of Et$_2$O, washed with 2×30 ml of brine, dried over MgSO$_4$, filtered and concentrated. Purification by column chromatography eluting with 5% and 8% EtOAc/Hexanes afforded 558 mg (71%) of compound 85 as white solid.

Synthesis of Compound 86

A solution of Na (128 mg, 5.56 mmol) in MeOH (7 ml) was added to the 3α-acetate 85 (558 mg, 1.38 mmol). After 2 hours 5 ml of saturated NaHCO$_3$ solution was added and the resulting solution was diluted with 100 ml of EtOAc. The solution washed with 2×20 ml of water and 2×20 ml of brine, dried over MgSO$_4$, filtered and concentrated to give 491 mg (99%) of compound 86 as a white solid.

Synthesis of Compound 87

DIAD (0.57 ml, 2.74 mmol) was added dropwise over 15 minutes to a room temperature solution of the 3α-hydroxy compound 86 (493 mg, 1.37 mmol), ZnN$_6$.2py (315 mg, 1.03 mmol), Ph$_3$P (718 mg, 2.74 mmol) and toluene (13.7 ml) under argon. After 3.5 hours the reaction mixture was loaded onto a column of silica gel packed in 10% ethyl acetate/hexanes and eluted with 10% ethyl acetate/hexanes to afford 390 mg (74%) of compound 87 as a viscous oil.

Synthesis of Compound 88

Lithium aluminum hydride (40 mg, 1.01 mmol) was added to an ice cooled solution of the azido compound 87 (390 mg, 1.01 mmol) in 5 ml of diethyl ether under argon. The reaction was allowed to warm to room temperature. After 2 hours the solution was cooled in ice, diluted with 25 ml of diethyl ether and slowly quenched with 2 ml of saturated Na$_2$SO$_4$ solution. After 10 minutes a white precipitate had formed and the solution was diluted with 40 ml of ethyl acetate, washed with 3×15 ml of brine, dried over MgSO$_4$, filtered and concentrated. The crude material was purified using a column of silica gel prepared by packing in 1% Et$_3$N/CH$_2$Cl$_2$ and washing with 5% MeOH/CH$_2$Cl$_2$. The crude material was loaded in CH$_2$Cl$_2$, eluted with 5% MeOH/CH$_2$Cl$_2$ and then 95:5:2 CH$_2$Cl$_2$:MeOH:Et$_3$N to give 277 mg (76%) of compound 88 as a white solid.

Synthesis of Compound 89

A solution of the amino compound 88 (270 mg, 0.752 mmol) and 10 ml of 80% acetic acid was heated at 40° C. for 1 hour. The reaction mixture was concentrated to give a white foam. Acetone (10 ml) was added and sonicated to dissolve the material and then evaporated. Another 10 ml portion of acetone was added, sonicated and evaporated to give 285 mg (100%) of compound 89 as a white solid. LC/MS (direct infusion, electrospray +ve, 10 mM NH$_4$OAc in 4:1 water and MeCN) 320.26; C$_{20}$H$_{34}$NO$_2$.

Synthesis of Compound 90

Methanesulfonyl chloride (0.20 ml, 2.56 mmol) was added to an ice cooled solution of the 3β-hydroxyl compound 61 (501 mg, 1.28 mmol) in pyridine (3.2 ml) under argon. After 4 hours the solution was cooled in ice and 5 ml of saturated NaHCO$_3$ solution was added. After 15 minutes the solution was diluted with 50 ml of EtOAc and washed 3 times with brine, dried over MgSO$_4$, filtered and concentrated to give 590 mg (98%) of compound 90 as a white foam.

Synthesis of Compound 91

A solution of the mesylate 90 (590 mg, 1.25 mmol), cesium acetate (722 mg, 3.76 mmol) and 6.2 ml of DMF was heated at 100° C. for 24 hours. The solution was diluted with 50 ml of water, extracted with 2×50 ml of Et$_2$O, washed with 2×30 ml of brine, dried over MgSO$_4$, filtered and concentrated. Purification by column chromatography eluting with 8% EtOAc/hexanes afforded 297 mg (55%) of compound 91 as a white solid.

Synthesis of Compound 92

A solution of Na (63 mg, 2.7 mmol) in MeOH (3.4 ml) was added to the 3α-acetate 91 (297 mg, 0.684 mmol) in THF (1 ml). The solution was stirred overnight, 5 ml of water and 80 ml of EtOAc were added and washed twice with water and twice with brine, dried over MgSO$_4$, filtered and concentrated to give 251 mg (94%) of compound 92 as a white solid.

Synthesis of Compound 93

DIAD (0.26 ml, 1.24 mmol) was added dropwise over 10 minutes to a room temperature solution of the 3α-alcohol 92 (243 mg, 0.620 mmol), ZnN$_6$.2py (143 mg, 0.465 mmol), Ph$_3$P (325 mg, 1.24 mmol) and toluene (6.2 ml) under argon. After 4 hours the reaction mixture was loaded onto a column of silica gel packed in 10% EtOAc/hexanes and eluted with 20% EtOAc/hexanes to afford 209 mg of impure compound 93 as a yellow oil.

Synthesis of Compound 94

Lithium aluminum hydride (20 mg, 0.50 mmol) was added to an ice cooled solution the impure azide 93 (209 mg, 0.50 mmol) in 5 ml of Et$_2$O under argon. The reaction was allowed to warm to room temperature. After 4 hours the solution was cooled in ice, diluted with 25 ml of Et$_2$O and slowly quenched with 2 ml of saturated Na$_2$SO$_4$ solution. After 10 minutes a white precipitate had formed and the solution was diluted with 50 ml of EtOAc, washed with 3×10 ml of brine, dried over MgSO$_4$, filtered and concentrated. The crude material was chromatographed using a column of silica gel prepared by packing in 1% Et$_3$N/CH$_2$Cl$_2$ and washing with 5% MeOH/CH$_2$Cl$_2$. The crude material was loaded in CH$_2$Cl$_2$, eluted with 5% MeOH/CH$_2$Cl$_2$ and then 95:5:2 CH$_2$Cl$_2$:MeOH:Et$_3$N to give 97 mg of impure compound 94 as a white solid.

Synthesis of Compound 95

A solution of the impure 3β-amino compound 94 (97 mg, 0.25 mmol), 4 M HCl in dioxane (74 μl, 0.30 mmol), THF (4 ml) and water (1 ml) was stirred at room temperature. After 4 hours the solution was concentrated, the residue was taken up in 5 ml of methanol and concentrated. The residue was twice triturated with 5 ml of acetone and concentrated. The white solid was dissolved in approximately 0.5 ml of water and acetone (5 ml) was slowly added until crystals appeared. The crystals were filtered, rinsed with acetone and dried to give 66 mg of compound 95 as colorless fine needles. LC/MS (direct infusion, electrospray +ve, 10 mM NH$_4$OAc in 4:1 water and MeCN) 352.09; C$_{21}$H$_{35}$FNO$_2$.

Example 10

3-Amino-6,7-dihydroxy-17-alkyl Steroid

Any compounds having the 17(20)-alkenyl functionality can have the double bond hydrogenated using H$_2$ in the presence of a catalyst such as 10% Pd on carbon. For example compound 96 has been prepared from compound 28 as shown in Scheme 9. Similarly, compound 97 was prepared from compound 49 using the same methodology as shown in Scheme 9 (see Table 2).

Scheme 9

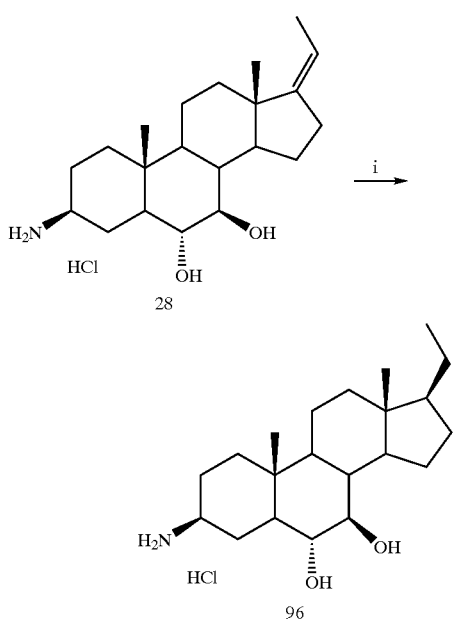

i) H₂, Pd on carbon, methanol.

Synthesis of Compound 96

A solution of the olefin 28 (52 mg, 0.14 mmol), 10% Pd on carbon (15 mg, 0.014 mmol) and methanol (3 ml) was stirred at room temperature overnight under hydrogen. The solution was filtered through celite eluting with 50 ml of methanol and concentrated to give 50 mg (96%) of compound 96 as a white solid. LC/MS (direct infusion, electrospray +ve, 10 mM NH₄OAc in 4:1 water and MeCN) 336.24; $C_{21}H_{38}NO_2$.

Synthesis of Compound 97

A solution of the olefin 49 (844 mg, 2.28 mmol), 10% Pd on carbon (243 mg, 0.228 mmol) and methanol (11 ml) was stirred at room temperature overnight under hydrogen. The solution was filtered through celite eluting with 50 ml of methanol and concentrated. The residue was triturated in 10 ml of acetone, filtered and dried to give 801 mg (94%) of compound 97 as a white solid. LC/MS (direct infusion, electrospray +ve, 10 mM NH₄OAc in 4:1 water and MeCN) 336.21; $C_{21}H_{38}NO_2$.

Example 11

3-Secondary Amino-6,7-dihydroxy-17-methylidene Steroid

Any amine related to compound 52 can be coupled to an aldehyde or ketone to prepare secondary or tertiary amines. Reaction of compound 52 with a solution of 4-isopropylbenzaldehyde and titanium isopropoxide in THF followed by reduction with sodium borohydride gives compound 99. Treatment with 80% acetic acid removes the acetonide group and forms the ammonium acetate salt 100. Example compounds 101–107 were synthesized using the methods outlined in Scheme 10 (see Table 6).

Scheme 10

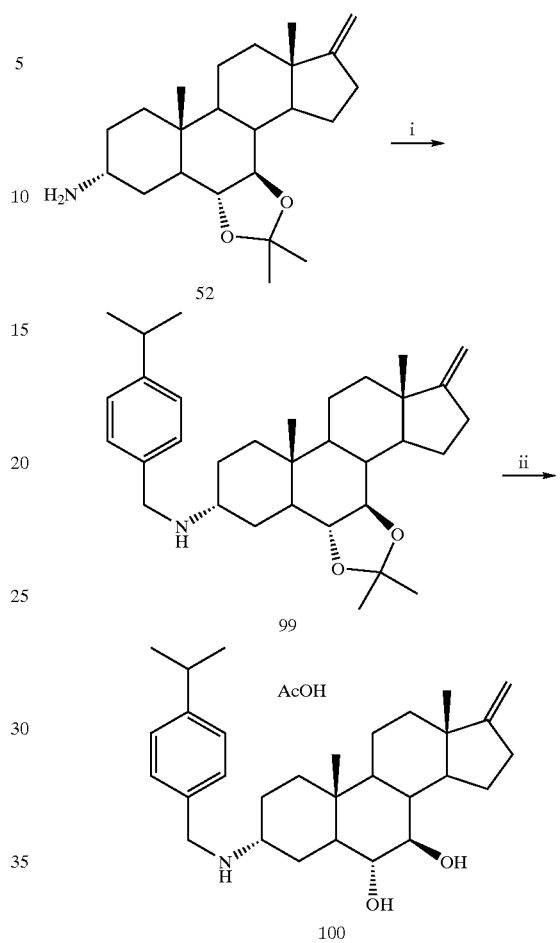

i) 4-isopropylbenzaldehyde, Ti(O$^i$Pr)₄, THF; NaBH₄, MeOH; ii) 80% acetic acid.

Synthesis of Compound 99

Titanium(IV) isopropoxide (120 μl, 0.42 mmol) was added to a room temperature solution of the amine 52 (100 mg, 0.28 mmol), 4-isopropylbenzaldehyde (46 μl, 0.31 mmol) and 1.4 ml of THF under nitrogen. After 12 hours a solution of NaBH₄ (29 mg, 0.78 mmol) in 1 ml of EtOH was added and the reaction was continued for another 8 hours. The reaction was quenched by the addition of 3 ml of brine, diluted with 30 ml of EtOAc, separated, washed with 10 ml of brine, dried over MgSO₄, filtered and concentrated. Purification using radial chromatography afforded 50 mg (36%) of compound 99.

Synthesis of Compound 100

A solution of the amine 99 (50 mg, 0.10 mmol) and 1 ml of 80% acetic acid was heated at 40° C. for 3 hours. The reaction mixture was twice taken up in 5 ml portions of toluene and concentrated and then once each with acetone and hexanes to give 25 mg (51%) of compound 100. LC/MS (direct infusion, electrospray +ve, 10 mM NH₄OAc in 4:1 water and MeCN) 452.27; $C_{30}H_{46}NO_2$.

Synthesis of Compound 101

Using the procedure described for the synthesis of compound 99, the amine 52 (100 mg, 0.28 mmol) was reacted with 2-fluorobenzaldehyde (32 μl, 0.32 mmol) to give 43 mg of amine intermediate. The amine intermediate was treated with 1 ml of 80% acetic acid at 40° C. for 3 hours. The reaction mixture was diluted with 5 ml of toluene and concentrated. The residue was dissolved in 1 ml of acetone, diluted with 5 ml of hexanes and concentrated to give 49 mg (37%) of compound 101 as a white solid. LC/MS (direct infusion, electrospray +ve, 10 mM NH$_4$OAc in 4:1 water and MeCN) 428.22; $C_{27}H_{39}FNO_2$.

Synthesis of Compound 102

Using the procedure described for the synthesis of compound 99, the amine 52 (100 mg, 0.28 mmol) was reacted with 3-(trifluoromethyl)benzaldehyde (41 µl, 0.31 mmol) to give 61 mg of amine intermediate. The amine intermediate was treated with 1 ml of 80% acetic acid at 40° C. for 3 hours. The reaction mixture was diluted with 5 ml of toluene and concentrated. The residue was dissolved in 1 ml of acetone, diluted with 5 ml of hexanes and concentrated to give 64 mg (45%) of compound 102 as a white solid. LC/MS (direct infusion, electrospray +ve, 10 mM NH$_4$OAc in 4:1 water and MeCN) 478.18; $C_{28}H_{39}F_3NO_2$.

Synthesis of Compound 103

Using the procedure described for the synthesis of compound 99, the amine 52 (100 mg, 0.28 mmol) was reacted with o-anisaldehyde (42 mg, 0.31 mmol) to give 30 mg of amine intermediate. The amine intermediate was treated with 1 ml of 80% acetic acid at 40° C. for 3 hours. The reaction mixture was diluted with 5 ml of toluene and concentrated. The residue was dissolved in 1 ml of acetone, diluted with 5 ml of hexanes and concentrated to give 18 mg (14%) of compound 103. LC/MS (direct infusion, electrospray +ve, 10 mM NH$_4$OAc in 4:1 water and MeCN) 440.23; $C_{28}H_{42}NO_3$.

Synthesis of Compound 104

Using the procedure described for the synthesis of compound 99, the amine 52 (100 mg, 0.28 mmol) was reacted with 4-(trifluoromethoxy)benzaldehyde (44 µl, 0.31 mmol) to give 86 mg of amine intermediate. The amine intermediate was treated with 1.5 ml of 80% acetic acid at 40° C. for 3 hours. The reaction mixture was diluted with 5 ml of toluene and concentrated. The residue was dissolved in 1 ml of acetone, diluted with 5 ml of hexanes and concentrated to give 84 mg (57%) of compound 104 as a white solid. LC/MS (direct infusion, electrospray +ve, 10 mM NH$_4$OAc in 4:1 water and MeCN) 494.15; $C_{28}H_{39}F_3NO_3$.

Synthesis of Compound 105

Using the procedure described for the synthesis of compound 99, the amine 52 (100 mg, 0.28 mmol) was reacted with 3-phenoxybenzaldehyde (60 mg, 0.32 mmol) to give 73 mg of amine intermediate. The amine intermediate was treated with 1 ml of 80% acetic acid at 40° C. for 3 hours. The reaction mixture was diluted with 5 ml of toluene and concentrated. The residue was dissolved in 1 ml of acetone, diluted with 5 ml of hexanes and concentrated to give 87 mg (58%) of compound 105 as a white solid. LC/MS (direct infusion, electrospray +ve, 10 mM NH$_4$OAc in 4:1 water and MeCN) 502.20; $C_{33}H_{44}NO_3$.

Synthesis of Compound 106

Using the procedure described for the synthesis of compound 99, the amine 52 (100 mg, 0.28 mmol) was reacted with 3-nitrobenzaldehyde (46 mg, 0.31 mmol) to give 18 mg of amine intermediate. The amine intermediate was treated with 1 ml of 80% acetic acid at 40° C. for 3 hours. The reaction mixture was diluted with 5 ml of toluene and concentrated. The residue was dissolved in 1 ml of acetone, diluted with 5 ml of hexanes and concentrated to give 18 mg (14%) of compound 106 as an off-white solid. LC/MS (direct infusion, electrospray +ve, 10 mM NH$_4$OAc in 4:1 water and MeCN) 455.20; $C_{27}H_{39}N_2O_4$.

Synthesis of Compound 107

Using the procedure described for the synthesis of compound 99, the amine 52 (200 mg, 0.55 mmol) was reacted with 3-pyridylcarboxaldehyde (82 µl, 0.61 mmol) to give 100 mg of amine intermediate. A suspension of the amine intermediate, 4 M HCl in dioxane (65 µl, 0.26 mmol), 110 µl of water and 2.2 ml of acetonitrile was stirred at room temperature for 1 hour. The solution was filtered and the solid was dried to afford 77 mg (30%) of compound 107 as a white solid. LC/MS (direct infusion, electrospray +ve, 10 mM NH$_4$OAc in 4:1 water and MeCN) 411.21; $C_{26}H_{39}N_2O_2$.

Example 12

3-Cycloamino-6,7-dihydroxy-17-ethylidene Steroid

Any ketone related to compound 108 may be coupled to an amine using the methodology shown in Scheme 11. The starting material compound 108 for the synthesis is described in U.S. Pat. No. 6,046,185. Reaction of compound 108 with piperidine and sodium cyanoborohydride in methanol gave compound 109 as a mixture of isomers at C3. Treatment with 80% acetic acid removed the acetonide protecting group and formed the ammonium acetate salt 110. Example compound 111 was synthesized using the methods outlined in Scheme 11, except hydrochloric acid is used in place of acetic acid (see Table 5). A 3-cycloamino group is a group attached to the 3-position, where the carbon at the 3-position is attached directly to a nitrogen, and this nitrogen is part of a heterocyclic ring.

Scheme 11

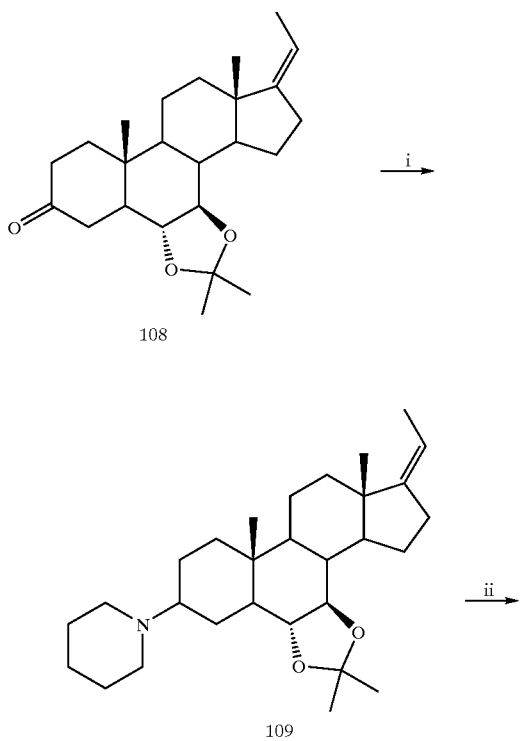

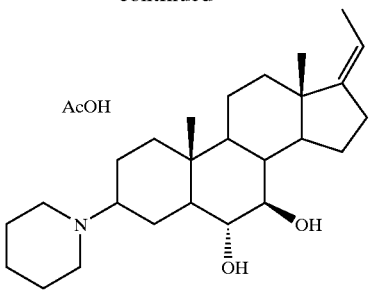

110 i) piperidine, Ti(O$^i$Pr)$_4$, THF; NaBH$_4$, MeOH; ii) 80% acetic acid.

Synthesis of Compound 109

A solution of the ketone 108 (200 mg, 0.54 mmol), piperidine (266 µl, 2.68 mmol), 100 mg of 3 Å molecular sieves, NaBH$_3$CN (24 mg, 0.38 mmol) and 5.4 ml of MeOH was stirred at room temperature for 24 hours. The reaction mixture was diluted with 20 ml of water and extracted with 2×20 ml of CH$_2$Cl$_2$. The combined extractions were washed with 10 ml of brine, dried over MgSO$_4$, filtered and concentrated. The crude material was purified using radial chromatography eluting with 20% MeOH/CH$_2$Cl$_2$ to afford 112 mg (47%) of compound 109 as a white solid.

Synthesis of Compound 110

A solution of the amines 109 (102 mg, 0.23 mmol) and 5 ml of 80% acetic acid was heated at 40° C. for 1 hour. The solution was concentrated, the residue was taken up in 2 ml of MeOH, diluted with 15 ml of toluene and concentrated. The residue was triturated in 5 ml of acetone, filtered and dried to give 44 mg (42%) of compound 110 as a white solid. LC/MS (direct infusion, electrospray +ve, 10 mM NH$_4$OAc in 4:1 water and MeCN) 402.31; C$_{26}$H$_{44}$NO$_2$.

Synthesis of Compound 111

Using the procedure described for the synthesis of compound 109, the ketone 108 (200 mg, 0.54 mmol) was reacted with morpholine (234 µl, 2.68 mmol) to give 56 mg of the amine intermediate. The amine intermediate was treated with 5 ml of 80% acetic acid at 40° C. for 1 hour. The solution was concentrated, dissolved in 5 ml of MeOH and concentrated. $^1$H and $^{13}$C NMR analyses indicated the acetonide protecting group had been removed but little or none of the salt had formed. The material was treated with 4 M HCl in dioxane (32 µl, 0.13 mmol) and 2 ml of acetone giving a white precipitate. The suspension was diluted with 2 ml of acetone, filtered and dried to give 48 mg (20%) of compound 111 as a white solid. LC/MS (direct infusion, electrospray +ve, 10 mM NH$_4$OAc in 4:1 water and MeCN) 404.20; C$_{25}$H$_{42}$NO$_3$.

Example 13

3-Oxo to 3-Secondary Amino Conversion in Steroid

Any ketone related to compound 108 can be coupled to an amine using the methodology shown in Scheme 12. Methylamine is added to a solution of compound 108 and titanium isopropoxide in THF, followed by reduction with sodium borohydride. The solution is filtered and eluted through MP-TsOH resin to give compound 112, as a mixture of isomers at C3. Treatment with HCl in acetonitrile and water formed the ammonium chloride salt 113. Example compounds 114–129 were synthesized using the methods outlined in Scheme 12, except that acetic acid was used in place of hydrochloric acid for the examples in which ammonium acetate salts were formed (see Table 5).

Scheme 12

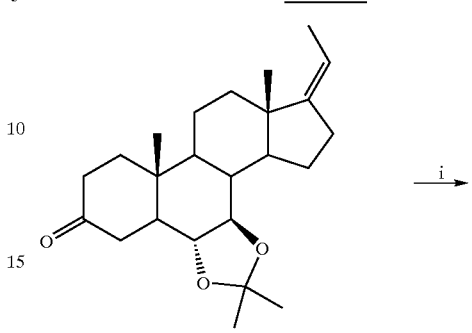

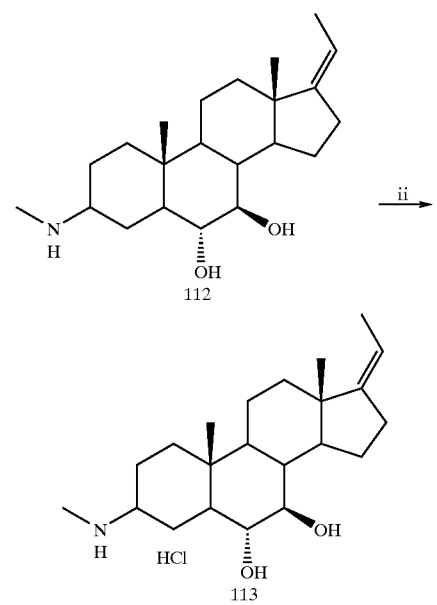

i) methylamine hydrochloride, Ti(O$^i$Pr)$_4$, THF; NaBH$_4$, MeOH; ii) HCl, water, acetonitrile.

Synthesis of Compound 112

Titanium(IV) isopropoxide (270 µl, 0.92 mmol) was added to a room temperature solution of the ketone 108 (250 mg, 0.67 mmol), methylamine hydrochloride (41 mg, 0.61 mmol) and 1.5 ml of THF under nitrogen. After 12 hours a solution of NaBH$_4$ (65 mg, 1.7 mmol) in 2.3 ml of EtOH was added and the reaction was continued for another 10 hours. The reaction was quenched by the addition of 0.5 ml of water and filtered to remove a white precipitate. The solution was loaded onto a column of 600 mg of MP-TsOH resin and eluted with 3 ml of MeOH then 4 ml of 2 M NH$_3$ in MeOH. The NH$_3$/MeOH fraction was concentrated to give 76 mg (32%) of compound 112.

Synthesis of Compound 113

A suspension of compound 112 (76 mg, 0.21 mmol), 4 M HCl in dioxane (75 µl, 0.30 mmol), 50 µl of water and 1 ml of acetonitrile was stirred at room temperature for 1 hour. The solution was filtered and the solid was dried to afford 38 mg (13%) of compound 113 as a grey solid. LC/MS (direct infusion, electrospray +ve, 10 mM NH$_4$OAc in 4:1 water and MeCN) 348.19; C$_{22}$H$_{38}$NO$_2$.

Synthesis of Compound 114

Using the procedures described for the synthesis of compound 112, the ketone 108 (200 mg, 0.53 mmol) was reacted with propylamine hydrochloride (47 mg, 0.49 mmol) to give 72 mg of amine intermediate. The amine intermediate was treated with 75 µl of the HCl solution to give 34 mg (17%) of compound 114. LC/MS (direct infusion, electrospray +ve, 10 mM NH$_4$OAc in 4:1 water and MeCN) 376.22; C$_{24}$H$_{42}$NO$_2$.

Synthesis of Compound 115

Using the procedures described for the synthesis of compound 112, the ketone 108 (250 mg, 0.67 mmol) was reacted with amylamine (70 µl, 0.61 mmol) to give 82 mg of amine intermediate. The amine intermediate was treated with 75 µl of the HCl solution to give 75 mg (28%) of compound 115 as a white solid. LC/MS (direct infusion, electrospray +ve, 10 mM NH$_4$OAc in 4:1 water and MeCN) 404.28; C$_{26}$H$_{46}$NO$_2$.

Synthesis of Compound 116

Using the procedures described for the synthesis of compound 112, the ketone 108 (250 mg, 0.67 mmol) was reacted with cyclopentylamine (60 µl, 0.61 mmol) to give 99 mg of amine intermediate. The amine intermediate was treated with 200 µl of acetic acid for 1 hour and was twice taken up and concentrated from 1 ml portions of toluene. The residue was triturated in 1 ml of cyclohexane, filtered and dried to give 98 mg (35%) of compound 116. LC/MS (direct infusion, electrospray +ve, 10 mM NH$_4$OAc in 4:1 water and MeCN) 402.27; C$_{26}$H$_{44}$NO$_2$.

Synthesis of Compound 117

Using the procedures described for the synthesis of compound 112, the ketone 108 (250 mg, 0.67 mmol) was reacted with cyclohexylamine (70 µl, 0.61 mmol) to give 120 mg of amine intermediate. The amine intermediate was treated with 0.5 ml of acetic acid for 1 hour and was twice taken up and concentrated from 1 ml portions of toluene. The residue was triturated in 1 ml of cyclohexane, filtered and dried to give 101 mg (32%) of compound 117. LC/MS (direct infusion, electrospray +ve, 10 mM NH$_4$OAc in 4:1 water and MeCN) 416.25; C$_{27}$H$_{46}$NO$_2$.

Synthesis of Compound 118

Using the procedures described for the synthesis of compound 112, the ketone 108 (250 mg, 0.67 mmol) was reacted with pyrrolidine (51 µl, 0.61 mmol) to give 70 mg of amine intermediate. The amine intermediate was treated with 50 µl of acetic acid for 1 hour and 1 ml of cyclohexane was added to give a solid, which was filtered and dried to afford 65 mg (22%) of compound 118. LC/MS (direct infusion, electrospray +ve, 10 mM NH$_4$OAc in 4:1 water and MeCN) 388.28; C$_{25}$H$_{42}$NO$_2$.

Synthesis of Compound 119

Using the procedures described for the synthesis of compound 112, the ketone 108 (200 mg, 0.53 mmol) was reacted with N-propylethylenediamine (60 µl, 0.49 mmol) to give 99 mg of amine intermediate. The amine intermediate was treated with 75 µl of the HCl solution to give 47 mg (20%) of compound 119. LC/MS (direct infusion, electrospray +ve, 10 mM NH$_4$OAc in 4:1 water and MeCN) 419.32; C$_{26}$H$_{47}$N$_2$O$_2$.

Synthesis of Compound 120

Using the procedures described for the synthesis of compound 112, the ketone 108 (250 mg, 0.67 mmol) was reacted with N,N-dimethylethylenediamine (65 µl, 0.61 mmol) to give 93 mg of amine intermediate. The amine intermediate was treated with 75 µl of the HCl solution to give 77 mg (29%) of compound 120 as a white solid. LC/MS (direct infusion, electrospray +ve, 10 mM NH$_4$OAc in 4:1 water and MeCN) 405.28; C$_{25}$H$_{45}$N$_2$O$_2$.

Synthesis of Compound 121

Using the procedures described for the synthesis of compound 112, the ketone 108 (250 mg, 0.67 mmol) was reacted with piperazine (52 mg, 0.61 mmol) to give 33 mg of amine intermediate. The amine intermediate was treated with 200 µl of acetic acid for 1 hour and was twice taken up and concentrated from 1 ml portions of toluene. The residue was triturated in 1 ml of cyclohexane, filtered and dried to give 39 mg (14%) of compound 121. LC/MS (direct infusion, electrospray +ve, 10 mM NH$_4$OAc in 4:1 water and MeCN) 403.23; C$_{25}$H$_{43}$N$_2$O$_2$.

Synthesis of Compound 122

Using the procedures described for the synthesis of compound 112, the ketone 108 (250 mg, 0.67 mmol) was reacted with ethanolamine (33 µl, 0.61 mmol) to give 136 mg of amine intermediate. The amine intermediate was treated with 75 µl of the HCl solution to give 124 mg (50%) of compound 122 as a white solid. LC/MS (direct infusion, electrospray +ve, 10 mM NH$_4$OAc in 4:1 water and MeCN) 378.19; C$_{23}$H$_{40}$NO$_3$.

Synthesis of Compound 123

Using the procedures described for the synthesis of compound 112, the ketone 108 (250 mg, 0.67 mmol) was reacted with 5-amino-1-pentanol (63 mg, 0.61 mmol) to give 129 mg of amine intermediate. The amine intermediate was treated with 75 µl of the HCl solution to give 65 mg (24%) of compound 123 as a white solid. LC/MS (direct infusion, electrospray +ve, 10 mM NH$_4$OAc in 4:1 water and MeCN) 420.25; C$_{26}$H$_{46}$NO$_3$.

Synthesis of Compound 124

Using the procedures described for the synthesis of compound 112, the ketone 108 (250 mg, 0.67 mmol) was reacted with 2-(2-aminoethylamino)ethanol (62 µl, 0.61 mmol) to give 90 mg of amine intermediate. The amine intermediate was treated with 75 µl of the HCl solution to give 79 mg (28%) of compound 124 as a white solid. LC/MS (direct infusion, electrospray +ve, 10 mM NH$_4$OAc in 4:1 water and MeCN) 421.24; C$_{25}$H$_{45}$N$_2$O$_3$.

Synthesis of Compound 125

Using the procedures described for the synthesis of compound 112, the ketone 108 (200 mg, 0.53 mmol) was reacted with m-toluidine (52 µl, 0.49 mmol) to give 95 mg of amine intermediate. The amine intermediate was treated with 75 µl of the HCl solution to give 43 mg (19%) of compound 125. LC/MS (direct infusion, electrospray +ve, 10 mM NH$_4$OAc in 4:1 water and MeCN) 424.23; C$_{28}$H$_{42}$NO$_2$.

Synthesis of Compound 126

Using the procedures described for the synthesis of compound 112, the ketone 108 (250 mg, 0.67 mmol) was reacted with 4-aminophenol (67 mg, 0.61 mmol) to give 138 mg of amine intermediate. The amine intermediate was treated with 75 µl of the HCl solution to give 41 mg (14%) of compound 126. LC/MS (direct infusion, electrospray +ve, 10 mM NH$_4$OAc in 4:1 water and MeCN) 426.18; C$_{27}$H$_{40}$NO$_3$.

Synthesis of Compound 127

Using the procedures described for the synthesis of compound 112, the ketone 108 (250 mg, 0.67 mmol) was reacted with sulfanilamide (105 mg, 0.61 mmol) to give, after purification using radial chromatography, 24 mg of amine intermediate. The amine intermediate was treated with 75 µl of the HCl solution to give 23 mg (7%) of compound 127. LC/MS (direct infusion, electrospray +ve, 10 mM NH$_4$OAc in 4:1 water and MeCN) 489.17; C$_{27}$H$_{41}$N$_2$O$_4$S.

Synthesis of Compound 128

Using the procedures described for the synthesis of compound 112, the ketone 108 (250 mg, 0.67 mmol) was reacted with 3-aminomethylpyridine (62 µl, 0.61 mmol) to give 108 mg of amine intermediate. The amine intermediate was reacted with 1 ml of 80% acetic acid at 40° C. for 1 hour. The reaction mixture was concentrated and was twice taken up and concentrated from 1 ml portions of toluene. The residue was triturated in 1 ml of cyclohexane, filtered and dried to give 117 mg (41%) of compound 128. LC/MS (direct infusion, electrospray +ve, 10 mM NH$_4$OAc in 4:1 water and MeCN) 425.24; C$_{27}$H$_{41}$N$_2$O$_2$.

Synthesis of Compound 129

Using the procedures described for the synthesis of compound 112, the ketone 108 (250 mg, 0.67 mmol) was reacted with histamine (68 mg, 0.61 mmol) to give 120 mg of amine intermediate. The amine intermediate was reacted with 1 ml of 80% acetic acid at 40° C. for 1 hour. The reaction mixture was concentrated and was twice taken up and concentrated from 1 ml portions of toluene. The residue was triturated in 1 ml of cyclohexane, filtered and dried to give 128 mg (38%) of compound 129. LC/MS (direct infusion, electrospray +ve, 10 mM NH$_4$OAc in 4:1 water and MeCN) 428.23; C$_{26}$H$_{42}$N$_3$O$_2$.

Example 14

3-Amino to 3-Acylamino Conversion in Steroid

Amide and sulfonamide analogues can be prepared from any amine related to compound 52. Scheme 13 shows the synthesis of the amide 131. Acetylation of the amine 52 in CH$_2$Cl$_2$, using acetyl chloride using acetyl chloride and resin bound diethylamine gave the amide 130. Treatment with 80% acetic acid removed the acetonide group giving the dihydroxyamide 131.

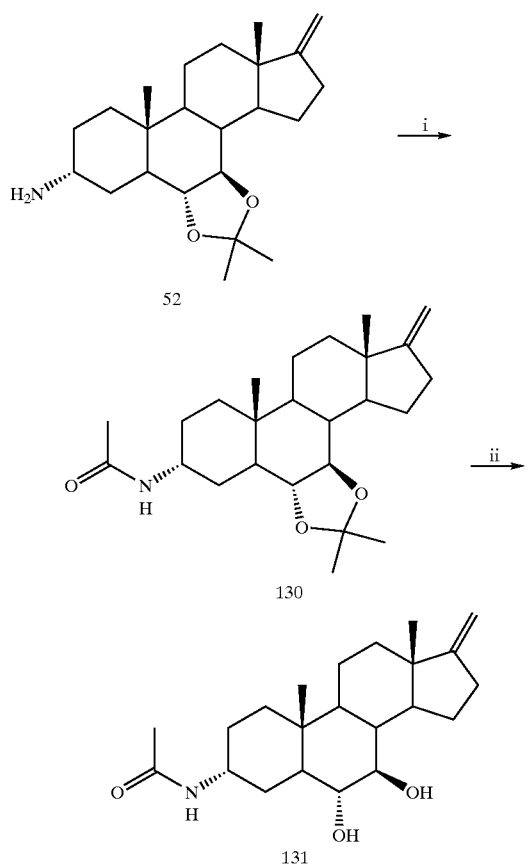

Scheme 13 i) acetyl chloride, PS-DIEA, CH$_2$Cl$_2$; PS-Trisamine; ii) 80% acetic acid.

Synthesis of Compound 130

A solution of the amine 52 (100 mg, 0.28 mmol), acetyl chloride (50 μl, 0.70 mmol), 440 mg of PS-DIEA resin and 2.4 ml of CH$_2$Cl$_2$ was stirred at room temperature for 16 hours. The resin was filtered and the filtrate was incubated for 2 hours with 260 mg of PS-Trisamine resin. The resin was filtered and the filtrate was concentrated. Purification using radial chromatography afforded 69 mg (62%) of compound 130.

Synthesis of Compound 131

A solution of the amide 130 (69 mg, 0.17 mmol) and 1 ml of 80% acetic acid was heated at 40° C. for 1 hour. The reaction mixture was twice taken up and concentrated from 5 ml of toluene, once from 5 ml of MeOH and once from 1 ml of acetone and 5 ml of hexanes to give 62 mg (62%) of compound 131 as a white solid. LC/MS (direct infusion, electrospray +ve, 10 mM NH$_4$OAc in 4:1 water and MeCN) 384.16; C$_{22}$H$_{35}$NNaO$_3$, 362.20; C$_{22}$H$_{36}$NO$_3$, 344.18; C$_{22}$H$_{34}$NO$_2$.

Synthesis of Compound 132

Using the procedure described for the synthesis of compound 130, the amine 52 (88 mg, 0.24 mmol) was reacted with benzoyl chloride (65 μl, 0.56 mmol) to give 64 mg of amide intermediate. A solution of the amide intermediate and 2 ml of 80% acetic acid was heated at 40° C. for 1 hour. The reaction mixture was twice taken up and concentrated from 5 ml of toluene, once from 5 ml of MeOH and once from 1 ml of acetone and 5 ml of hexanes to give 55 mg (55%) of compound 132 as a white solid (see Table 3). LC/MS (direct infusion, electrospray +ve, 10 mM NH$_4$OAc in 4:1 water and MeCN) 446.18; C$_{27}$H$_{37}$NNaO$_3$, 424.29; C$_{27}$H$_{38}$NO$_3$, 406.19; C$_{27}$H$_{36}$NO$_2$.

Synthesis of Compound 133

Using the procedure described for the synthesis of compound 130, the amine 52 (100 mg, 0.28 mmol) was reacted with isopropylsulfonyl chloride (63 μl, 0.56 mmol) to give 38 mg of sulfonamide intermediate. A solution of the sulfonamide intermediate and 1.5 ml of 80% acetic acid was heated at 40° C. for 1 hour. The reaction mixture was twice taken up and concentrated from 5 ml of toluene, once from 5 ml of MeOH and once from 1 ml of acetone and 5 ml of hexanes to give 35 mg (29%) of compound 133 as an off-white solid (see Table 3). LC/MS (direct infusion, electrospray +ve, 10 mM NH$_4$OAc in 4:1 water and MeCN) 426.14; C$_{23}$H$_{40}$NO$_4$S.

Synthesis of Compound 134

Using the procedure described for the synthesis of compound 130, the amine 52 (100 mg, 0.28 mmol) was reacted with benzenesulfonyl chloride (90 μl, 0.70 mmol) to give 105 mg of sulfonamide intermediate. A solution of the sulfonamide intermediate and 2 ml of 80% acetic acid was heated at 40° C. for 5 hours. The reaction mixture was twice taken up and concentrated from 5 ml of toluene, once from 5 ml of MeOH and once from 1 ml of acetone and 5 ml of hexanes to give 83 mg (65%) of compound 134 as a white solid (see Table 3). LC/MS (direct infusion, electrospray +ve, 10 mM NH$_4$OAc in 4:1 water and MeCN) 482.11; C$_{26}$H$_{37}$NNaO$_4$S, 477.17; C$_{26}$H$_{41}$N$_2$O$_4$S, 460.15; C$_{26}$H$_{38}$NO$_4$S.

Example 15

3-Acylamiobiotin-6,7-hydroxy-17-ethylidene Steroid

Scheme 14 shows the synthesis of the amide 135. Reaction of the amine 83 with triethylamine and a water soluble version of biotin ester N-hydroxysuccinimide in methanol and water gave the biotinylated amide analogue 135.

Scheme 14

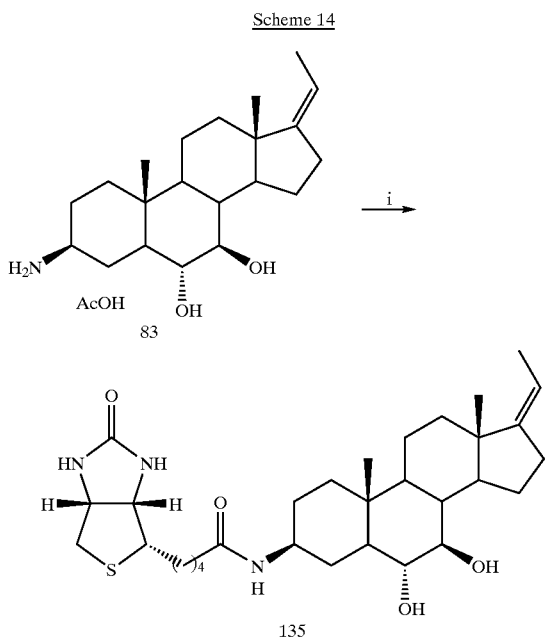

83

135 i) Sulfo-NHS-biotin, Et₃N, MeOH, water.

Synthesis of Compound 135

A solution of compound 83 (97 mg, 0.25 mmol), Et₃N (104 µl, 0.75 mmol), sulfo-NHS-biotin (120 mg, 0.27 mmol), 2.5 ml of MeOH and 2.5 ml of water was stirred at room temperature overnight. The reaction mixture was concentrated and purified using reverse phase column chromatography eluting with 5% water/MeOH to afford 89 mg (64%) of compound 135 as an off-white solid. LC/MS (direct infusion, electrospray +ve, 10 mM NH₄OAc in 4:1 water and MeCN) 560.30; $C_{31}H_{50}N_3O_4S$.

Example 16

3-Urea-6,7-hydroxy-17-methylidene Steroid

Any of the amines related to compound 52 can be reacted with isocyanates or isothiocyanates to give compounds having urea or thiourea functionalities. Compounds 136, 137 and 138 are examples of ureas that were synthesized using the methods shown in Scheme 15 (see Table 3).

Scheme 15

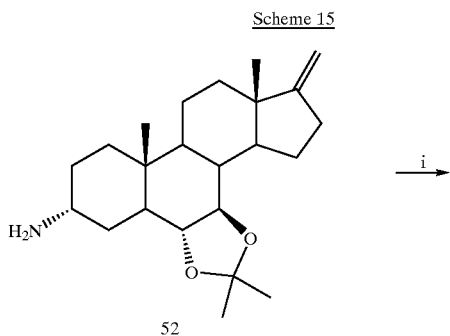

52

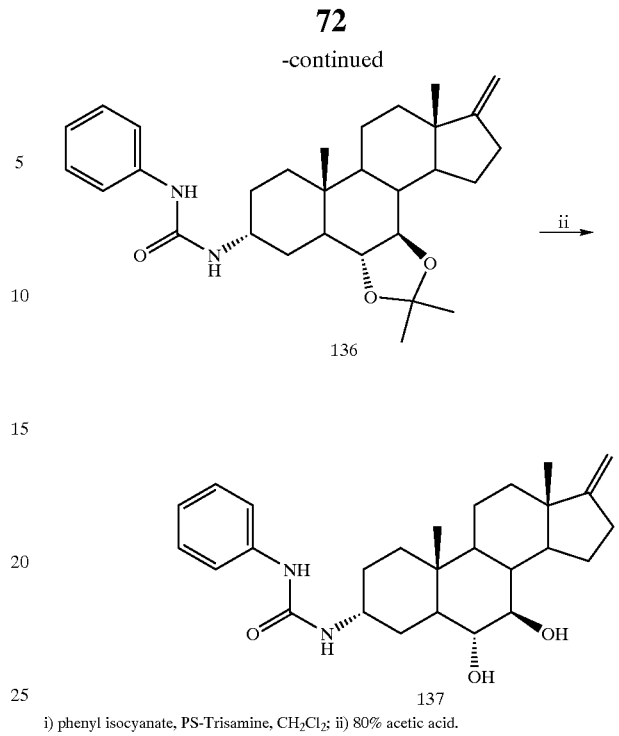

136

137 i) phenyl isocyanate, PS-Trisamine, CH₂Cl₂; ii) 80% acetic acid.

Synthesis of Compound 136

A solution of the amine 52 (100 mg, 0.28 mmol), phenyl isocyanate (76 µl, 0.70 mmol) and 2.4 ml of CH₂Cl₂ was stirred at room temperature for 16 hours. The solution was incubated for 2 hours with 260 mg of PS-Trisamine resin. The resin was filtered and the filtrate was concentrated. Purification using radial chromatography gave 95 mg (71%) of compound 136.

Synthesis of Compound 137

A solution of the urea 136 (95 mg, 0.20 mmol) and 2 ml of 80% acetic acid was heated at 80° C. for 2 hours. The reaction mixture was taken up and concentrated from 5 ml of toluene, from 5 ml of MeOH and from 5 ml of hexanes. Purification using radial chromatography eluting with 95:5:2 CH₂Cl₂:MeOH:Et₃N afforded 40 mg (33%) of compound 137. LC/MS (direct infusion, electrospray +ve, 10 mM NH₄OAc in 4:1 water and MeCN) 461.18; $C_{27}H_{38}N_2NaO_3$, 439.22; $C_{27}H_{39}N_2O_3$, 421.25; $C_{27}H_{37}O_2$.

Synthesis of Compound 138

Using the procedure described for the synthesis of compound 137, the amine 52 (100 mg, 0.28 mmol) was reacted with propyl isocyanate (52 µl, 0.56 mmol) to give 72 mg of urea intermediate. A solution of the urea intermediate and 2 ml of 80% acetic acid was heated at 80° C. for 2 hours. The reaction mixture was twice taken up and concentrated from 5 ml of toluene, once from 5 ml of MeOH and once from 5 ml of hexanes to afford 51 mg (45%) of compound 138 as a white solid. LC/MS (direct infusion, electrospray +ve, 10 mM NH₄OAc in 4:1 water and MeCN) 427.21; $C_{24}H_{40}N_2NaO_3$, 405.25; $C_{24}H_{41}N_2O_3$.

Example 17

3-Amino-6,7-hydroxy-17-dimethyl Unsaturated Steroid

Any compounds related to compounds 88 or 89 can undergo rearrangement using the method shown in Scheme 16. Treatment of compound 88 with a 50° C. solution of hydrochloric acid in methanol and water removed the acetonide protecting group, facilitated migration of the 18-methyl group to C17, and formed the ammonium chloride salt 139. Treatment of compound 89 with the same conditions also gave compound 139. Example compounds 140–148 were synthesized using the method shown in Scheme 16 (see Table 4).

Scheme 16

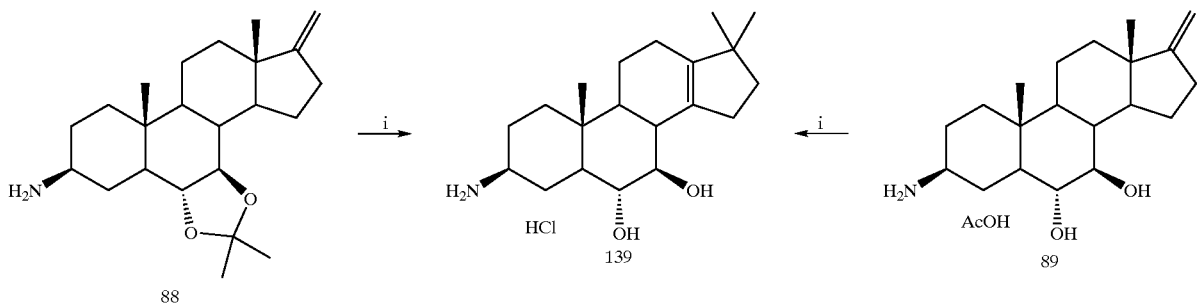

i) HCl, water, methanol, 50° C..

Synthesis of Compound 139

A solution of compound 88 (300 mg, 0.834 mmol), 4 drops of concentrated HCl, 2 ml of methanol and 2 ml of water was heated at 50° C. for 72 hours. The reaction mixture was concentrated and the residue was twice taken up in 5 ml of methanol and concentrated. The residue was taken up in 2 ml of methanol, diluted with 15 ml of acetone and concentrated. The residue was triturated in 5 ml of acetone, filtered and dried to give 286 mg (96%) of compound 139 as a white solid. LC/MS (direct infusion, electrospray +ve, 10 mM NH$_4$OAc in 4:1 water and MeCN) 320.20; C$_{20}$H$_{34}$NO$_2$.

Synthesis of Compound 139

Using the same procedure as described for the synthesis of compound 139 from compound 88, compound 89 was reacted to give 145 mg (77%) of compound 139 as a white solid. LC/MS (direct infusion, electrospray +ve, 10 mM NH$_4$OAc in 4:1 water and MeCN) 320.20; C$_{20}$H$_{34}$NO$_2$.

Synthesis of Compound 140

Using the procedure described for the synthesis of compound 99, the amine 88 (200 mg, 0.55 mmol) was reacted with m-tolualdehyde (90 μl, 0.61 mmol). Purification using radial chromatography eluting with 5% MeOH/EtOAc gave 127 mg of amine intermediate. A solution of the intermediate amine, 4 drops of concentrated HCl, 1 ml of MeOH and 1 ml of water was heated at 50° C. for 20 hours. The reaction mixture was taken up and concentrated thrice from 5 ml of MeOH and once from 5 ml of acetone to give 74 mg (30%) of compound 140 as an off-white foam. LC/MS (direct infusion, electrospray +ve, 10 mM NH$_4$OAc in 4:1 water and MeCN) 424.24; C$_{28}$H$_{42}$NO$_2$.

Synthesis of Compound 141

Using the procedure described for the synthesis of compound 99, the amine 88 (200 mg, 0.55 mmol) was reacted with 3,4-difluorobenzaldehyde (67 μl, 0.61 mmol). Purification using radial chromatography eluting with 30% EtOAc/hexanes gave 88 mg of amine intermediate. A solution of the intermediate amine, 4 drops of concentrated HCl, 1 ml of MeOH and 1 ml of water was heated at 50° C. for 20 hours. The reaction mixture was taken up and concentrated thrice from 5 ml of MeOH and once from 5 ml of acetone to give 73 mg (28%) of compound 141 as an off-white foam. LC/MS (direct infusion, electrospray +ve, 10 mM NH$_4$OAc in 4:1 water and MeCN) 446.42; C$_{27}$H$_{38}$F$_2$NO$_2$.

Synthesis of Compound 142

Using the procedure described for the synthesis of compound 59, the amine 49 (200 mg, 0.55 mmol) was reacted with 3,4-dimethoxybenzaldehyde (70 μl, 0.61 mmol). Purification using radial chromatography eluting with 40% EtOAc/hexanes gave 67 mg of amine intermediate. A solution of the intermediate amine, 4 drops of concentrated HCl, 1 ml of MeOH and 1 ml of water was heated at 50° C. for 20 hours. The reaction mixture was taken up and concentrated thrice from 5 ml of MeOH and once from 5 ml of acetone to give 43 mg (16%) of compound 142 as yellow solid. LC/MS (direct infusion, electrospray +ve, 10 mM NH$_4$OAc in 4:1 water and MeCN) 470.27; C$_{29}$H$_{44}$NO$_4$.

Synthesis of Compound 143

A solution of compound 28 (200 mg, 0.540 mmol), 4 drops of concentrated HCl, and 3 ml of water was heated at 50° C. for 72 hours. The reaction mixture was concentrated and the residue was twice taken up in 5 ml of methanol and concentrated. The residue was taken up in 3 ml of methanol, diluted with 20 ml of acetone and concentrated. The residue was triturated in 10 ml of acetone, filtered and dried to give 179 mg (90%) of compound 143 as a white solid. LC/MS (direct infusion, electrospray +ve, 10 mM NH$_4$OAc in 4:1 water and MeCN) 334.20; C$_{21}$H$_{36}$NO$_2$.

Synthesis of Compound 144

Titanium(IV) isopropoxide (270 μl, 0.92 mmol) was added to a room temperature solution of the ketone 108 (250 mg, 0.67 mmol), aniline (56 μl, 0.61 mmol) and 1.5 ml of THF under argon. After 12 hours a solution of NaBH$_4$ (65 mg, 1.7 mmol) in 2.3 ml of EtOH was added and the reaction was continued for another 8 hours. The reaction was quenched by the addition of 0.5 ml of water and filtered to remove a white precipitate. The solution was loaded onto a column of 600 mg of MP-TsOH resin and eluted with 9 ml of MeOH then 9 ml of 2 M NH$_3$ in MeOH. The NH$_3$/MeOH fraction was concentrated and the residue was taken up in 4 ml THF and treated with 500 mg of PS-benzaldehyde resin and filtered to remove any residual aniline. The solution was concentrated and the residue was taken up in 2 ml of 9:1

THF and water and 100 μl of concentrated HCl. After stirring at room temperature overnight the reaction mixture was concentrated. The residue was triturated in 1 ml of cyclohexane, filtered and dried to afford 62 mg of compound 144 as a white solid. LC/MS (direct infusion, electrospray +ve, 10 mM NH$_4$OAc in 4:1 water and MeCN) 410.03; C$_{27}$H$_{40}$NO$_2$.

Synthesis of Compound 145

Using the procedures described for the synthesis of compound 144, compound 108 (250 mg, 0.67 mmol) was reacted with 3-(trifluoromethyl)aniline. The intermediate product was purified using radial chromatography and then reacted with 100 μl of concentrated HCl in 2 ml of 9:1 THF and water. After stirring at room temperature overnight the reaction mixture was concentrated and the residue was triturated in 1 ml of cyclohexane, filtered and dried to afford 23 mg of compound 145 as a white solid. LC/MS (direct infusion, electrospray +ve, 10 mM NH$_4$OAc in 4:1 water and MeCN) 477.94; C$_{28}$H$_{39}$F$_3$NO$_2$.

Synthesis of Compound 146

Titanium(IV) isopropoxide (216 μl, 0.73 mmol) was added to a room temperature solution of the ketone 108 (200 mg, 0.54 mmol), benzylamine (53 μl, 0.49 mmol) and 1.2 ml of THF under argon. After 12 hours a solution of NaBH$_4$ (52 mg, 1.4 mmol) in 1.7 ml of EtOH was added and the reaction was continued for another 6 hours. The reaction was quenched by the addition of 1 ml of water and filtered to remove a white precipitate. The solution was diluted with 70 ml of CH$_2$Cl$_2$, washed with 10 ml of water and 20 ml of brine, dried over MgSO$_4$, filtered and concentrated. Purification using radial chromatography eluting consecutively with 20% EtOAc/hexanes, EtOAc and 95:5:2 CH$_2$Cl$_2$/MeOH/Et$_3$N afforded 127 mg of 3α-amine intermediate and 26 mg of 3β-amine intermediate. A solution of the 127 mg of 3α-amine intermediate, 1 ml of 9:1 THF and water and 0.1 ml of concentrated HCl was stirred at room temperature overnight. The reaction mixture was concentrated, the residue was taken up in 5 ml of MeOH and concentrated. The residue was triturated in 1 ml of cyclohexane, filtered and dried to afford 118 mg (95%) of compound 146 as a white solid. LC/MS (direct infusion, electrospray +ve, 10 mM NH$_4$OAc in 4:1 water and MeCN) 424.20; C$_{28}$H$_{42}$NO$_2$.

Synthesis of Compound 147

A solution of the 26 mg of 3β-amine intermediate, the synthesis of which was described under the synthesis of compound 146, 1 ml of 9:1 THF and water and 0.1 ml of concentrated HCl was stirred at room temperature overnight. The reaction mixture was concentrated, the residue taken up in 5 ml of MeOH and concentrated. The residue was triturated in 1 ml of cyclohexane, filtered and dried to afford 26 mg (100%) of compound 147 as a white solid. LC/MS (direct infusion, electrospray +ve, 10 mM NH$_4$OAc in 4:1 water and MeCN) 424.21; C$_{28}$H$_{42}$NO$_2$.

Synthesis of Compound 148

A solution of compound 78 (63 mg, 0.18 mmol), 4 drops of concentrated HCl, 1 ml of methanol and 1 ml of water was heated at 50° C. for 48 hours. The reaction mixture was concentrated and the residue was twice taken up in 5 ml of methanol and concentrated. The residue was taken up in 2 ml of hexanes, concentrated and dried for 2 hours using an Abderhalden drying apparatus with refluxing acetone to give 69 mg (100%) of compound 148 as a white solid. LC/MS (direct infusion, electrospray +ve, 10 mM NH$_4$OAc in 4:1 water and MeCN) 348.20; C$_{22}$H$_{38}$NO$_2$.

TABLE 1

| Compound | 3α- or 3β-NH$_2$ | R$_1$ | R$_2$ | R$_3$ | HA | Hex IC$_{50}$ (μM) | Calcium (% inhibition at 20 μM) |
|---|---|---|---|---|---|---|---|
| 49 | α | CH$_3$ | H | H | HCl | 11.0 | 26.8 |
| 53 | α | H | H | H | AcOH | 17.6 | −0.8 |
| 54 | α | H | H | H | HCl | 16.1 | 19.8 |
| 64 | α | CH$_3$ | F | H | HCl | 14.4 | 6.7 |
| 69 | α | H | CO$_2$CH$_3$ | H | AcOH | 21.2 | 11.2 |
| 28 | β | CH$_3$ | H | H | HCl | 6.8 | 29.0 |
| 83 | β | CH$_3$ | H | H | AcOH | 7.7 | 30.3 |
| 89 | β | H | H | H | AcOH | 11.5 | 15.0 |
| 95 | β | CH$_3$ | F | H | HCl | 13.5 | 11.2 |
| 78 | α | H | H | CH$_3$ | none | 20.1 | 5.3 |
| 79 | α | H | H | CH$_3$ | HCl | 18.4 | 9.1 |
| 80 | α | H | H | CH$_3$ | AcOH | 10.7 | 7.4 |

TABLE 2

| Compound | 3α- or 3β-NH$_2$ | R$_1$ | R$_2$ | HA | Hex IC$_{50}$ (μM) | Calcium (% inhibition at 20 μM) |
|---|---|---|---|---|---|---|
| 70 | α | O | O | AcOH | ND | 7.0 |
| 72 | α | OH | H | AcOH | ND | 10.3 |
| 96 | β | CH$_3$CH$_2$ | H | HCl | 7.8 | 47.9 |
| 97 | α | CH$_3$CH$_2$ | H | HCl | 9.3 | 43.0 |

TABLE 3

[Structure: steroid with R3-NH at C3, OH groups, and =CR1R2 at C17]

| Compound | 3α- or 3β-NH$_2$ | R$_1$ | R$_2$ | R$_3$ | Hex IC$_{50}$ (μM) | Calcium (% inhibition at 20 μM) |
|---|---|---|---|---|---|---|
| 131 | α | H | H | CH$_3$CO | 14.1 | 9.9 |
| 132 | α | H | H | C$_6$H$_5$CO | 10.0 | 19.6 |
| 133 | α | H | H | (CH$_3$)$_2$CHSO$_2$ | 15.9 | 13.8 |
| 134 | α | H | H | C$_6$H$_5$SO$_2$ | 16.7 | 25.1 |
| 135 | β | CH$_3$ | H | [biotin-aldehyde structure] | 15.1 | 37.3 |
| 137 | α | H | H | C$_6$H$_5$NHCO | 14.8 | 13.0 |
| 138 | α | H | H | CH$_3$(CH$_2$)$_2$NHCO | 15.0 | 9.0 |

TABLE 4

[Structure: steroid·HCl with R4-NH at C3, OR3 groups, and R1,R2 at C17]

| Compound | 3α- or 3β-NH$_2$ | R$_1$ | R$_2$ | R$_3$ | R$_4$ | Hex IC$_{50}$ (μM) | Calcium (% inhibition at 20 μM) |
|---|---|---|---|---|---|---|---|
| 139 | β | CH$_3$ | CH$_3$ | H | H | 10.3 | 26.3 |
| 140 | α | CH$_3$ | CH$_3$ | H | 3-(CH$_3$)C$_6$H$_4$CH$_2$ | 10.2 | 21.5 |
| 141 | α | CH$_3$ | CH$_3$ | H | 3,4-(F)$_2$C$_6$H$_3$CH$_2$ | 9.4 | 36.3 |
| 142 | α | CH$_3$ | CH$_3$ | H | 3,4-(CH$_3$O)$_2$C$_6$H$_3$CH$_2$ | 15.9 | 13.8 |
| 143 | β | CH$_3$ | CH$_3$CH$_2$ | H | H | 8.6 | 22.6 |
| 144 | α and β | CH$_3$ | CH$_3$CH$_2$ | H | C$_6$H$_5$ | 6.9 | 13.0 |
| 145 | α and β | CH$_3$ | CH$_3$CH$_2$ | H | 3-(CF$_3$)C$_6$H$_4$ | 22.0 | −0.2 |
| 146 | α | CH$_3$ | CH$_3$CH$_2$ | H | C$_6$H$_5$CH$_2$ | 9.0 | 41.7 |
| 147 | β | CH$_3$ | CH$_3$CH$_2$ | H | C$_6$H$_5$CH$_2$ | 18.1 | 36.3 |
| 148 | α | CH$_3$ | CH$_3$ | CH$_3$ | H | 29.2 | 6.6 |

TABLE 5

| Compound | R | HA | Hex IC$_{50}$ ($\mu$M) | Calcium (% inhibition at 20 $\mu$M) |
|---|---|---|---|---|
| 110 | piperidinyl | AcOH | 10.9 | 39.7 |
| 111 | morpholinyl | HCl | 9.3 | 53.1 |
| 113 | CH$_3$NH | HCl | 9.8 | 45.0 |
| 114 | CH$_3$(CH$_2$)$_2$NH | HCl | 10.2 | 37.9 |
| 115 | CH$_3$(CH$_2$)$_4$NH | HCl | 11.1 | 40.0 |
| 116 | C$_5$H$_9$NH | AcOH | 9.6 | 60.9 |
| 117 | C$_6$H$_{11}$NH | AcOH | 6.6 | 42.2 |
| 118 | pyrrolidinyl | AcOH | 11.0 | 41.8 |
| 119 | CH$_3$(CH$_2$)$_2$NH(CH$_2$)$_2$NH | 2HCl | 6.1 | 54.5 |
| 120 | (CH$_3$)$_2$N(CH$_2$)$_2$NH | 2HCl | 9.1 | 44.0 |
| 121 | piperazinyl | AcOH | 14.4 | 42.4 |
| 122 | HOCH$_2$CH$_2$NH | HCl | 12.3 | 31.4 |
| 123 | HOCH$_2$(CH$_2$)$_4$NH | HCl | 16.7 | 12.8 |
| 124 | HOCH$_2$CH$_2$NHCH$_2$CH$_2$NH | 2HCl | ND | 21.0 |
| 125 | 3-(CH$_3$)C$_6$H$_4$NH$_2$ | HCl | 39.4 | 5.7 |
| 126 | 4-(HO)C$_6$H$_4$NH | HCl | 9.7 | 45.0 |
| 127 | 4-(H$_2$NSO$_2$)C$_6$H$_4$NH | HCl | 10.1 | 29.4 |
| 128 | (3-pyridylmethyl)NH | AcOH | 10.5 | 41.0 |
| 129 | histaminyl | 2AcOH | N/A | 13.8 |

TABLE 6

| Compound | R | HA | Hex IC$_{50}$ ($\mu$M) | Calcium (% inhibition at 20 $\mu$M) |
|---|---|---|---|---|
| 100 | 4-((CH$_3$)$_2$CH)C$_6$H$_4$ | AcOH | 18.2 | 33.2 |
| 101 | 2-(F)C$_6$H$_4$ | AcOH | 10.3 | 16.3 |
| 102 | 3-(CF$_3$)C$_6$H$_4$ | AcOH | 10.0 | 9.5 |
| 103 | 2-(CH$_3$O)C$_6$H$_4$ | AcOH | 11.1 | 23.7 |
| 104 | 4-(CF$_3$O)C$_6$H$_4$ | AcOH | 9.5 | 30.3 |
| 105 | 3-(C$_6$H$_5$O)C$_6$H$_4$ | AcOH | 22.5 | 10.2 |
| 106 | 3-(NO$_2$)C$_6$H$_4$ | none | 8.8 | 8.1 |
| 107 | 3-C$_5$H$_4$N | 2HCl | 17.2 | 11.6 |

Utility Examples

Example A

Effect of Selected Compounds on Allergen-Induced Lung Inflammation

The ability of a compound to inhibit the allergen-induced accumulation of inflammatory cells such as eosinophils and neutrophils in the lavage fluid obtained from sensitized animals is indicative of that compound's anti-asthma activity. In particular, this model system is useful in the evaluation of the effects of a test compound in the treatment of the late phase response of asthma, when lung inflammation and the second phase of bronchoconstriction is apparent. The test is conducted as follows.

Male Brown Norway rats are sensitized to ovalbumin by single intraperitoneal injection of 1 mg ovalbumin adsorbed to 100 mg A(OH)$_3$ (alum) in 1 ml sterile saline (saline control rats receive only sterile saline) on day 1, and allowed to sensitize until day 21. Test compounds are given orally q.d. for three days prior to challenge (days 19, 20, 21), and one day post challenge (day 22), with the third dose given 2 hours before challenge, and the fourth day dose given 24 hours after challenge (volume=300 $\mu$l/dose). Rats are challenged with 0.5% ovalbumin in saline generated using a Devillbis nebulizer for 60 min on day 21.

Forty-eight hrs after challenge, animals are sacrificed with an overdose of intraperitoneally-delivered sodium pentobarbitol and the lungs are lavaged with cold 2×7 ml phosphate buffered saline. The recovered lavage fluid is placed on ice. The bronchoalveolar lavage fluid is centrifuged and the supernatant removed. The pellet is resuspended in phosphate buffered saline at 4° C. Cytospins are prepared and stained for differentiation and enumeration of cell types.

The protective effects of the various test compounds on allergen induced lung inflammation are summarized in Tables 7 and 8. The dose response activity of select compounds is shown in Table 9. Test compound was administered in 300 $\mu$l corn oil (Tables 7 and 8) or water (Table 9), which were used as vehicles. Control animals received 300 $\mu$l corn oil or water alone, i.e., no drug. Values in Tables 7, 8, and 9 represent percent inhibition of leukocyte accumulation relative to control animals. A negative value in Table 7, 8, or 9 indicates an exacerbation of the effect over the control animal.

TABLE 7

EFFECT OF TEST COMPOUNDS (5 MG/KG/DAY FOR 4 DAYS, P.O.) ON OVALBUMIN-INDUCED ACCUMULATION OF INFLAMMATORY CELLS IN THE LUNG LAVAGE FLUID OBTAINED FROM SENSITIZED BROWN NORWAY RATS

| Compound | % inhibition of eosinophils | % inhibition of neutrophils | % inhibition of lymphocytes |
| --- | --- | --- | --- |
| 83 | 67 | 34 | 38 |
| 97 | 40 | 52 | 56 |
| 96 | −9 | 40 | 19 |
| 64 | 62 | 70 | 81 |
| 89 | 57 | 60 | 64 |
| 28 | 85 | 87 | 124 |
| 53 | 24 | 57 | 13 |
| 95 | 14 | 45 | 30 |
| 49 | 52 | 36 | 73 |
| 135 | 20 | 58 | 107 |

TABLE 8

EFFECT OF SELECTED COMPOUNDS (1 MG/KG/DAY FOR 4 DAYS, P.O.) ON OVALBUMIN-INDUCED ACCUMULATION OF INFLAMMATORY CELLS IN THE LUNG LAVAGE FLUID OBTAINED FROM SENSITIZED BROWN NORWAY RATS

| Analogue | % inhibition of eosinophils | % inhibition of neutrophils | % inhibition of lymphocytes |
| --- | --- | --- | --- |
| 142 | −131 | −1 | −42 |
| 54 | −82 | −19 | −7 |
| 107 | −122 | 23 | −28 |
| 124 | −55 | −76 | −26 |
| 129 | −296 | −114 | −71 |
| 146 | 8 | 24 | −27 |
| 147 | 40 | 58 | 36 |
| 131 | 16 | 57 | 21 |
| 138 | −52 | 35 | 33 |
| 133 | −43 | 40 | 28 |

TABLE 9

DOSE DEPENDENT EFFECT OF SELECTED COMPOUNDS (MULTIPLE DOSING, 4 DAYS QD, P.O.) ON OVALBUMIN-INDUCED ACCUMULATION OF INFLAMMATORY CELLS IN THE LUNG LAVAGE FLUID OBTAINED FROM SENSITIZED BROWN NORWAY RATS

| Analogue | % inhibition of eosinophils | | | | % inhibition of neutrophils | | | | % inhibition of lymphocytes | | | |
| --- | --- | --- | --- | --- | --- | --- | --- | --- | --- | --- | --- | --- |
| mg/kg | 1 | 0.3 | 0.1 | 0.03 | 1 | 0.3 | 0.1 | 0.03 | 1 | 0.3 | 0.1 | 0.03 |
| 89 | 71 | 80 | 35 | — | 66 | 72 | 25 | — | 6 | 70 | 2 | — |
| 28 | 60 | 71 | 29 | 5 | 41 | 66 | −10 | −26 | 70 | 85 | 50 | −5 |
| 139 | 42 | 41 | 46 | — | 63 | 62 | 42 | — | 56 | 34 | 19 | — |
| 143 | 48 | 29 | 28 | — | 64 | 25 | 57 | — | −22 | −37 | −43 | — |

Example B

Effect of Compound 83 on Irritant-Induced Mouse Ear Edema

A number of mice are uniquely identified by placing a mark with an indelible marker on their tail. Mice are dosed orally with 15 mg/kg test compound in 100 μl of 45% β-cyclodextrin in saline. Mice are briefly anaesthesized with 2% halothane, and 2 μg of phorbol 12-myristate 13-acetate in 25 μl of acetone is applied to the inner and outer sides of the left ear of the mouse. Acetone is applied to the right ear of the mouse in the same manner to serve as a vehicle control. Control animals receive the same treatment but without any test compound. After 3 hours, mice are sacrificed by cervical dislocation, and a standard sized biopsy is excised from the ears and weighed to the nearest 1/10th of a mg. Data are analyzed by taking the difference of each left ear from the right ear, and then calculating the % inhibition of edema by (((mean Rx/mean irritant))×100)-100.

The compounds of the present invention demonstrate protective effects on irritant induced mouse ear edema. For example, compound 83 inhibits irritant-induced mouse ear edema by 38% compared to control animals.

Example C

Effect of Compounds on the Release of Hexosaminidase from a Rat Mast Cell Line (RBL-2H3)

The anti-allergic effects of a compound of the present invention was evaluated by measuring its effect on antigen-induced secretion of hexosaminidase from a passively sensitized rat mast cell line. The ability of a test compound to inhibit the release of mast cell granule contents, e.g., histamine and hexosaminidase, is indicative of the anti-allergy and/or anti-asthma activity of the compound. Hexosaminidase is released from the mast cell granule along with histamine and other mediators during antigen challenge. The test is performed as follows.

RBL-2H3 cells are grown in culture and passively sensitized for 1 hour at 37° C. to dinitrophenol (DNP) using anti-human-DNP (IgE). Cells are incubated with test compound for 30 minutes at 37° C. and stimulated with 0.5 μg/ml DNP-HSA (antigen) for 30 minutes. Aliquots of the supernatant are removed and used to measure the amount of hexosaminidase released during challenge with the antigen. The amount of hexosaminidase present in the supernatant is determined colorimetrically by monitoring the enzymatic metabolism of p-nitrophenyl-N-acetyl-β-D-glucosaminide (p-NAG) over a period of 60 minutes at 405 nm. The effect of each test compound is determined as a percentage of the antigen-induced response (minus background release) obtained in the presence of DMSO alone. These values are used to determine the degrees of inhibition of antigen-induced hexosaminidase release from the cells.

The compounds of the present invention demonstrate the ability to inhibit hexosaminidase release in response to antigen stimulation. Compounds were tested at 0.3, 3, 10 and 30 μM, and the $IC_{50}$ calculated. This data is summarized in Tables 1–6. For example, compound 119 at 6.1 μM inhibits hexosaminidase release by 50% in response to antigen stimulus.

Example D

Metabolic Stability of Selected Compounds in Human S9 Fractions

The therapeutic effectiveness of a test compound can be often directly related to its metabolic stability in vivo. The majority of known, marketed drugs are metabolized by a group of enzymes known as P450 enzymes. The S9 fraction of human liver contains all the P450 enzymes and also cytoplasmic enzymes that may be involved in the metabolism of new chemical entities. Metabolism in vitro using human S9 fractions is a standard assay to evaluate relative metabolic stability of new compounds. The test is performed as follows.

Reagents are thawed on ice and combined to make up a Master Mix as follows: Potassium phosphate (100 mM, pH 7), G6P (0.25 mM), G6PDH (2 U/ml), NADPH (1 mM), UDP (0.25 mM), APPS (0.25 mM), and S9 fraction (2 mg/ml). A volume of 498 µl of the Master mix is dispensed into each microcentrifuge tube. A volume of 2 µl of 2.5 mM test compound (final concentration of 10 µM) is dispensed into the center of the lid of the appropriate tube, and the lids gently closed to prevent mixing. Synchronous combination of test compound and master mix is achieved by simultaneous ten times inversion of the tubes, which are then incubated at 37° C. and shaken at 150 rpm for the appropriate incubation times. While incubation is in progress, all 0 time samples are mixed individually by three times inversion followed by the immediate addition of 500 µl ice cold acetonitrile with three times inversion to stop the reaction. Immediately after each 15 minutes and 30 minutes incubation is complete, ice cold acetonitrile is added to each tube and the tubes mixed by three times inversion. All sample tubes are incubated at −80° C. for a minimum of 15 minutes, thawed and remixed by inversion. Aliquots of 650 µl are transferred to Chromatographic Specialties micro-spin filter system tubes (0.2 µm nylon membrane, C618505) and centrifuged at 13,000 rpm for 48 seconds. The sample filtrates are stored at −80° C.

Sample filtrates are analyzed on LCMS, and percent remaining after 15 and 30 minute incubation is calculated relative to the 0 minute incubation.

The metabolic stability of various compounds are summarized in Table 10 as the percent remaining after 15 or 30 minutes incubation with human liver S9 fractions.

TABLE 10

METABOLIC STABILITY OF SELECTED COMPOUNDS AFTER 15 AND 30 MINUTES INCUBATION WITH HUMAN LIVER S9 FRACTIONS SHOWN AS THE PERCENT REMAINING OF STARTING CONCENTRATION AFTER 0 MINUTES INCUBATION

| Compound | % remaining after 15 min | % remaining after 30 min |
|---|---|---|
| 83 | 92 ± 19 | 91 ± 21 |
| 97 | 94 ± 10 | 89 ± 12 |
| 96 | 92 ± 19 | 94 ± 21 |
| 89 | 100 ± 17 | 98 ± 16 |
| 28 | 100 ± 6 | 104 ± 12 |
| 49 | 93 ± 6 | 85 ± 8 |
| 64 | 104 ± 4 | 88 ± 5 |
| 139 | 109 ± 26 | 100 ± 10 |
| 143 | 100 ± 3 | 99 ± 10 |

TABLE 10-continued

METABOLIC STABILITY OF SELECTED COMPOUNDS AFTER 15 AND 30 MINUTES INCUBATION WITH HUMAN LIVER S9 FRACTIONS SHOWN AS THE PERCENT REMAINING OF STARTING CONCENTRATION AFTER 0 MINUTES INCUBATION

| Compound | % remaining after 15 min | % remaining after 30 min |
|---|---|---|
| 146 | 82 ± 6 | 63 ± 9 |
| 107 | 84 ± 5 | 62 ± 6 |
| 142 | 80 ± 11 | 55 ± 2 |
| 69 | 73 ± 24 | 63 ± 6 |
| 104 | 53 ± 10 | 56 ± 18 |
| 141 | 100 ± 9 | 26 ± 4 |
| 134 | 85 ± 54 | 36 ± 15 |
| 137 | 93 ± 31 | 71 ± 17 |
| 138 | 71 ± 4 | 65 ± 65 |
| 132 | 60 ± 17 | 40 ± 9 |
| 79 | 67 ± 6 | 61 ± 14 |

Example E

Solubility of Selected Compounds in Physiologically Compatible Formulations

Compounds of the present invention exhibit good water solubility. For example, compound 83 is soluble in water at 225 mg/ml. Compound 83 substituted with a hydroxy at C3 has a solubility in water of less than 60 µg/ml. Compounds 28 and 89 have solubilities at room temperature of ~30 mg/ml, which can be significantly increased by heating. This unexpected finding indicates that these 3-amino compounds should be readily formulated into therapeutic compositions.

Example F

Effect of Selected Test Compounds on Antigen-Induced Calcium Flux

Elevation of cytoplasmic calcium concentration is a common and crucial event which follows the activation of many types of cell surface receptors. Increases in intracellular calcium that occur following agonist activation of inositol lipid hydrolysis are the results of calcium release from the endoplasmic reticulum and the influx of calcium through the plasma membrane. Increases in cytosolic calcium concentration are involved in many important cellular responses in the inflammatory process including adhesion, motility, gene expression, proliferation, and degranulation. Changes in intracellular calcium centrations can affect both short and long term cellular responses. An assay method to evaluate a test compound's impact on calcium flux is provided as follows.

Jurkat clone E6.1 cells grown in RPMI medium supplemented with 10% FBS and 2 mM L-Glutamine are transferred to 50 mL conical tubes and centrifuged for 5 minutes at 900 RPM to form a cell pellet. The resulting supernatants are discarded and each pellet is washed in 10 mL HBSS. Cell suspensions are accumulated and centrifuged for 5 minutes at 900 RPM to form a cell pellet. The resulting supernatant is discarded and the pellet is resuspended in HBSS at $1 \times 10^7$ cells/mL. The cell suspension is transferred to a 20 mm petri dish and incubated at 37° C., 5% $CO_2$ for 20 minutes.

One volume of Fura 2AM is mixed to one volume of detergent Pluronic F127. Cells are labeled with 4 µL of probe solution to each mL of cell suspension. The petri dish is wrapped in aluminum foil to protect from light and placed on a plate shaker for 30 minutes at room temperature.

The following steps are done in the laminar flow hood with the fluorescent lights turned off. The petri dish is removed from the shaker and the labeled cell suspension is transferred to a 15 mL conical tube and washed twice with HBSS as above. The cell pellet is resuspended in 12 mL HBSS and left wrapped in foil for 30 minutes at room temperature. The labeled cell suspension is aliquoted (100 µL/well) into a Dynex 96 well white opaque tissue culture plate. 50 µL of each test sample is added to appropriate wells and are incubated together for 10 minutes at 37° C. in the Wallac 1920 Victor™ plate reader (test samples are prepared in HBSS at 20 mM, final concentration is 20 µM). Selected compounds were tested for dose related activity. Test samples and activator (anti—CD3 mAb at final concentration of 4 µg/mL, PharMingen) are added manually (50 µL), such that the minimum time to acquire the first data point after stimulation is approximately 30 seconds. The calcium influx response to anti-CD3 mAb is measured as an "end point" assay. The entire plate is read in 100 seconds using a kinetic of 1 second per well.

The plate is read before the addition of anti-CD3 to monitor non-specific effect of samples/drugs. Fluorescence emission is measured at 510 nm with excitation alternating between 340 and 380 every second using an excitation/emission filter pair. Data from these dual wavelengths are represented as a ratio of 2 excitations wavelengths. This ratio is independent of intracellular dye and cell concentrations, enabling real comparison between experiments.

The effect of selected compounds on calcium flux in antigen challenged Jurkat clone E6.1 cells is summarized in Tables 1–6. For example, compound 116 inhibited calcium by 60.9% at 20 µM. The $IC_{50}$ for compound 119 is less than or equal to 10 µM when dose response activity was examined. This demonstrated substantial effect on calcium flux would be beneficial in any disease pathology for which calcium is a significant second messenger or effector molecule, including but not limited to ischemia/reperfusion injury such as stroke or myocardial infarction, inflammatory diseases such as asthma or allergy, neural or muscular disorders such as Parkinson's disease or epilepsy, cardiac arrhythmias, or hypertension.

Example G

Effect of Selected Compounds on Allergen-Induced Changes in Lung Function

In asthma, the early response of the airways to allergen challenge is characterized by an immediate bronchoconstriction which peaks 20–30 min after exposure to the stimuli, and which normally resolves after approximately 2 hours. Anti-inflammatories are not generally active bronchodilators and are not very effective in the control of acute asthmatic bronchoconstriction. This results in the need for combination therapy to treat both the bronchoconstriction and the inflammation.

Cam-Hartley guinea pigs were sensitized to ovalbumin (OA) in groups of 5–6 by exposure to an aerosolized solution of 1% OA in saline for 15 min on 2 consecutive days via a DeVilbiss nebulizer, with an additional single intradermal injection of 3 µg OA in saline on Day 1. Animals were found to be at peak sensitivity to the antigen approximately 14 days after the initial exposure. On Day 14, the animals were initially anaesthetized with ketamine (50 mg/kg i.p.) and xylazine (10 mg/kg i.p.), weighed, and then maintained on 1% halothane delivered via a nose cone. The left carotid artery was cannulated with PE90 tubing containing 200 U/ml heparin in saline. A tracheostomy was performed and a fluid-filled cannula (PE 160) was inserted approximately 7 cm into the esophagus. The animal was positioned in a plethysmograph and the trachea attached to a fixed stainless steel tracheal tube in the body box. The carotid cannula was attached to a pressure transducer for monitoring of blood pressure and heart rate. The guinea pig was paralyzed with pancuronium bromide (0.8 mg/kg) and ventilated with air at a frequency of 60 Hz and tidal volume of 3 ml using a Harvard small animal ventilator.

Data was collected for 20 sec periods at a sampling rate of 100 Hz on a computer-linked physiological recording system using DIREC physiological software and analyzed using ANADAT software. Pulmonary resistance and dynamic lung compliance values were obtained from the volume, flow and pressure signals according to the method of Von Neeguard & Wirz (1927), using an isovolumetric multi-point regression model for analysis (Ludwig, Robatto, et al. 1991), and calculated as absolute changes in lung resistance ($R_L$; cm $H_2O$/ml/s) or lung compliance ($C_{DYN}$; ml/cm$H_2O$). Volume and pressure signals were calibrated before each set of experiments following standard procedures.

Several lung function measurements were obtained over a 5–10 minute period to ensure a steady baseline, and then the animal was challenged with OA (2% in saline) administered in 6 tidal breaths as a nebulized aerosol at a flow rate of 5 L/min. Pulmonary and cardiovascular function was continually monitored throughout the experiment, although data was collected at specific time-points after antigen challenge (10 s, 1, 2, 3, 4, 5, 10, 20, and 30 min).

Test compounds were administered under light halothane anesthesia by oral gavage (0.1–1.0 mg/kg/day q.d.) in 300 µl polyethylene glycol-200 for 4 days prior to challenge with the final dose administered 2 hours prior to antigen challenge.

Figure 4:
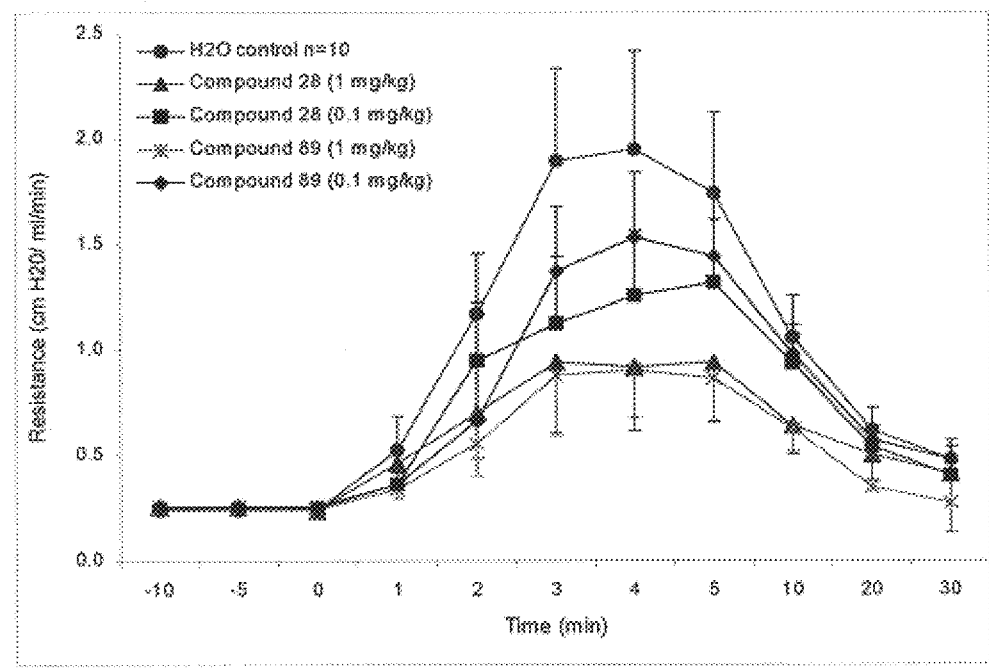
FIG. 4 is a graph showing the effect of test compounds 28 and 89, administered orally once per day for 4 days prior to challenge, on allergen-induced changes in lung resistance in sensitized guinea pigs.
Figure 5:
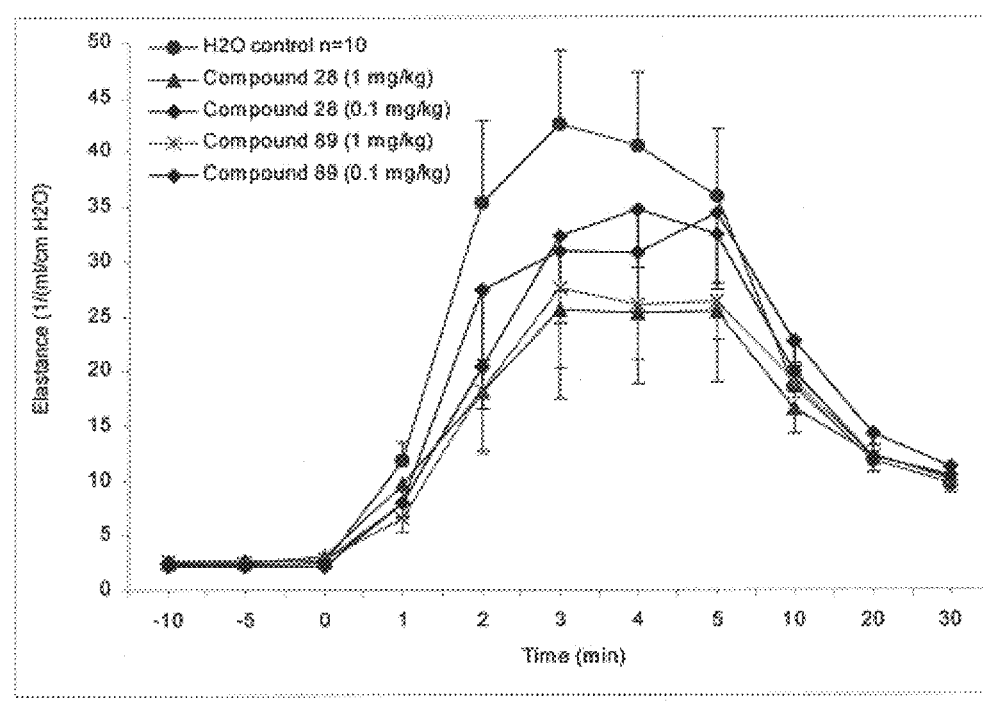
FIG. 5 is a graph showing the effect of test compounds 28 and 89, administered orally once per day for 4 days prior to challenge, on allergen-induced changes in lung elastance in sensitized guinea pigs.
Figure 6:
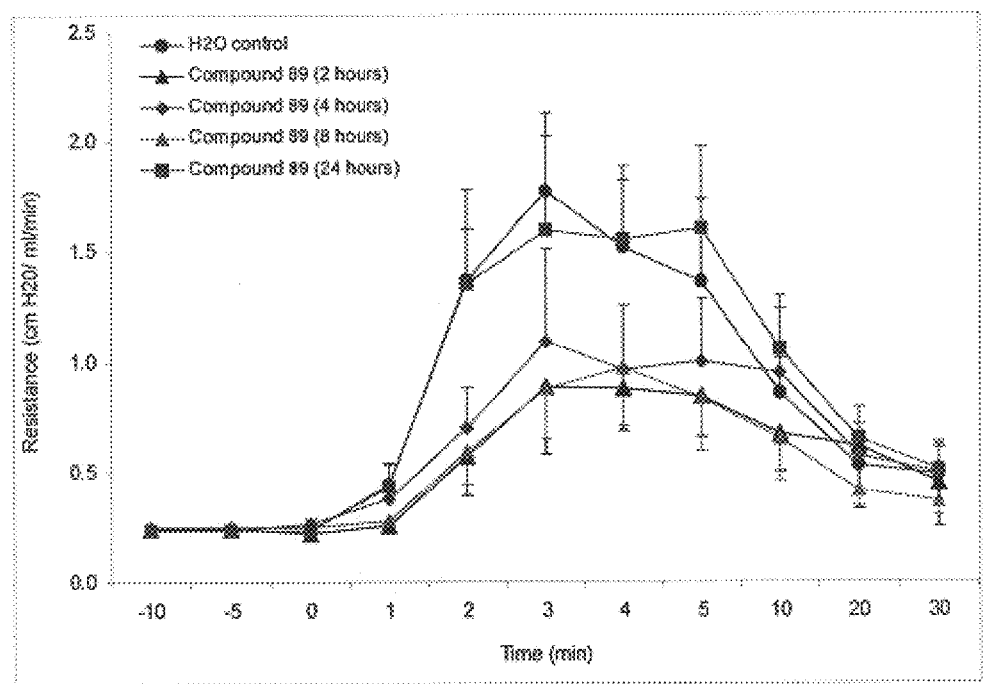
FIG. 6 is a graph showing duration of anti-bronchospastic activity of test compound 89, administered orally at 1 mg/kg once per day for 4 days prior to challenge, on allergen-induced changes in lung resistance in sensitized guinea pigs.
Figure 7:
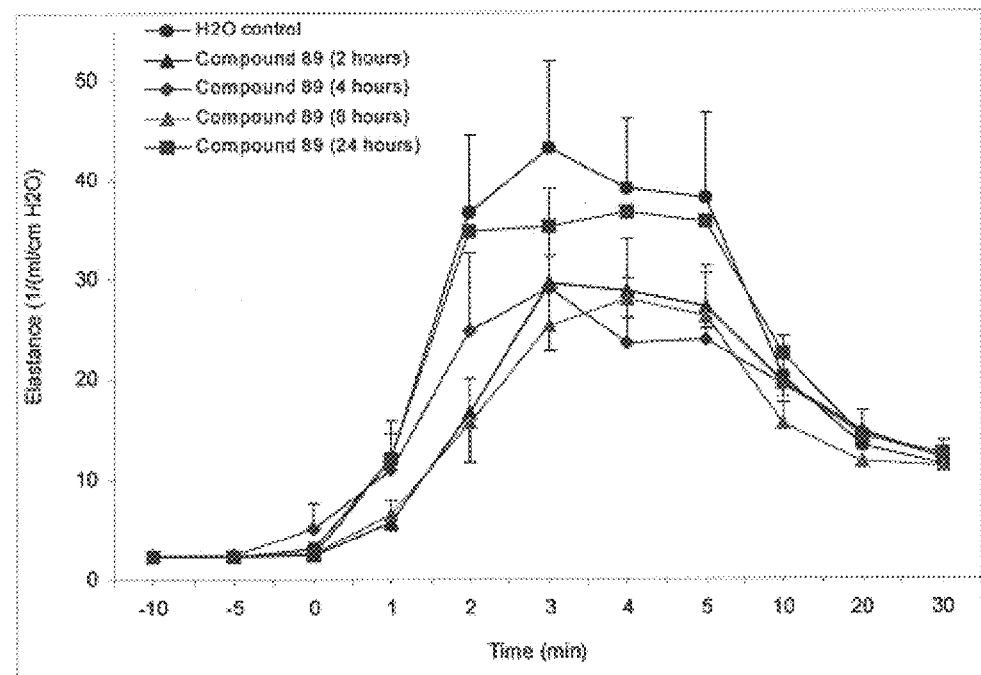
FIG. 7 is a graph showing duration of anti-bronchospastic activity of test compound 89, administered orally at 1 mg/kg once per day for 4 days prior to challenge, on allergen-induced changes in lung elastance in sensitized guinea pigs.

The protective effects of select test compounds on allergen induced bronchoconstriction are summarized in FIGS. 4 and 5. The duration of activity of Compound 89 is shown in FIGS. 6 and 7. Data is presented as mean±standard error of the mean. The inhibition of the bronchoconstriction by the test compounds would be beneficial in any disease where acute smooth muscle constriction in response to allergen challenge is manifest, such as asthma and allergy.

All publications and patent applications mentioned in this specification are herein incorporated by reference to the same extent as if each individual publication or patent application was specifically and individually incorporated by reference. For example, the book in Comprehensive Organic Transformations, A Guide to Functional Group Preparations, Second Edition, Richard C. Larock, John Wiley and Sons, Inc., 1999, and particularly the references cited therein, is incorporated herein by reference for all purposes.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of the formula or pharmaceutically acceptable salts, solvates and stereoisomers thereof, in isolation or in mixture, where independently at each occurrence:

$R^1$ and $R^2$ are hydrogen;

$R^3$ and $R^4$ are independently selected from direct bonds to the carbons at numerals 6 and 7 respectively so as to form carbonyl groups, hydrogen, or a protecting group such that $R^3$ and/or $R^4$ is part of hydroxyl or carbonyl protecting group; and in addition to the —$OR^3$ and —$OR^4$ groups as shown, each of carbons at numerals 6 and 7 is substituted with hydrogen unless precluded because —$OR^3$ or —$OR^4$ represent a carbonyl group;

numerals 1 through 16 each represent a carbon;

carbons at numerals 1, 2, 4, 11, 12, 15 and 16 are each substituted with two hydrogens unless said carbon is part of an unsaturated bond;

carbons at numerals 5, 8, 9 and 14 are each substituted with one hydrogen unless said carbon is part of an unsaturated bond;

carbon at numeral 10 is substituted with methyl;

carbon at numeral 13 is substituted with methyl unless it is part of an unsaturated bond;

and where the carbon at numeral 17 is substituted with
(a) one of =$C(R^5)(R^5)$ and =$C$=$C(R^5)(R^5)$, or
(b) two of the following, which are independently selected: hydrogen, $C_{1-6}$alkyl and $C_{1-6}$haloalkyl;

each of rings A, B, C and D is independently fully saturated, partially saturated or fully unsaturated;

$R^5$ at each occurrence is independently selected from H, X, and $C_{1-30}$ organic moiety that may optionally contain at least one heteroatom selected from the group consisting of boron, halogen, nitrogen, oxygen, silicon and sulfur; and X represents fluoride, chloride, bromide and iodide.

2. The compound of wherein claim 1, wherein $R^1$ and $R^2$ are hydrogen;

$R^3$ $R^4$ are independently selected from hydrogen and protecting groups such that $R^3$ and/or $R^4$ is part of hydroxyl protecting group;

carbons at numerals 1, 2, 4, 11, 12, 15 and 16 are each substituted with two hydrogens;

carbons at numerals 5, 8, 9 and 14 are each substituted with one hydrogen unless said carbon is part of an unsaturated bond;

carbon at numeral 10 is substituted with methyl;

carbon at numeral 13 is substituted with methyl unless it is part of an unsaturated bond;

and where the carbon at numeral 17 is substituted with
(a) one of =$C(R^5)(R^5)$ and =$C$=$C(R^5)(R^5)$, or
(b) two of the following, which are independently selected: hydrogen, $C_{1-6}$alkyl and $C_{1-6}$haloalkyl;

each of rings A, B, C and D is independently fully saturated or partially saturated;

at each occurrence is independently selected from H, X, and $C_{1-30}$ hydrocarbons, halocarbons and halohydrocarbons; and X represents fluoride, chloride, bromide and iodide.

3. A compound of the formula or pharmaceutically acceptable salts, solvates and stereoisomers thereof, in isolation or in mixture, where independently at each occurrence:

$R^1$ and $R^2$ are independently selected from
hydrogen,
oxygen so as to form nitro or oxime,
amino,
sulfur so as to form —$SO_3$—R or —$SO_2$—R wherein R is selected from H and organic groups having 1–30 carbons optionally containing 1–6 heteroatoms selected from nitrogen, oxygen, phosphorous, silicon and sulfur, and
organic groups having 1–30 carbons and optionally containing 1–6 heteroatoms selected from nitrogen, oxygen, phosphorous, silicon, and sulfur,
where $R^5$ may be a direct bond to numeral 3;

$R^3$ and $R^4$ are independently selected from direct bonds to the carbons at numerals 6 and 7 respectively so as to form carbonyl groups, hydrogen, or a protecting group such that $R^3$ and/or $R^4$ is part of hydroxyl or carbonyl protecting group;

numerals 1 through 16 each represent a carbon, where carbons at numerals 1, 2, 4, 11, 12, 15 and 16 may be independently substituted with
(a) one of: =O, =$C(R^5)(R^5)$ and =$C$=$C(R^5)(R^5)$; or
(b) two of the following, which are independently selected: —X, —$N(R^1)(R^2)$, —$R^5$ and —$OR^6$;

and where the carbon at numeral 17 is substituted with =$C(R^5)(R^5)$;

and where carbons at numerals 5, 8, 9, 10, 13 and 14 may be independently substituted with one of —X, —$R^5$, —$N(R^1)(R^2)$ or —$OR^6$;

in addition to the —$OR^3$ and —$OR^4$ groups as shown, each of the carbons at numerals 6 and 7 may be independently substituted with one of —X, —$N(R^1)(R^2)$, —$R^5$ or —$OR^6$;

each of rings A, B, C and D is independently fully saturated, partially saturated or fully unsaturated;

each $R^5$ is independently selected from hydrogen, halogen, $C_{1-6}$alkyl, $C_{1-6}$hydroxyalkyl, and —$CO_2$—$C_{1-6}$alkyl;

$R^6$ is H or a protecting group such that —$OR^6$ is a protected hydroxyl group; and X represents fluoride, chloride, bromide and iodide.

4. A compound of the formula

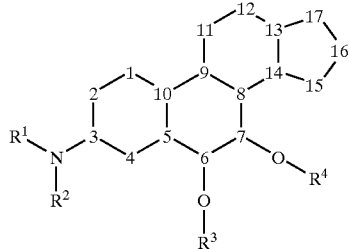

or pharmaceutically acceptable salts, solvates and stereoisomers thereof, in isolation or in mixture, where independently at each occurrence:
$R^1$ $R^2$ are independently selected from
hydrogen,
oxygen so as to form nitro,
amino,
sulfur so as to form —$SO_3$—R or —$SO_2$—R wherein R is selected from H and organic groups having 1–30 carbons optionally containing 1–6 heteroatoms selected from nitrogen, oxygen, phosphorous, silicon and sulfur, and
organic groups having 1–30 carbons and optionally containing 1–6 heteroatoms selected from nitrogen, oxygen, phosphorous, silicon, and sulfur,
$R^3$ and $R^4$ are independently selected from direct bonds to the carbons at numerals 6 and 7 respectively so as to form carbonyl groups, hydrogen, or a protecting group such that $R^3$ and/or $R^4$ is part of hydroxyl or carbonyl protecting group;
numerals 1 through 16 each represent a carbon, where carbons at numerals 1, 2, 4, 11, 12, 15 and 16 may be independently substituted with
(a) one of: =O, =C($R^5$)($R^5$) and =C=C($R^5$)($R^5$); or
(b) two of the following, which are independently selected: —X, —N($R^1$)($R^2$), —$R^5$ and —$OR^6$;
and where the carbon at numeral 17 is substituted with two of the following, which are independently selected: hydrogen, $C_{1-6}$alkyl and $C_{1-6}$haloalkyl;
and where carbons at numerals 5, 8, 9, 10, 13 and 14 may be independently substituted with one of —X, —$R^5$, —N($R^1$)($R^2$) or —$OR^6$;
in addition to the —$OR^3$ and —$OR^4$ groups as shown, each of the carbons at numerals 6 and 7 may be independently substituted with one of —X, —N($R^1$)($R^2$), —$R^5$ or —$OR^6$;
each of rings A, B, C and D is independently fully saturated, partially saturated or fully unsaturated;
at each occurrence is independently selected from H, X, and $C_{1-30}$ organic moiety that may optionally contain at least one heteroatom selected from the group consisting of boron, halogen, nitrogen, oxygen, silicon and sulfur;
$R^6$ is H or a protecting group such that —$OR^6$ is a protected hydroxyl group; and
X represents fluoride, chloride, bromide and iodide.
5. A compound of the formula

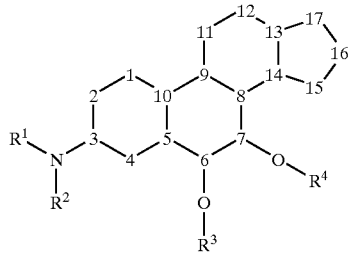

or pharmaceutically acceptable salts, solvates and stereoisomers thereof, in isolation or in mixture, where independently at each occurrence:
$R^1$ is hydrogen and $R^2$ is heteroalkyl selected from $C_{1-10}$alkyl-W—$C_{1-10}$alkylene- wherein W is selected from O and NH; HO-$C_{1-10}$alkylene-; and HO-$C_{1-10}$alkylene-W—$C_{1-10}$alkylene- where W is selected from O and N;
$R^3$ and $R^4$ independently selected from direct bonds to the carbons at numerals 6 and 7 respectively so as to form carbonyl groups, hydrogen, or a protecting group such that $R^3$ and/or $R^4$ is part of hydroxyl or carbonyl protecting group;
numerals 1 through 16 each represent a carbon, where carbons at numerals 1, 2, 4, 11, 12, 15 and 16 may be independently substituted with
(a) one of: =O, =C($R^5$)($R^5$) and =C=C($R^5$)($R^5$); or
(b) two of the following, which are independently selected: —X, —N($R^1$)($R^2$), —$R^5$ and —$OR^6$;
and where the carbon at numeral 17 is substituted with
(a) one of =C($R^5$)($R^5$) and =C=C($R^5$)($R^5$), or
(b) two of the following, which are independently selected: hydrogen, $C_{1-6}$alkyl and $C_{1-6}$haloalkyl;
and where carbons at numerals 5, 8, 9, 10, 13 and 14 may be independently substituted with one of —X, —$R^5$, —N($R^1$)($R^2$) or —$OR^6$;
in addition to the —$OR^3$ and —$OR^4$ groups as shown, each of the carbons at numerals 6 and 7 may be independently substituted with one of —X, —N($R^1$)($R^2$), —$R^5$ or —$OR^6$;
each of rings A, B, C and D is independently fully saturated, partially saturated or fully unsaturated;
$R^5$ at each occurrence is independently selected from H, X, and $C_{1-30}$ organic moiety that may optionally contain at least one heteroatom selected from the group consisting of boron, halogen, nitrogen, oxygen, silicon and sulfur;
$R^6$ is H or a protecting group such that —$OR^6$ is a protected hydroxyl group; and
X represents fluoride, chloride, bromide and iodide.
6. A compound of the formula

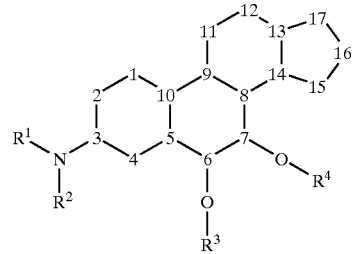

or pharmaceutically acceptable salts, solvates and stereoisomers thereof, in isolation or in mixture, where independently at each occurrence:
$R^1$ is hydrogen and $R^2$ is —$CH_2$—$R^7$ wherein $R^7$ is selected from alkyl-substituted phenyl; halogen-substituted phenyl; alkoxy-substituted phenyl; aryloxy-substituted phenyl; and nitro-substituted phenyl;
$R^3$ $R^4$ are independently selected from direct bonds to the carbons at numerals 6 and 7 respectively so as to form carbonyl groups, hydrogen, or a protecting group such that $R^3$ and/or $R^4$ is part of hydroxyl or carbonyl protecting group;

numerals 1 through 16 each represent a carbon, where carbons at numerals 1, 2, 4, 11, 12, 15 and 16 may be independently substituted with
 (a) one of: =O, =C(R$^5$)(R$^5$) and =C=C(R$^5$)(R$^5$); or
 (b) two of the following, which are independently selected: —X, —N(R$^1$)(R$^2$), —R$^5$ and —OR$^6$;
and where the carbon at numeral 17 is substituted with
 (a) one of =C(R$^5$)(R$^5$) and =C=C(R$^5$)(R$^5$), or
 (b) two of the following, which are independently selected: hydrogen, C$_{1-6}$alkyl and C$_{1-6}$haloalkyl;
and where carbons at numerals 5, 8, 9, 10, 13 and 14 may be independently substituted with one of —X, —R$^5$, —N(R$^1$)(R$^2$) or —OR$^6$;
in addition to the —OR$^3$ and —OR$^4$ groups as shown, each of the carbons at numerals 6 and 7 may be independently substituted with one of —X, —N(R$^1$)(R$^2$), —R$^5$ or —OR$^6$;
each of rings A, B, C and D is independently fully saturated, partially saturated or fully unsaturated;
R$^5$ at each occurrence is independently selected from H, X, and C$_{1-30}$ organic moiety that may optionally contain at least one heteroatom selected from the group consisting of boron, halogen, nitrogen, oxygen, silicon and sulfur;
R$^6$ is H or a protecting group such that —OR$^6$ is a protected hydroxyl group; and
X represents fluoride, chloride, bromide and iodide.

7. A compound of the formula

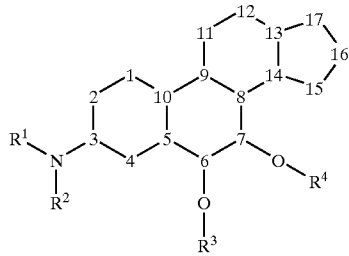

or pharmaceutically acceptable salts, solvates, and stereoisomers thereof, in isolation or in mixture, where independently at each occurrence:
 R$^1$ R$^2$ are each hydrogen;
 R$^3$ and R$^4$ are independently selected from a direct bond to the carbon at numerals 6 and 7 respectively so as to form carbonyl groups, hydrogen, or a protecting group such that R$^3$ and/or R$^4$ is part of hydroxyl or carbonyl protecting group;
 numerals 1 through 16 each represent a carbon, where carbons at numerals 1, 2, 4, 11, 12, 15 and 16 may be independently substituted with
  (a) one of: =O, =C(R$^5$)(R$^5$) and =C=C(R$^5$)(R$^5$); or
  (b) two of the following, which are independently selected: —X, —N(R$^1$)(R$^5$), —R$^5$ and —OR$^6$;
 and where the carbon at numeral 17 is substituted with
  (a) one of =C(R$^5$)(R$^5$) and =C=C(R$^5$)(R$^5$), or
  (b) two of the following, which are independently selected: hydrogen, C$_{1-6}$alkyl and C$_{1-6}$haloalkyl;
 and where carbons at numerals 5, 8, 9, 10, 13 and 14 may be independently substituted with one of —X, —R$^5$, —N(R$^1$)(R$^2$) or —OR$^6$;
 in addition to the —OR$^3$ and —OR$^4$ groups as shown, each of the carbons at numerals 6 and 7 may be independently substituted with one of —X, —N(R$^1$)(R$^2$), —R$^5$ or —OR$^6$;
 each of rings A, B, C and D is independently fully saturated, partially saturated or fully unsaturated;
 R$^5$ at each occurrence is independently selected from H, X, and C$_{1-30}$ organic moiety that may optionally contain at least one heteroatom selected from the group consisting of boron, halogen, nitrogen, oxygen, silicon and sulfur;
 R$^6$ is H or a protecting group such that —OR$^6$ is a protected hydroxyl group; and
 X represents fluoride, chloride, bromide and iodide.

8. A compound of the formula

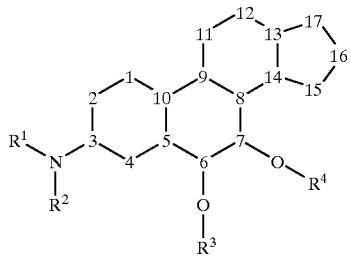

or pharmaceutically acceptable salts, solvates and stereoisomers thereof, in isolation or in mixture, where independently at each occurrence:
 R$^1$ and R$^2$ are independently selected from
  hydrogen,
  oxygen so as to form nitro,
  amino,
  sulfur so as to form —SO$_3$—R or —SO$_2$—R wherein R is selected from H and organic groups having 1–30 carbons optionally containing 1–6 heteroatoms selected from nitrogen, oxygen, phosphorous, silicon and sulfur, and
 organic groups having 1–30 carbons and optionally containing 1–6 heteroatoms selected from nitrogen, oxygen, phosphorous, silicon, and sulfur;
 R$^3$ and R$^4$ are independently selected from hydrogen and protecting groups such that R$^3$ and/or R$^4$ is part of hydroxyl protecting group;
 numerals 1 through 16 each represent a carbon;
 carbons at numerals 1, 2, 4, 11, 12, 15 and 16 are each substituted with two hydrogens unless said carbon is part of an unsaturated bond;
 carbons at numerals 5, 8, 9 and 14 are each substituted with one hydrogen unless said carbon is part of an unsaturated bond;
 carbon at numeral 10 is substituted with methyl;
 carbon at numeral 13 is substituted with methyl unless it is part of an unsaturated bond;
 and where the carbon at numeral 17 is substituted with
  (a) one of =C(R$^5$)(R$^5$) and =C=C(R$^5$)(R$^5$), or
  (b) two of the following, which are independently selected: hydrogen, C$_{1-6}$alkyl and C$_{1-6}$haloalkyl;
 in addition to the —OR$^3$ and —OR$^4$ groups as shown, each of carbons 6 and 7 may be independently substituted with one of —X, —N(R$^1$)(R$^2$), —R$^5$ or —OR$^6$;
 each of rings A, B, C and D is independently fully saturated, partially saturated or fully unsaturated;
 R$^5$ at each occurrence is independently selected from H and C$_{1-10}$ hydrocarbons;
 R$^6$ is H or a protecting group such that —OR$^6$ is a protected hydroxyl group; and
 X represents fluoride, chloride, bromide and iodide.

93

9. A compound of the formula

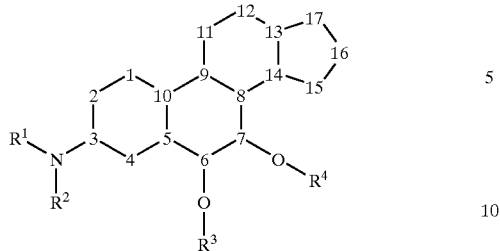

or pharmaceutically acceptable salts, solvates and stereoisomers thereof, in isolation or in mixture, where independently at each occurrence:

- $R^1$ and $R^2$ are independently selected from hydrogen, $CH_3$—, $CH_3(CH_2)_2$—, $CH_3(CH_2)_4$—, $CH_3CO$—, $C_6H_5CO$—$(CH_3)_2CHSO_2$—, $C_6H_5SO_2$—, $C_6H_5NHCO$—, $CH_3(CH_2)_2NHCO$—, $CH_3(CH_2)_2NH(CH_2)_2$—, $(CH_3)_2N(CH_2)_2$—, $HOCH_2CH_2$—, $HOCH_2(CH_2)_4$—, $HOCH_2CH_2NHCH_2CH_2$—, 3-$(CH_3)C_6H_4$—, 4-$(HO)C_6H_4$—, 4-$(H_2NSO_2)C_6H_4$—, 4-$((CH_3)_2CH)C_6H_4$—$CH_2$—, 2-$(F)C_6H_4$—$CH_2$—, 3-$(CF_3)C_6H_4$—$CH_2$—, 2-$(CH_3O)C_6H_4$—$CH_2$—, 4-$(CF_3O)C_6H_4$—$CH_2$—, 3-$(C_6H_5O)C_6H_4$—$CH_2$—, and 3-$(NO_2)C_6H_4$—$CH_2$—;
- $R^3$ and $R^4$ are selected from direct bonds to the carbons at numerals 6 and 7 respectively so as to form carbonyl groups, hydrogen, or a protecting group such that $R^3$ and/or $R^4$ is part of hydroxyl or carbonyl protecting group;
- numerals 1 through 16 each represent a carbon, where carbons at numerals 1, 2, 4, 11, 12, 15 and 16 may be independently substituted with
  (a) one of: =O, =C($R^5$)($R^5$) and =C=C($R^5$)($R^5$); or
  (b) two of the following, which are independently selected: —X, —N($R^1$)($R^2$), —$R^5$ and —$OR^6$;
- and where the carbon at numeral 17 is substituted with
  (a) one of =C($R^5$)($R^5$) and =C=C($R^5$)($R^5$), or
  (b) two of the following, which are independently selected: hydrogen, $C_{1-6}$alkyl and $C_{1-6}$haloalkyl;
- and where carbons at numerals 5, 8, 9, 10, 13 and 14 may be independently substituted with one of —X, —$R^5$, —N($R^1$)($R^2$) or —$OR^6$;
- in addition to the —$OR^3$ and —$OR^4$ groups as shown, each of the carbons at numerals 6 and 7 may be independently substituted with one of —X, —N($R^1$)($R^2$), —$R^5$ or —$OR^6$;
- each of rings A, B, C and D is independently fully saturated, partially saturated or fully unsaturated;
- $R^5$ at each occurrence is independently selected from H, X, and $C_{1-30}$ organic moiety that may optionally contain at least one heteroatom selected from the group consisting of boron, halogen, nitrogen, oxygen, silicon and sulfur;
- $R^6$ is H or a protecting group such that —$OR^6$ is a protected hydroxyl group; and
- X represents fluoride, chloride, bromide and iodide.

10. A compound of the formula

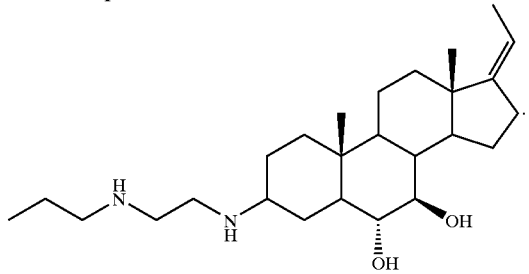

94

11. A compound of the formula

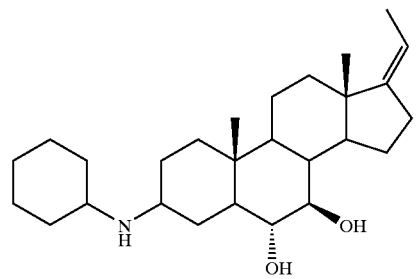

12. A compound of the formula

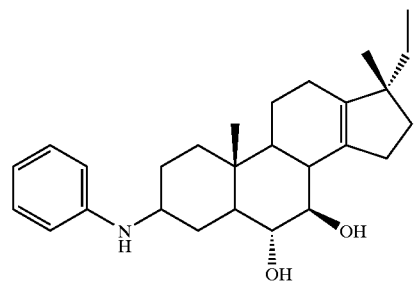

13. A compound of the formula

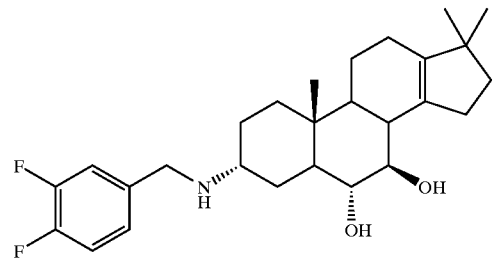

14. A compound of the formula

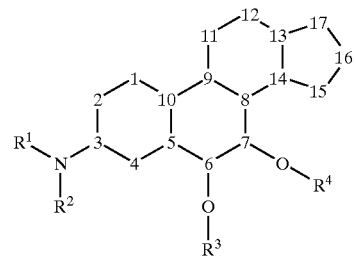

or pharmaceutically acceptable salts, solvates and stereoisomers thereof, in isolation or in mixture, where independently at each occurrence:

- $R^1$ and $R^2$ are hydrogen;
- $R^3$ and $R^4$ are independently selected from hydrogen and protecting groups such that $R^3$ and/or $R^4$ is part of hydroxyl protecting group;
- numerals 1 through 16 each represent a carbon;
- carbons at numerals 1, 2, 4, 11, 12, 15 and 16 are each substituted with two hydrogens;
- carbons at numerals 5, 8, 9 and 14 are each substituted with one hydrogen unless said carbon is part of an unsaturated bond;

carbon at numeral 10 is substituted with methyl;
carbon at numeral 13 is substituted with methyl unless it is part of an unsaturated bond;
and the carbon at numeral 17 is substituted with =C(R$^5$)(R$^5$) or two of the following, which are independently selected: hydrogen, C$_{1-6}$alkyl and C$_{1-6}$haloalkyl;
each of rings A, B, C and D is independently fully saturated or partially saturated; and
R$^5$ at each occurrence is independently selected from H and C$_{1-10}$ hydrocarbons.

15. A compound of the formula

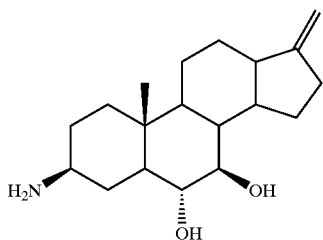

or pharmaceutically acceptable salts and solvates thereof.

16. A compound of the formula

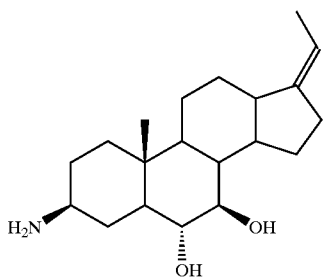

or pharmaceutically acceptable salts and solvates thereof.

17. A compound of the formula

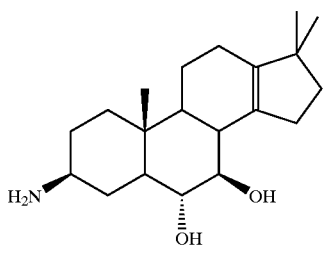

or pharmaceutically acceptable salts and solvates thereof.

18. A compound of the formula

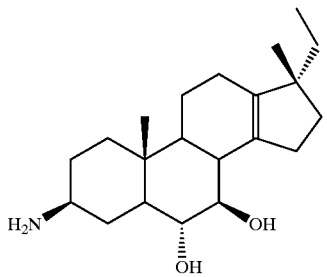

or pharmaceutically acceptable salts and solvates thereof.

19. A compound of the formula

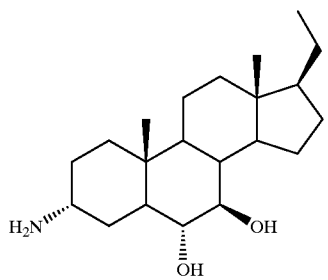

or pharmaceutically acceptable salts and solvates thereof.

20. A compound of the formula

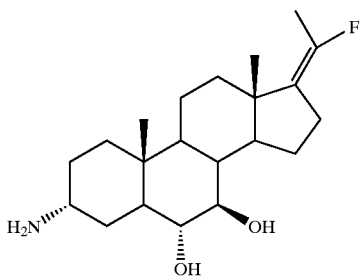

or pharmaceutically acceptable salts and solvates thereof.

21. The compound of any of claims 15–20 or pharmaceutically acceptable salts and solvates thereof.

22. A compound of the formula

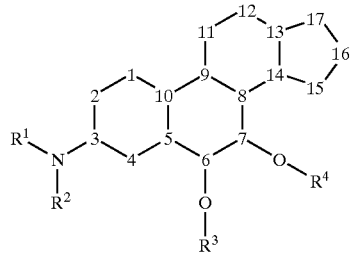

or pharmaceutically acceptable salts, solvates and stereoisomers thereof, in isolation or in mixture, where independently at each occurrence:

R$^1$ is hydrogen;
R$^2$ is hydrogen or C$_{1-10}$hydrocarbyl;
R$^3$ and R$^4$ are independently selected from direct bonds to the carbons at numerals 6 and 7 respectively so as to form carbonyl groups, hydrogen, or a protecting group such that R$^3$ and/or R$^4$ is part of hydroxyl or carbonyl protecting group;
numerals 1 through 16 each represent a carbon, where carbons at numerals 1, 2, 4, 11, 12, 15 and 16 may be independently substituted with
(a) one of: =O, =C(R$^5$)(R$^5$) and =C=C(R$^5$)(R$^5$); or
(b) two of the following, which are independently selected: —X, —N(R$^1$)(R$^2$), —R$^5$ and —OR$^6$;
and where the carbon at numeral 17 is substituted with
(a) one of =C(R$^5$)(R$^5$) and =C=C(R$^5$)(R$^5$), or
(b) two of the following, which are independently selected: hydrogen, C$_{1-6}$alkyl and C$_{1-6}$haloalkyl;
and where carbons at numerals 5, 8, 9, 10, 13 and 14 may be independently substituted with one of —X, —R$^5$, —N(R$^1$)(R$^2$) or —OR$^6$;

in addition to the —OR$^3$ and —OR$^4$ groups as shown, each of the carbons at numeral 6 and 7 may be independently substituted with one of —X, —N(R$^1$)(R$^2$), —R$^5$ or —OR$^6$;

each of rings A, B, C and D is independently fully saturated, partially saturated or fully unsaturated;

R$^5$ at each occurrence is independently selected from H, X, and C$_{1-30}$ organic moiety that may optionally contain at least one heteroatom selected from the group consisting of boron, halogen, nitrogen, oxygen, silicon and sulfur;

R$^6$ is H or a protecting group such that —OR$^6$ is a protected hydroxyl group; and X represents fluoride, chloride, bromide and iodide.

23. The compound of claim 22 wherein
carbons at numerals 1, 2, 4, 11, 12, 15 and 16 are each substituted with two hydrogens unless said carbon is part of an unsaturated bond;
carbons at numerals 5, 8, 9 and 14 are each substituted with one hydrogen unless said carbon is part of an unsaturated bond;
carbon at numeral 10 is substituted with methyl; and
carbon at numeral 13 is substituted with methyl unless it is part of an unsaturated bond.

24. The compound of claim 22 wherein the carbon at numeral 17 is substituted with =C(R$^5$)(R$^5$) and R$^5$ is independently selected from hydrogen, halogen, C$_{1-6}$alkyl, C$_{1-6}$hydroxyalkyl, and —CO$_2$—C$_{1-6}$alkyl.

25. The compound of claim 22 wherein the carbon at numeral 17 is substituted with C$_{1-6}$alkyl or C$_{1-6}$haloalkyl.

26. A compound of the formula

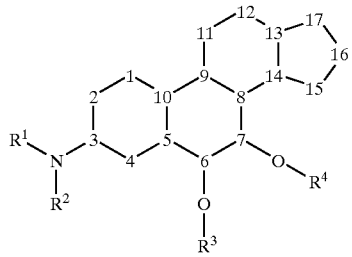

or pharmaceutically acceptable salts, solvates and stereoisomers thereof, in isolation or in mixture, where independently at each occurrence:

R$^1$ is hydrogen;

R$^2$ is hydrogen or heteroalkyl;

R$^3$ and R$^4$ are selected from direct bonds to 6 and 7 respectively so as to form carbonyl groups, hydrogen, or a protecting group such that R$^3$ and/or R$^4$ is part of hydroxyl or carbonyl protecting group;

numerals 1 through 16 each represent a carbon, where carbons at numerals 1, 2, 4, 11, 12, 15 and 16 may be independently substituted with
 (a) one of: =O, =C(R$^5$)(R$^5$) and =C=C(R$^5$)(R$^5$); or
 (b) two of the following, which are independently selected: —X, —N(R$^1$)(R$^2$), —R$^5$ and —OR$^6$;

and where the carbon at numeral 17 is substituted with =C(R$^5$)(R$^5$);

and where carbons at numerals 5, 8, 9, 10, 13 and 14 may be independently substituted with one of —X, —R$^5$, —N(R$^1$)(R$^2$) or —OR$^6$;

in addition to the —OR$^3$ and —OR$^4$ groups as shown, each of carbons 6 and 7 may be independently substituted with one of —X, —N(R$^1$)(R$^2$), —R$^5$ or —OR$^6$;

each of rings A, B, C and D is independently fully saturated, partially saturated or fully unsaturated;

R$^5$ at each occurrence is independently selected from hydrogen, halogen, C$_{1-6}$alkyl, C$_{1-6}$hydroxyalkyl, and —CO$_2$—C$_{1-6}$alkyl;

R$^6$ is H or a protecting group such that —OR$^6$ is a protected hydroxyl group; and X represents fluoride, chloride, bromide and iodide.

27. A compound of the formula

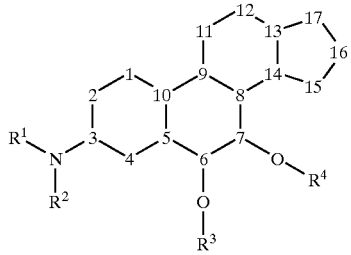

or pharmaceutically acceptable salts, solvates and stereoisomers thereof, in isolation or in mixture, where independently at each occurrence:

R$^1$ is hydrogen;

R$^2$ is hydrogen or heteroalkyl;

R$^3$ and R$^4$ are selected from direct bonds to 6 and 7 respectively so as to form carbonyl groups, hydrogen, or a protecting group such that R$^3$ and/or R$^4$ is part of hydroxyl or carbonyl protecting group;

numerals 1 through 16 each represent a carbon, where carbons at numerals 1, 2, 4, 11, 12, 15 and 16 may be independently substituted with
 (a) one of: =O, =C(R$^5$)(R$^5$) and =C=C(R$^5$)(R$^5$); or
 (b) two of the following, which are independently selected: —X, —N(R$^1$)(R$^2$), —R$^5$ and —OR$^6$;

and where the carbon at numeral 17 is substituted with C$_{1-6}$alkyl and C$_{1-6}$haloalkyl;

and where carbons at numerals 5, 8, 9, 10, 13 and 14 may be independently substituted with one of —X, —R$^5$, —N(R$^1$)(R$^2$) or —OR$^6$;

in addition to the —OR$^3$ and —OR$^4$ groups as shown, each of carbons 6 and 7 may be independently substituted with one of —X, —N(R$^1$)(R$^2$), —R$^5$ or —OR$^6$;

each of rings A, B, C and D is independently fully saturated, partially saturated or fully unsaturated;

R$^5$ at each occurrence is independently selected from H, X, and C$_{1-30}$ organic moiety that may optionally contain at least one heteroatom selected from the group consisting of boron, halogen, nitrogen, oxygen, silicon and sulfur;

R$^6$ is H or a protecting group such that —OR$^6$ is a protected hydroxyl group; and X represents fluoride, chloride, bromide and iodide.

28. The hydrochloride or acetate salt of any one of claims 1, 3–4, 5, 6–7, 8, 9–13, 14–20, 22 and 26–27.

29. A pharmaceutical composition comprising a compound of any one of claims 1, 3–4, 5, 6–7, 8, 9–13, 14–20, 22, and 26–27 and a pharmaceutically acceptable carrier, excipient or diluent.

30. A method of treating inflammation therapeutically comprising administering to a subject in need thereof a therapeutically effective amount of a compound of any one of claims 1, 3–4, 5, 6–7, 8, 9–13, 14–20, 22 and 26–27.

31. A method of treating inflammation prophylactically comprising administering to a subject in need thereof a prophylactically effective amount of a compound of any one of claims 1, 3–4, 5, 6–7, 8, 9–13, 14–20, 22 and 26–27.

* * * * *

UNITED STATES PATENT AND TRADEMARK OFFICE
CERTIFICATE OF CORRECTION

PATENT NO.    : 6,635,629 B2
DATED         : October 21, 2003
INVENTOR(S)   : Jeffery R. Raymond et al.

It is certified that error appears in the above-identified patent and that said Letters Patent is hereby corrected as shown below:

Column 88,
Line 3, "at each" should read as -- $R^5$ at each --
Line 37, "wherein $R^5$" should read as -- wherein $R^2$ --

Column 89,
Line 16, "$R^1\ R^2$" should read as -- $R^1$ and $R^2$ --

Column 90,
Line 63, "$R^3\ R^4$" should read as -- $R^3$ and $R^4$ --

Column 91,
Line 45, "$R^1\ R^2$" should read as -- $R^1$ and $R^2$ --
Line 55, "$N(R^1)(R^5)$," should read as -- $N(R^1)(R^2)$, --

Column 95,
Line 4, "and the" should read as -- and where the --
Lines 12-22, the compound formula:

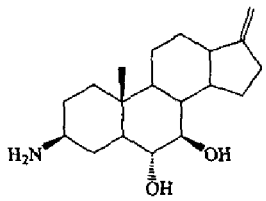  should read as the compound formula: 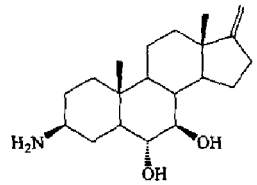

Lines 26-36, the compound formula:

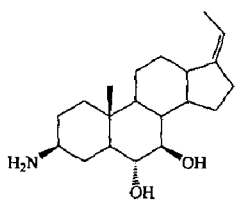  should read as the compound formula: 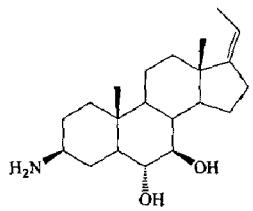

UNITED STATES PATENT AND TRADEMARK OFFICE
CERTIFICATE OF CORRECTION

PATENT NO. : 6,635,629 B2
DATED : October 21, 2003
INVENTOR(S) : Jeffery R. Raymond et al.

It is certified that error appears in the above-identified patent and that said Letters Patent is hereby corrected as shown below:

<u>Column 96,</u>
Line 32, "thereof." should read as -- thereof, excluding prodrug forms thereof. --

Signed and Sealed this

First Day of March, 2005

JON W. DUDAS
*Director of the United States Patent and Trademark Office*

UNITED STATES PATENT AND TRADEMARK OFFICE
CERTIFICATE OF CORRECTION

PATENT NO. : 6,635,629 B2
DATED : October 21, 2003
INVENTOR(S) : Raymond, Jeffery R. et al.

It is certified that error appears in the above-identified patent and that said Letters Patent is hereby corrected as shown below:

Column 89,
Line 49, "at each" should read as -- $R^5$ at each --.

Signed and Sealed this

Twenty-seventh Day of September, 2005

JON W. DUDAS
*Director of the United States Patent and Trademark Office*